US012590965B2

(12) United States Patent
Di Vizio et al.

(10) Patent No.: US 12,590,965 B2
(45) Date of Patent: Mar. 31, 2026

(54) PALMITOYL PROTEIN BIOMARKERS IN PURIFIED EXTRACELLULAR VESICLES FOR EARLY IDENTIFICATION OF CLINICALLY SIGNIFICANT PROSTATE CANCER

(71) Applicants:CEDARS-SINAI MEDICAL CENTER, Los Angeles, CA (US); Vanderbilt University, Nashville, TN (US)

(72) Inventors: Dolores Di Vizio, Los Angeles, CA (US); Wei Yang, Studio City, CA (US); Javier Mariscal Avila, Los Angeles, CA (US); Tatyana Vagner, Los Angeles, CA (US); Sungyong You, Los Angeles, CA (US); Andries Zijlstra, Nashville, TN (US)

(73) Assignees: Cedars-Sinai Medical Center, Los Angeles, CA (US); Vanderbilt University, Nashville, TN (US)

( * ) Notice: Subject to any disclaimer, the term of this patent is extended or adjusted under 35 U.S.C. 154(b) by 1355 days.

(21) Appl. No.: 16/921,646

(22) Filed: Jul. 6, 2020

(65) Prior Publication Data

US 2020/0408766 A1      Dec. 31, 2020

Related U.S. Application Data

(63) Continuation-in-part of application No. 13/975,059, filed on Aug. 23, 2013, now abandoned.

(60) Provisional application No. 61/692,591, filed on Aug. 23, 2012.

(51) Int. Cl.
*G01N 33/574* (2006.01)
*G01N 33/68* (2006.01)

(52) U.S. Cl.
CPC ... *G01N 33/57434* (2013.01); *G01N 33/6848* (2013.01)

(58) Field of Classification Search
None
See application file for complete search history.

(56) References Cited

U.S. PATENT DOCUMENTS

| | | | |
|---|---|---|---|
| 6,258,540 B1 | 7/2001 | Lo et al. | |
| 6,355,623 B2 | 3/2002 | Seidman et al. | |
| 6,812,023 B1 | 11/2004 | Lamparski et al. | |
| 10,254,285 B2 | 4/2019 | Di Vizio et al. | |
| 11,274,349 B2 | 3/2022 | Di Vizio et al. | |
| 2006/0019256 A1 | 1/2006 | Clarke et al. | |
| 2008/0199890 A1 | 8/2008 | Letai | |
| 2010/0184046 A1 | 7/2010 | Klas et al. | |
| 2010/0196426 A1 | 8/2010 | Skog et al. | |
| 2010/0304989 A1 | 12/2010 | Von Hoff et al. | |
| 2011/0200998 A1 | 8/2011 | Weichselbaum et al. | |
| 2014/0038901 A1 | 2/2014 | Lyden et al. | |
| 2014/0045915 A1 | 2/2014 | Skog et al. | |
| 2014/0056807 A1* | 2/2014 | Di Vizio .................. G01N 1/34 435/7.1 |
| 2014/0148350 A1 | 5/2014 | Spetzler et al. | |
| 2015/0301055 A1 | 10/2015 | Spetzler | |
| 2016/0061842 A1 | 3/2016 | Di Vizio et al. | |
| 2019/0300966 A1 | 10/2019 | Di Vizio et al. | |

FOREIGN PATENT DOCUMENTS

| | | | |
|---|---|---|---|
| EP | 2986326 A2 | 10/2014 | |
| EP | 2986326 B1 | 9/2018 | |
| WO | WO 2012/115885 A1 | 8/2012 | |
| WO | WO 2014/172390 A2 | 10/2014 | |
| WO | WO 2018089541 A1 | 5/2018 | |
| WO | WO-2019008414 A1 * | 1/2019 | |

OTHER PUBLICATIONS

International Search Report and Written Opinion of PCT/US2017/60707, dated Mar. 29, 2018, 11 Pages.
International Preliminary Report on Patentability of PCT/US2014/034245 dated Oct. 20, 2015; 8 pages.
International Search Report and Written Opinion of PCT/US2014/034245 dated Nov. 7, 2014; 13 pages.
Extended Search Report of EP Application No. 14785880.7 dated Dec. 19, 2016; 13 pages.
Adlard et al.. Prediction of the Response of Colorectal Cancer to Systemic Therapy, The Lancet Oncology, 2002, vol. 3, pp. 75-82.
Bhardwaj et al. Physicochemical properties of extruded and non-extruded liposomes containing the hydrophobic drug dexamethasone. International Journal of Pharmaceutics (2010). 388:181-189.
Chambers et al. Microvesicle-mediated release of soluble LH/hCG receptor (LHCGR) from transfected cells and placenta explants. Reproductive Biology and Endocrinology (2011). 9:64 (15 pages).
Cheruvanky et al. Rapid isolation of urinary exosomal biomarkers using a nanomembrane ultrafiltration concentrator. Am J Physiol Renal Physiol (2007). 292:F1657-F1661.
Conley et al., High-Throughput Sequencing of Two Populations of Extracellular Vesicles Provides an mRNA Signature that can be Detected in the Circulation of Breast Cancer Patients, 2017, RNA Biology, vol. 14(3), pp. 305-316.
D'Asti et al. Oncogenic extracellular vesicles in brain tumor progression. Frontiers in Physiology (2012). 3:Article 294 (15 pages).
Di Vizio et al. Large Oncosomes in Human Prostate Cancer Tissues and in the Circulation of Mice with Metastatic Disease. The American Journal of Pathology (2012). 181(5):1573-1584.

(Continued)

*Primary Examiner* — Jennifer Chin
(74) *Attorney, Agent, or Firm* — Linda B. Huber; Nixon Peabody LLP

(57) ABSTRACT

The invention provides for methods for isolating large EVs and detecting palmitoyl proteins in the large EVs, as well as methods for detecting clinically significant prostate cancer based on the presence of palmitoyl proteins in the isolated large EVs in a subject in need thereof. The method further comprises administering cancer therapy to the subject.

11 Claims, 29 Drawing Sheets

(56) References Cited

OTHER PUBLICATIONS

Di Vizio et al. Oncosome Formation in Prostate Cancer: Association with a Region of Frequent Chromosomal Deletion in Metastatic Disease. Cancer Research (2009). 69:5601-5609.

Dragovic et al. Sizing and phenotyping of cellular vesicles using Nanoparticle Tracking Analysis. Nanomedicine: Nanotechnology, Biology, and Medicine (2011). 7:780-788.

D'Souza-Schorey et al. Tumor-derived microvesicles: shedding light on novel microenvironment modulators and prospective cancer biomarkers. Genes & Development (2012). 1287-1299.

Fiskaa et al., Distinct Small RNA Signatures in Extracellular Vesicles Derived from Breast Cancer Cell Lines, 2016, PLoS One, vol. 11(8), e0161824, 18 Pages.

Floryan et al. Intraoperative use of autologous platelet-rich and platelet-poor plasma for orthopedic surgery patients. AORN Journal (2004). 80:668-674.

Freshney, Culture of Animal Cells, A Manual of Basic Technique, 1983, pp. 1-4.

Fujita et al., Extracellular Vesicle Transfer of Cancer Pathogenic Components, 2016, Cancer Science, vol. 107(4), pp. 385-390.

Gerdes et al., Emerging Understanding of Multiscale Tumor Heterogeneity, Frontiers in Oncology, 2014, 4(Article 366), pp. 1-12.

Kaiser, First Pass at Cancer Genome Reveals Complex Landscape, Science, 2006, vol. 313, p. 1370.

Morello et al. Abstract 430: MiRNA profiling of prostate cancer cell-derived large oncosomes identifies a signature of invasion and metastasis. Cancer Research (2012). 72(5): Suppl 1 (1 page).

Morello et al. Large oncosomes mediate intercellular transfer of functional microRNA. Cell Cycle (2013). 12(22):3526-3536.

Muralidharan-Chari et al. Microvesicles: mediators of extracellular communication during cancer progression. Journal of Cell Science (2010). 123:1603-1611.

Myers et al. Successful Treatment of Advanced Metastatic Prostate Cancer following Chemotherapy Based on Molecular Profiling. Case Reports in Oncology (2012). 5(1):154-158.

Peinado et al. Melanoma exosomes educate bone marrow progenitor cells toward a pro-metastatic phenotype through MET. Nat Med (2012). 18(6):883-891.

Pritzker. K., Cancer Biomarkers: Easier Said Than Done, Clinical Chemistry, 2002, vol. 48(8), pp. 1147-1150.

Response to Office Action (issued Jul. 9, 2018) of U.S. Appl. No. 14/883,421, filed Sep. 28, 2018, 5 Pages.

Shao et al. Protein typing of circulating microvesicles allows real-time monitoring of gliobastoma therapy. Nat Med (2012). 18(12):1835-1840.

Tian et al., The Expression of Native and Cultured RPE Grown on Different Matrices, Physiol Genomics, 2004, vol. 17, pp. 170-182.

Xiao et al. Effect of 5-Aza-2' deoxycytidine on immune-associated proteins in exosomes from hepatoma. World Journal of Gastroenterology (2010). 16(19):2371-2377.

Zips et al., New Anticancer Agents: In Vitro and In Vivo Evaluation, In Vivo, 2005, vol. 19, pp. 1-8.

Haynes et al., Proteome analysis: Biological assay or data archive?, Electrophoresis, 1998, vol. 19, pp. 1862-1871.

Chen et al., Discordant Protein and mRNA Expression in Lung Adenocarcinomas, 2002, Molecular & Cellular Proteomics, vol. 1, pp. 304-313.

Vogel et al., Nature Reviews Genetics, 2012, vol. 13(4), pp. 227-232.

Conley et al., Abstracts from the fourth International Meeting of ISEV, ISEV2015, Washington, D.C., USA, Apr. 23-26, 2015, Journal of Extracellular Vesicles, 2015, vol. 4(10).

Spinelli et al., J Extracell Vesicles, 2015, vol. 4(10).

Conley et al., Supplementary Tables, retrieved from: https://www.tandfonline.com/doi/full/10.1080/15476286.2016.1259061#supplemental-material-section, RNA Biology, 2017, vol. 14(3), pp. 1-890.

* cited by examiner

| Median Rank | p-Value | Gene |
|---|---|---|
| 757.0 | 9.30E-4 | ARF6 |

| 1 | 2 | 3 | 4 | 5 | 6 | 7 | 8 | 9 |
|---|---|---|---|---|---|---|---|---|

Legend

1. Prostate Carcinoma vs. Normal
Lapointe Prostate, Proc Natl Acad Sci U S A, 2004
2. Prostate Carcinoma vs. Normal
Liu Prostate, Cancer Res, 2006
3. Prostate Carcinoma vs. Normal
Luo Prostate 2, Mol Carcinog, 2002
4. Prostate Carcinoma vs. Normal
Singh Prostate, Cancer Cell, 2002
5. Prostate Carcinoma Epithelia vs. Normal
Tomlins Prostate, Nat Genet, 2007

6. Prostate Adenocarcinoma vs. Normal
Vanaja Prostate, Cancer Res, 2003
7. Prostate Adenocarcinoma vs. Normal
Wallace Prostate, Cancer Res, 2008
8. Prostate Carcinoma vs. Normal
Welsh Prostate, Cancer Res, 2001
9. Prostate Carcinoma vs. Normal
Yu Prostate, J Clin Oncol, 2004

G

Novel filtration-based method of oncosome purification

Filtration-based method of large oncosome purification a b

Palmitoyl-proteins identified in prostate cancer circulating L-EVs

B

| Symbol | EntrezID | Protein abundance |
|---|---|---|
| GNAQ | 2776 | 30.36 |
| CD9 | 928 | 29.84 |
| TLN1 | 7094 | 29.07 |
| STX11 | 8676 | 28.94 |
| ITGB3 | 3690 | 28.89 |
| LYN | 4067 | 28.88 |
| SLC4A1 | 6521 | 28.86 |
| CANX | 821 | 28.76 |
| FLOT2 | 2319 | 28.73 |
| FLOT1 | 10211 | 28.67 |
| ABHD16A | 7920 | 28.26 |
| MYADM | 91663 | 28.20 |
| ATP2A3 | 489 | 28.08 |
| TMX1 | 81542 | 28.02 |
| RAP2B | 5912 | 28.02 |
| ATP2A2 | 488 | 27.77 |
| SLC2A3 | 6515 | 27.70 |
| RTN4 | 57142 | 27.60 |
| LTBP1 | 4052 | 27.45 |
| ABCC4 | 10257 | 27.41 |

PALMITOYL PROTEIN BIOMARKERS IN PURIFIED EXTRACELLULAR VESICLES FOR EARLY IDENTIFICATION OF CLINICALLY SIGNIFICANT PROSTATE CANCER

CROSS-REFERENCE TO RELATED APPLICATIONS

This application claims benefit under 35 U.S.C. § 120 as a continuation-in-part of U.S. application Ser. No. 13/975, 059, filed Aug. 23, 2013, which claims priority from U.S. Provisional Patent Application No. 61/692,591, filed on Aug. 23, 2012, which is incorporated herein by reference in its entirety.

STATEMENT REGARDING FEDERALLY SPONSORED RESEARCH OR DEVELOPMENT

This invention was made with Government support under Grant Nos. CA131472, CA143777, and CA218526 awarded by the National Institutes of Health. The government has certain rights in the invention.

STATEMENT REGARDING PRIOR DISCLOSURES BY THE INVENTOR OR A JOINT INVENTOR

The following article is a grace period inventor disclosure by one or more of the following authors: Javier Mariscal, Tatyana Vagner, Minhyung Kim, Bo Zhou, Andrew Chin, Mandana Zandian, Michael R. Freeman, Sungyong You, Andries Zijlstra, Wei Yang & Dolores Di Vizio (2020) Comprehensive palmitoyl-proteomic analysis identifies distinct protein signatures for large and small cancer-derived extracellular vesicles, Journal of Extracellular Vesicles, 9:1, DOI: 10.1080/20013078.2020.1764192

FIELD OF INVENTION

The invention provides methods for isolating large oncosomes, methods for identifying large oncosomes, methods for determining the likelihood of cancer metastasis in a subject in need thereof by detecting large oncosomes and/or its molecular contents (proteins, nucleic acids and/or lipids) and methods for treating cancer in a subject in need thereof.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Cancer metastases may result from cancer cells growing directly into the tissue surrounding the tumor, cancer cells traveling through the blood stream to distant locations and/or cancer cells traveling through the lymphatic system to nearby or distant lymph nodes. There is no single test for detecting tumor metastasis in general. Routine blood tests detecting specific markers may indicate metastasis but the blood tests are often normal in subjects with advanced forms of cancer. Existing imaging techniques have their limitations as well and are expensive, time consuming. There is a need in the art for tests simple blood to detect cancer metastasis.

Herein, inventors show that cancer cells shed large oncosomes. Presence of large oncosomes or an increase in the number of large oncosomes in a sample obtained from a subject that has or had cancer can be indicative of tumor metastases.

Further, the inventors show herein that there are highly abundant palmitoyl proteins in large oncosomes that are not detected in unfractionated plasma. The presence of these palmitoyl proteins in these large oncosomes can be indicative of clinically significant prostate cancer.

SUMMARY OF THE INVENTION

The present invention is based on the discovery that cancer cells shed microvesicles such as large extracellular vesicles (EVs) which contain molecular material such as palmitoyl proteins that are indicatative of disease state.

Various embodiments of the present invention provide for a method of detecting one or more palmitoyl proteins, comprising: obtaining a biological sample from a subject having prostate cancer or suspected of having prostate cancer; isolating large extracellular vesicles (EVs) from the biological sample; assaying the large EVs for at least 10 palmitoyl proteins selected from the group consisting of GNAQ, CD9, TLN1, STX11, ITGB3, LYN, SLC4A1, CANX, FLOT2, FLOT1, ABHD16A, MYADM, ATP2A3, TMX1, RAP2B, ATP2A2, SLC2A3, RTN4, LTBP1, and ABCC4; and detecting the one or more palmitoyl proteins selected from the group consisting of GNAQ, CD9, TLN1, STX11, ITGB3, LYN, SLC4A1, CANX, FLOT2, FLOT1, ABHD16A, MYADM, ATP2A3, TMX1, RAP2B, ATP2A2, SLC2A3, RTN4, LTBP1, and ABCC4.

In various embodiments, the method can comprise assaying the large EVs for at least 15 palmitoyl proteins. In various embodiments, the method can comprise assaying the large EVs for all 20 palmitoyl proteins.

In various embodiments, the method can further comprise assaying for one or more additional palmitoyl proteins other than GNAQ, CD9, TLN1, STX11, ITGB3, LYN, SLC4A1, CANX, FLOT2, FLOT1, ABHD16A, MYADM, ATP2A3, TMX1, RAP2B, ATP2A2, SLC2A3, RTN4, LTBP1, and ABCC4.

In various embodiments, the biological sample can be blood plasma. In various embodiments, the subject can have prostate cancer. In various embodiments, the subject can have metastatic prostate cancer.

In various embodiments, assaying for at least 10 palmitoyl proteins can comprise using mass spectrometry to detect the at least one palmitoyl proteins.

Various embodiments of the invention provide for a method of detecting clinically significant prostate cancer, comprising: obtaining a biological sample from a subject having prostate cancer or suspected of having prostate cancer; isolating large extracellular vesicles (EVs) from the biological sample; assaying the large EVs for at least 10 palmitoyl proteins selected from the group consisting of GNAQ, CD9, TLN1, STX11, ITGB3, LYN, SLC4A1, CANX, FLOT2, FLOT1, ABHD16A, MYADM, ATP2A3, TMX1, RAP2B, ATP2A2, SLC2A3, RTN4, LTBP1, and ABCC4; and detecting the one or more palmitoyl proteins selected from the group consisting of GNAQ, CD9, TLN1, STX11, ITGB3, LYN, SLC4A1, CANX, FLOT2, FLOT1, ABHD16A, MYADM, ATP2A3, TMX1, RAP2B, ATP2A2, SLC2A3, RTN4, LTBP1, and ABCC4, wherein the detection of the one or more palmitoyl proteins indicates the presence of clinically significant prostate cancer.

In various embodiments, the method can comprise assaying the large EVs for at least 15 palmitoyl proteins. In various embodiments, the method can comprise assaying the large EVs for all 20 palmitoyl proteins.

In various embodiments, the method can further comprise administering a therapy other than androgen deprivation therapy when the one or more palmitoyl proteins are detected, or continuing to administer androgen deprivation therapy when the one or more palmitoyl proteins are not detected, or continuing active surveillance when the one or more palmitoyl proteins are not detected. In various embodiments, assaying the large EVs for at least 10 palmitoyl proteins can comprise using mass spectrometry to assay for the at least 10 palmitoyl proteins.

Various embodiments provide for an assay kit, comprising: a reagent to isolate large extracellular vesicles (EVs) from a biological sample; and a reagent to immobilize the large EVs.

In various embodiments, the reagent to isolate the large EVs can comprise magnetic bead conjugated with antibodies that binds specifically to the large EVs. In various embodiments, the assay kit can comprise 10 or more antibodies, each of which specifically binds to a different palmitoyl protein selected from the group consisting of GNAQ, CD9, TLN1, STX11, ITGB3, LYN, SLC4A1, CANX, FLOT2, FLOT1, ABHD16A, MYADM, ATP2A3, TMX1, RAP2B, ATP2A2, SLC2A3, RTN4, LTBP1, and ABCC4. In various embodiments, the assay kit can further comprise an enzyme to digest palmitoyl proteins isolated from the large oncosomes.

DETAILED DESCRIPTION OF THE INVENTION

Figure 1:
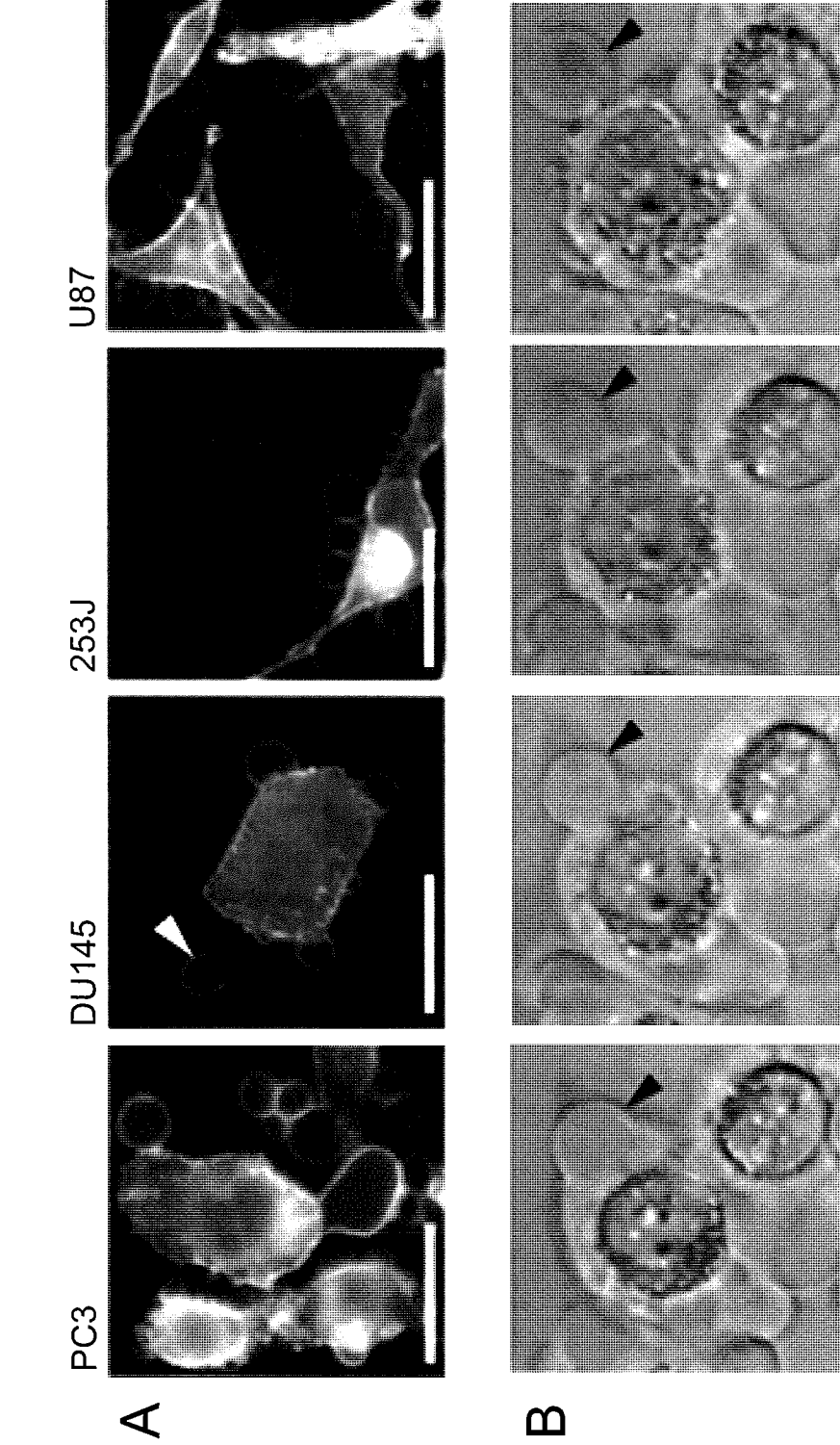
FIG. 1, panels A-G, depicts, in accordance with an embodiment of the invention the characterization and detection of shed tumor cell-derived vesicles. (A) Prostate cancer (PC3, DU145), bladder cancer (253J), and glioblastoma (U87) cell lines stained with FITC-Cholera Toxin B (CTxB) and imaged by confocal microscopy (scale bar: 10 μm). (B) CTxB-labeled DU145 cells showing large, bulbous membrane protrusions, and several large vesicles released into the surrounding environment. (C) Nucleic acid extracted from vesicles shed from LNCaP/MyrAkt1 cells. Total RNA/DNA was treated with RNase A or DNase 1 and samples electrophoresed through 2% agarose. (D) FACS analysis of vesicles, isolated from the medium of WPMY-1 and LNCaP/MyrAkt1 cells treated with EGF (50 ng/ml), fixed, permeabilized, and stained with PI. The dot plots depict FSC and FL2 (PI). The red gates surround PI-positive events, graphed on the right; p<2.2e-16. (E) Left panel: photomicrograph of FITC-labeled gelatin matrix loaded with a biochemical preparation of vesicles shed from LNCaP/MyrAkt1 cells (40×), showing large zones of proteolytic clearance. Trypsin was used as a positive control; a general protease inhibitor and vehicle served as negative controls. Right panel: shed vesicles (SV) were analyzed via gelatin zymography (substrate gel electrophoresis), showing active MMP-9 and MMP-2. (F) Top, LNCaP/MyrAkt1 cells stained with FITC-CTxB. Note the large size of 2 membrane vesicles. Bottom, FITC-labeled gelatin after exposure to SV. (G) CTxB-labeled membrane blebs (n=150) and gelatin degradation spots (n=135) were measured by AxioVision Rel. 4.5, and plotted graphically (mode: 3.1-4 μm). (H) The CTxB-labeled membrane blebs (n=150) and gelatin degradation spots (n=135) are measured by AxioVision version 4.5 (Zeiss) and plotted graphically (mode, 3.1 to 4 μm).
Figure 1:
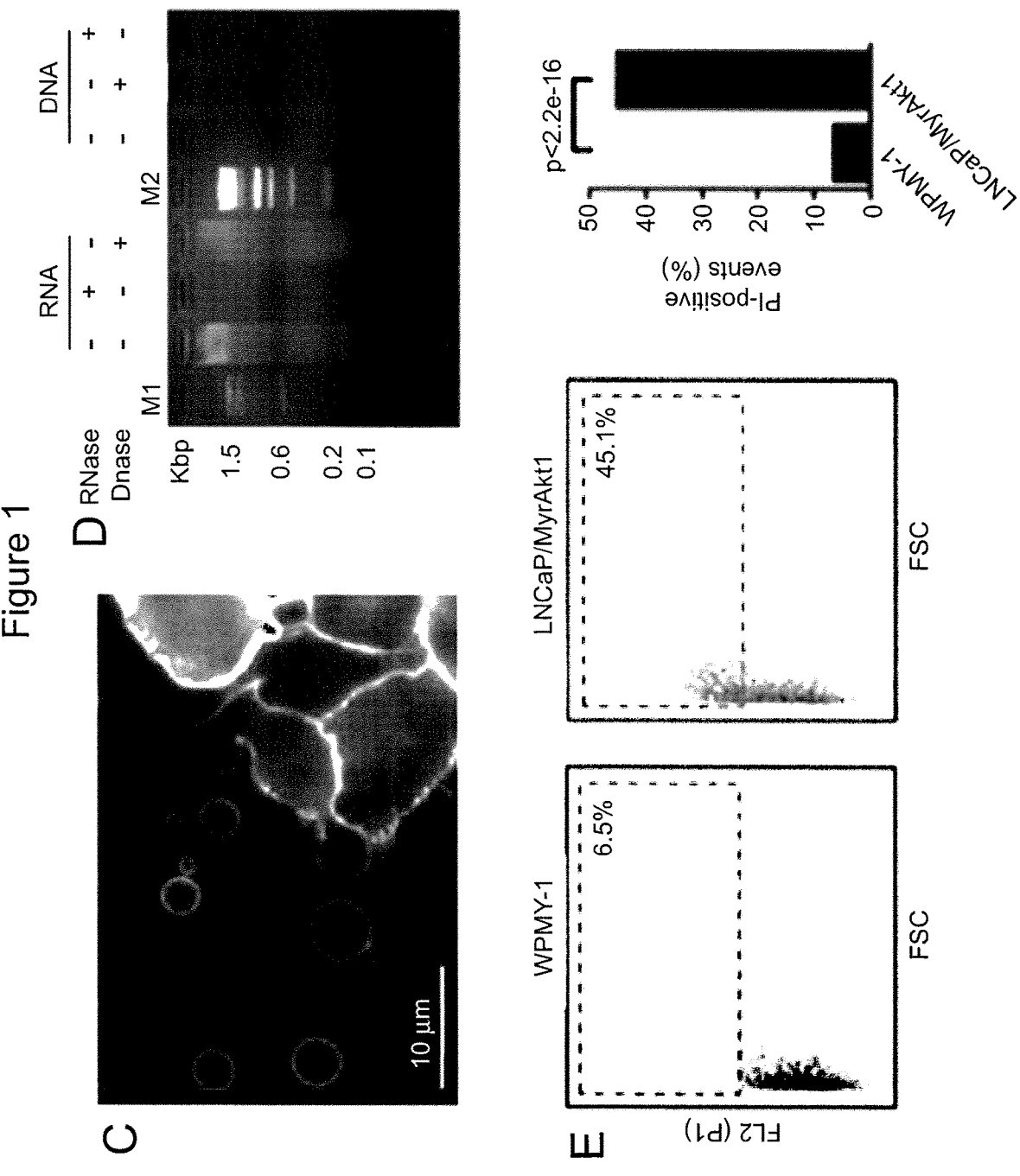
Figure 1:
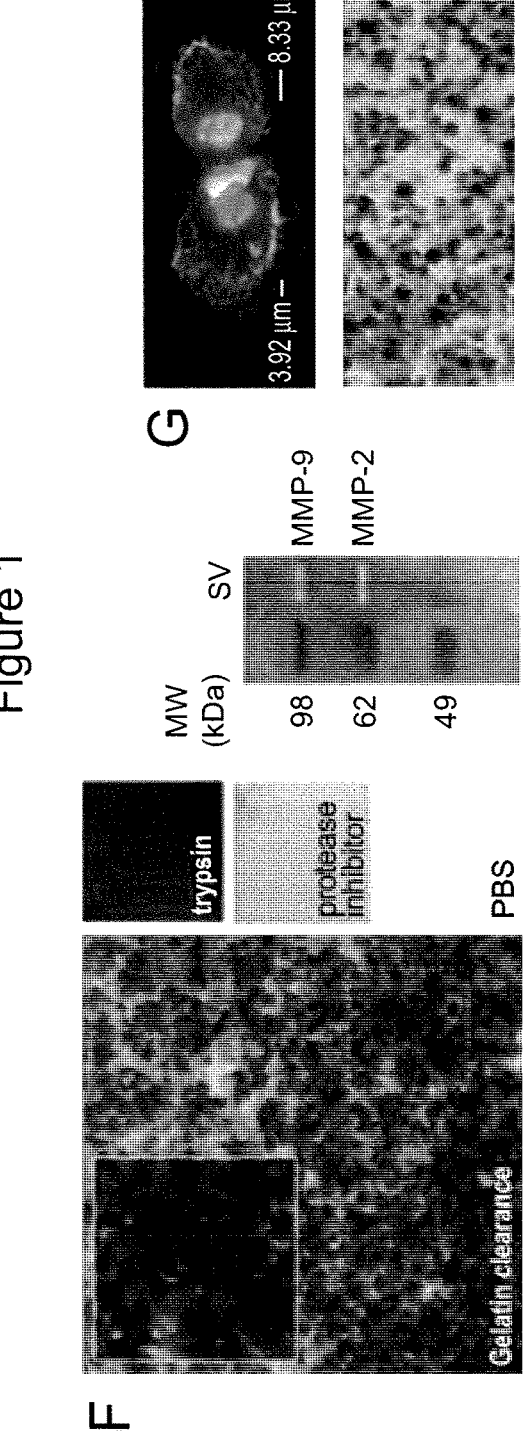
Figure 1:
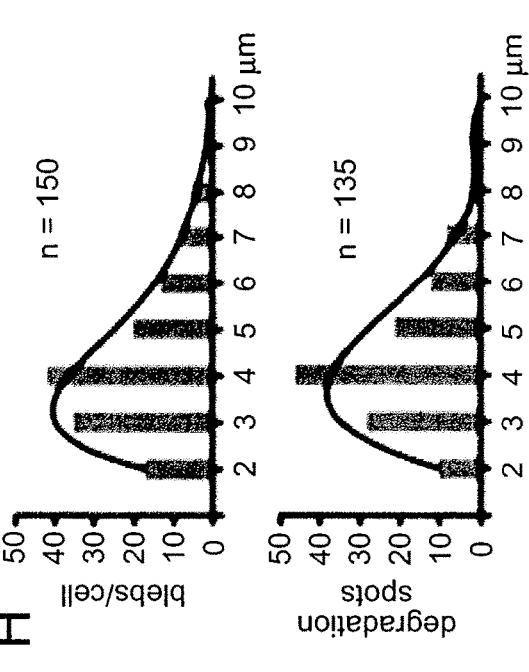

All references cited herein, including the references cited therein, are incorporated by reference in their entirety as though fully set forth. Unless defined otherwise, technical and scientific terms used herein have the same meaning as commonly understood by one of ordinary skill in the art to which this invention belongs.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

As used herein the term "about" when used in connection with a referenced numeric indication means the referenced numeric indication plus or minus up to 5% of that referenced numeric indication, unless otherwise specifically provided for herein. For example, the language "about 50%" covers the range of 45% to 55%. In various embodiments, the term "about" when used in connection with a referenced numeric indication can mean the referenced numeric indication plus or minus up to 4%, 3%, 2%, 1%, 0.5%, or 0.25% of that referenced numeric indication, if specifically provided for in the claims.

"Beneficial results" may include, but are in no way limited to, lessening or alleviating the severity of the disease condition, preventing the disease condition from worsening, curing the disease condition, preventing the disease condition from developing, lowering the chances of a patient developing the disease condition and prolonging a patient's life or life expectancy. In some embodiments, the disease condition is cancer.

"Cancer" and "cancerous" refer to or describe the physiological condition in mammals that is typically characterized by unregulated cell growth. Examples of cancer include, but are not limited to B-cell lymphomas (Hodgkin's lymphomas and/or non-Hodgkins lymphomas), brain tumor, breast cancer, colon cancer, lung cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, brain cancer, and prostate cancer, including but not limited to androgen-dependent prostate cancer and androgen-independent prostate cancer.

"Chemotherapeutic drugs" or "chemotherapeutic agents" as used herein refer to drugs used to treat cancer including but not limited to Albumin-bound paclitaxel (nab-paclitaxel), Actinomycin, Alitretinoin, All-trans retinoic acid, Azacitidine, Azathioprine, Bevacizumab, Bexatotene, Bleomycin, Bortezomib, Carboplatin, Capecitabine, Cetuximab, Cisplatin, Chlorambucil, Cyclophosphamide, Cytarabine, Daunorubicin, Docetaxel, Doxifluridine, Doxorubicin, Epirubicin, Epothilone, Erlotinib, Etoposide, Fluorouracil, Gefitinib, Gemcitabine, Hydroxyurea, Idarubicin, Imatinib, Ipilimumab, Irinotecan, Mechlorethamine, Melphalan, Mercaptopurine, Methotrexate, Mitoxantrone, Ocrelizumab, Ofatumumab, Oxaliplatin, Paclitaxel, Panitumab, Pemetrexed, Rituximab, Tafluposide, Teniposide, Tioguanine, Topotecan, Tretinoin, Valrubicin, Vemurafenib, Vinblastine, Vincristine, Vindesine, Vinorelbine, Vorinostat, Romidepsin, 5-fluorouracil (5-FU), 6-mercaptopurine (6-MP), Cladribine, Clofarabine, Floxuridine, Fludarabine, Pentostatin, Mitomycin, ixabepilone, Estramustine, or a combination thereof.

"Clinically significant prostate cancer" as used herein refers to cases that have more than 50% chance to progress to lethal disease.

"Isolated" or "purified" large oncosomes as used herein refers to large oncosomes that are not in their natural milieu. No particular level of purification is required. For example, an isolated large oncosome may be removed from its native or natural environment.

"Large Oncosomes" and "Large extracellular vesicles" ("L-EV") are used interchangeably. As used herein they refer to tumor-derived microvesicles that transmit signaling complexes between cell and tissue compartments. They are distinct and different from small extracellular vesicles. Large oncosomes are about 1 μm to about 10 μm in size. In some embodiments, large oncosomes are shed by amoeboid tumor cells. Large oncosomes comprise lipids, nucleic acids and proteins, each or a combination of which may be used to detect and/or quantify large oncosomes. In various embodiments, the size of the large oncosomes may be about 1 μm to about 10 μm, 2 μm to about 10 μm, 3 μm to about 10 μm, 4 μm to about 10 μm, 5 μm to about 10 μm, 6 μm to about 10 μm, 7 μm to about 10 μm, 8 μm to about 10 μm or 9 μm to about 10 μm in size.

"Patient outcome" refers to whether a patient survives or dies as a result of treatment. A more accurate prognosis for patients as provided in this invention increases the chances of patient survival.

"Poor Prognosis" means that the prospect of survival and recovery of disease is unlikely despite the standard of care for the treatment of the cancer (for example, prostate cancer), that is, surgery, radiation, chemotherapy. Poor prognosis is the category of patients whose survival is less than that of the median survival.

"Good Prognosis" means that the prospect of survival and recovery of disease is likely with the standard of care for the treatment of the disease, for example, surgery, radiation, chemotherapy. Good prognosis is the category of patients whose survival is not less than that of the median survival.

A "recurrence" means that the cancer has returned after initial treatment.

"Non-recurrent" or "recurrence-free", as used herein means that the cancer is in remission; being recurrent means that the cancer is growing and/or has metastasized, and some surgery, therapeutic intervention, and/or cancer treatment is required to lower the chance of lethality. The "non-recurrent subjects" are subjects who have non-recurrent or recurrence-free disease, and they can be used as the control for recurrent subjects who have recurrent disease or recurrence.

"Subject" or "individual" or "animal" or "patient" or "mammal," is meant any subject, particularly a mammalian subject, for whom diagnosis, prognosis, or therapy is desired. In some embodiments, the subject has cancer. In some embodiments, the subject had cancer at some point in the subject's lifetime. In various embodiments, the subject's cancer is in remission, is recurrent or is non-recurrent.

"Mammal" as used herein refers to any member of the class Mammalia, including, without limitation, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; rodents such as mice, rats, hamsters and guinea pigs; and so on. In certain embodiments, the mammal is a human subject. The term does not denote a particular age or sex. Thus, adult and newborn subjects, as well as fetuses, whether male or female, are intended to be included within the scope of this term.

"Treatment" and "treating," as used herein refer to both therapeutic treatment and prophylactic or preventative measures, wherein the object is to prevent or slow down (lessen) the targeted pathologic condition, prevent the pathologic condition, pursue or obtain beneficial results, or lower the chances of the individual developing the condition even if the treatment is ultimately unsuccessful. Those in need of treatment include those already with the condition as well as those prone to have the condition or those in whom the condition is to be prevented. Examples of cancer treatment include, but are not limited to, active surveillance, observation, surgical intervention, chemotherapy, immunotherapy, radiation therapy (such as external beam radiation, stereotactic radiosurgery (gamma knife), and fractionated stereotactic radiotherapy (FSR)), focal therapy, systemic therapy, vaccine therapies, viral therapies, molecular targeted therapies, or a combination thereof.

"Tumor," as used herein refers to all neoplastic cell growth and proliferation, whether malignant or benign, and all pre-cancerous and cancerous cells and tissues.

"Tumor derived microvesicles (TMV)" or "microvesicles (MV)" as used herein refer to a mixture of exosomes, which are about 20 nm to about 80 nm in size, and large oncosomes which are about 1 μm to about 10 μm in size. "Oncosomes" as described in DiVizio et al, (Cancer Res. 2009, Vol 69(13) pages 5601-5609) refer to "microvesicles" and contain a mixture of cell-derived vesicles including but not limited to exosomes and large oncosomes. Microvesicles may also include shedding microvesicles, microparticles, nanovesicles, apoptotic bodies, nanoparticles and membrane vesicles.

"Therapeutic agents" as used herein refers to agents that are used to, for example, treat, inhibit, prevent, mitigate the effects of, reduce the severity of, reduce the likelihood of developing, slow the progression of and/or cure, a disease. Diseases targeted by the therapeutic agents include but are not limited to carcinomas, sarcomas, lymphomas, leukemia, germ cell tumors, blastomas, antigens expressed on various immune cells, and antigens expressed on cells associated with various hematologic diseases, autoimmune diseases, and/or inflammatory diseases.

Prostate cancer is frequently an indolent disease, and most of the patients die with prostate cancer but not of prostate cancer. Clinically significant prostate cancer are cases that can progress to lethal disease and kill the paptients. These are the type of prostate cancer that needs therapeutic intervention, and identifying them is important for treatment.

Described herein is one of the most comprehensive palmitoyl-proteomic studies to date and the first study to profile the palmitoyl-proteome of EVs. It was prompted by the observation that EVs are enriched in putative palmitoylated proteins in comparison to the cells of origin. Interestingly, the palmitoylated form of some proteins typically enriched in specific EV populations did not replicate the enrichment observed for the native form of the protein. This suggests an important role of palmitoylation in the sorting of cargo to different EV populations that would be missed if only the native protein is investigated. Further studies on the palmitoyl-proteome of EVs may identify mechanisms that could be exploited to target specific proteins to, or to deplete specific proteins from EVs.

The selective packaging of palmitoyl-proteins in EVs is also supported by the weak correlation between the palmitoyl-proteins identified in EVs and cell membranes. The differences between EVs and cells were more pronounced in the S-EVs than L-EVs, in line with a different origin of these vesicles from distinct intracellular compartments. Of note, our study described herein points to the association to different subcellular compartments of the palmitoyl-proteins enriched in EVs. Palmitoyl-proteins enriched in L-EVs associated primarily with the cytoplasm. Conversely, the palmitoyl-proteins enriched in S-EVs were mostly associated with the plasma membrane. This likely reflects that L-EVs are often generated as a result of membrane blebs inflated by the cytoplasm whereas the enrichment of the plasma membrane proteins in S-EVs may be explained by their high membrane/cytoplasm ratio. Comparative studies of the palmitoyl and total proteome of EVs will be essential to clarify the role of protein palmitoylation in the shuttling of proteins across different subcellular compartments and EV populations.

Attempts to identify disease proteins biomarkers from biological fluids have been hampered by the presence of high abundant proteins which severely masks detection of low abundance but physiologically important proteins. Because most abundant proteins are not palmitoylated, the LB-ABE may allow their drastic depletion from biofluids. The ABE chemistry can be applied to any type of biological samples as it does not rely on metabolic labelling. In addition to S-palmitoylated proteins, LB-ABE may also enrich for other PTMs (e.g. myristate and stearate) that are linked to cysteine residues via thioester bonds. Nevertheless, palmitoylation represents the most frequent S-acylation and the LB-ABE method has proved to largely eliminate the co-isolation of non-S-acylated proteins, thus representing a state-of-the-art discovery approach for large scale palmitoyl-protein profiling. The fact that 84% of the proteins identified have been previously identified as palmitoylated strongly supports the recovery of S-acylated proteins with high specificity. Moreover, out of the 330 proteins identified as palmitoylated for the first time, 65% have cysteines predicted to be palmitoylated with high confidence by bioinformatic tools, suggesting that they are genuine palmitoylated proteins. Taken together, these results support the use the LB-ABE for deep palmitoyl-proteomics with high specificity and sensitivity.

Given the altered palmitoylation in cancer and that palmitoylation targets proteins to EVs, the LB-ABE may allow for the detection of prostate cancer-relevant proteins in EVs. We found three proteins that are abundant in EVs (STEAP1, STEAP2 and ABCC4) and whose expression has been reported to be specific to prostate cancer. While STEAP1 was enriched in S-EVs, STEAP2 was found to be equally abundant in S- and L-EVs. The observation that STEAP2 participates in the intracellular vesicular transport machinery and associates with endocytic and exocytic pathways might explain its equal abundance in both L- and S-EVs. Of note, STEAP1 and ABCC4 were enriched in EVs in comparison to cells when we examined the total protein thus confirming the importance of interrogating the mechanisms of protein trafficking and cargo into EVs.

Interestingly, the loading of STEAP2 and ABCC4 into EVs was reduced by inhibition of palmitoylation. In contrast, 2-BP treatment did not alter the localization of other palmitoylated proteins such as Cav-1 in agreement with previous studies reporting that palmitoylation is not necessary for Cav-1 membrane localization. Of note, palmitoylation is essential for the protein localization into lipid rafts, which participate in the biogenesis of EVs. Therefore, STEAP2 and ABCC4 may require palmitoylation for their loading into EVs via association with lipid rafts. In contrast, Cav-1 association to lipid rafts derives from its high affinity to cholesterol rather than its palmitoylation status. Further studies will elucidate the role of palmitoylation in directing proteins towards distinct EV populations. Even though the role of palmitoylation in the subcellular localization and trafficking of proteins has been widely reported, the role of palmitoylation in EV transport is a novel field of study.

In summary, this is the first large-scale analysis of the palmitoyl-proteomes of L- and S-EVs. We show that: (1) the LB-ABE method enables the isolation of palmitoyl-proteins from intracellular compartments, as well as L- and S-EVs; (2) L- and S-EVs exhibit EV population-specific palmitoyl-profiles that reflect EV biological processes and subcellular origin and distinguish them from their parental cells; (3) prostate cancer-derived EVs contain cancer-specific palmi-toylated proteins; (4) palmitoylation may play a role in sorting and trafficking of proteins to EVs. Taken together, our results show that protein palmitoylation may be involved in the selective packaging of proteins to different EV populations and palmitoyl-proteomics may allow for better detection of disease biomarkers.

As such, various embodiments of the present invention are based, at least in part, on these findings.

Various embodiments of the present invention provide for a method of detecting one or more palmitoyl proteins, comprising: obtaining a biological sample from a subject having prostate cancer or suspected of having prostate cancer; isolating large extracellular vesicles (EVs) from the biological sample; assaying the large EVs for at least 10 palmitoyl proteins selected from the group consisting of GNAQ, CD9, TLN1, STX11, ITGB3, LYN, SLC4A1, CANX, FLOT2, FLOT1, ABHD16A, MYADM, ATP2A3, TMX1, RAP2B, ATP2A2, SLC2A3, RTN4, LTBP1, and ABCC4; and detecting the one or more palmitoyl proteins selected from the group consisting of GNAQ, CD9, TLN1, STX11, ITGB3, LYN, SLC4A1, CANX, FLOT2, FLOT1, ABHD16A, MYADM, ATP2A3, TMX1, RAP2B, ATP2A2, SLC2A3, RTN4, LTBP1, and ABCC4.

In various embodiments, the method comprises assaying the large EVs for at least 15 palmitoyl proteins. In various embodiments, the method comprises assaying the large EVs for all 20 palmitoyl proteins. In various embodiments, the method comprises assaying the large EVs for 11, 12, 13, 14, 15, 16, 17, 18, or 19 palmitoyl proteins. In various embodiments, the method comprises assaying the large EVs for 10-15 or 16-20 palmitoyl proteins.

In various embodiments, the method comprises detecting 2, 3, 4, 5, 6, 7, 8, 9, 10, 11, 12, 13, 14, 15, 16, 17, 18, 19 or all 20 palmitoyl proteins. In various embodiments, the method comprises detecting 1-5 of the palmitoyl proteins. In various embodiments, the method comprises detecting 6-10 of the palmitoyl proteins. In various embodiments, the method comprises detecting 11-15 of the palmitoyl proteins. In various embodiments, the method comprises detecting 16-20 of the palmitoyl proteins. In various embodiments, the method comprises detecting all 20 palmitoyl proteins.

In various embodiments, the method further comprises assaying for one or more additional palmitoyl proteins other than GNAQ, CD9, TLN1, STX11, ITGB3, LYN, SLC4A1, CANX, FLOT2, FLOT1, ABHD16A, MYADM, ATP2A3, TMX1, RAP2B, ATP2A2, SLC2A3, RTN4, LTBP1, and ABCC4. In various embodiments, the method further comprises assaying for 5, 10, 15, 20, 25, 30, 35, 40, 45 or 50 additional palmitoyl proteins other than GNAQ, CD9, TLN1, STX11, ITGB3, LYN, SLC4A1, CANX, FLOT2, FLOT1, ABHD16A, MYADM, ATP2A3, TMX1, RAP2B, ATP2A2, SLC2A3, RTN4, LTBP1, and ABCC4. In various embodiments, the method further comprises assaying for 50-60, 60-70, 70-80, 80-90, or 90-100 additional palmitoyl proteins other than GNAQ, CD9, TLN1, STX11, ITGB3, LYN, SLC4A1, CANX, FLOT2, FLOT1, ABHD16A, MYADM, ATP2A3, TMX1, RAP2B, ATP2A2, SLC2A3, RTN4, LTBP1, and ABCC4.

In various embodiments, the biological sample is blood plasma. In various embodiments, the biological sample is blood plasma. In various embodiments, the biological sample is whole blood or blood serum.

In various embodiments, the subject has prostate cancer. In various embodiments, the subject has metastatic prostate cancer.

Isolating the large oncosomes can be done as described herein. For example, cells are grown on cell culture plates until about 90% confluence, washed in PBS and serum-starved for about 24 hours before the collection of condi-tioned cell media. The conditioned media can be cleared by differential centrifugation of floating cells at about 300 g of cell debris at about 2,800 g for about 10 min, and spun in an ultracentrifuge at about 10,000 g for about 30 min (4° C., k-factor 2547.2) for the collection of L-EVs. 10,000 g pellets are then subjected to Optiprep™ (Sigma) density gradient purification. Fresh pelleted EVs are resuspended in 0.2 μm-filtered PBS and deposited at the bottom of an ultracen-trifuge tube. Next, about 30% (4.3 mL, 1.20 g/mL), about 25% (3 mL, 1.15 g/mL), 15% (2.5 mL, 1.10 g/mL), and 5% (6 mL, 1.08 g/mL) iodixanol solutions were sequentially layered at decreasing density to form a discontinuous gra-dient. Separation was performed by ultracentrifugation at 100,000 g for about 3 h 50 min (4° C., k-factor 254.7) and EV-enriched fractions collected either at about 1.10-1.15 g/mL for L-EVs. Purified EVs were then washed in PBS (100,000 g, 60 min, 4° C.) and resuspended in the appro-priate buffer. All ultracentrifugation spins were performed in a SW28 swinging rotor (Beckman Coulter).

In various embodiments, assaying for the at least 10 palmitoyl proteins comprises producing whole cell lysates of the large EVs and using a low-background acylbiotinyl exchange (LB-ABE) enrich the palmitoyl proteins. In vari-ous embodiments, assaying for the at least 10 palmitoyl proteins comprises digesting the palmitoyl proteins; for example, with trypsin, particularly, with MS-grade trypsin and using mass spectrometry to assay for the at least 10 palmitoyl proteins to detect one or more of those. For example, LC-MS/MS is used to assay for the palmitoyl proteins to detect one or more of those proteins.

In other embodiments, an antibody that binds specifically to the palmitoyl protein can be used to assay for the protein. For example, antibodies can be used to immunocapture via magnetic beads or other beads.

Further examples for detecting one or more of these palmitoyl proteins include but are not limited to flow cytom-etry, ELISA, and affinity purification.

Various embodiments of the invention provide a method of detecting clinically significant prostate cancer, compris-ing: obtaining a biological sample from a subject having prostate cancer or suspected of having prostate cancer; isolating large extracellular vesicles (EVs) from the biologi-cal sample; assaying the large EVs for at least 10 palmitoyl proteins selected from the group consisting of GNAQ, CD9, TLN1, STX11, ITGB3, LYN, SLC4A1, CANX, FLOT2, FLOT1, ABHD16A, MYADM, ATP2A3, TMX1, RAP2B, ATP2A2, SLC2A3, RTN4, LTBP1, and ABCC4; and detect-ing the one or more palmitoyl proteins selected from the group consisting of GNAQ, CD9, TLN1, STX11, ITGB3, LYN, SLC4A1, CANX, FLOT2, FLOT1, ABHD16A, MYADM, ATP2A3, TMX1, RAP2B, ATP2A2, SLC2A3, RTN4, LTBP1, and ABCC4, wherein the detection of the one or more palmitoyl proteins indicates the presence of clinically significant prostate cancer.

In various embodiments, the method comprises assaying the large EVs for at least 15 palmitoyl proteins. In various embodiments, the method comprises assaying the large EVs for all 20 palmitoyl proteins. In various embodiments, the method comprises assaying the large EVs for 11, 12, 13, 14, 15, 16, 17, 18, or 19 palmitoyl proteins. In various embodiments, the method comprises assaying the large EVs for 10-15 palmitoyl proteins or 16-20 palmitoyl proteins.

In various embodiments, the method comprises detecting 2, 3, 4, 5, 6, 7, 8, 9, 10, 11, 12, 13, 14, 15, 16, 17, 18, 19 or all 20 palmitoyl proteins. In various embodiments, the method comprises detecting 1-5 of the palmitoyl proteins. In various embodiments, the method comprises detecting 6-10 of the palmitoyl proteins. In various embodiments, the method comprises detecting 11-15 of the palmitoyl proteins. In various embodiments, the method comprises detecting 16-20 of the palmitoyl proteins. In various embodiments, the method comprises detecting all 20 palmitoyl proteins.

In various embodiments, the method further comprises assaying for one or more additional palmitoyl proteins other than GNAQ, CD9, TLN1, STX11, ITGB3, LYN, SLC4A1, CANX, FLOT2, FLOT1, ABHD16A, MYADM, ATP2A3, TMX1, RAP2B, ATP2A2, SLC2A3, RTN4, LTBP1, and ABCC4. In various embodiments, the method further comprises assaying for 5, 10, 15, 20, 25, 30, 35, 40, 45 or 50 additional palmitoyl proteins other than GNAQ, CD9, TLN1, STX11, ITGB3, LYN, SLC4A1, CANX, FLOT2, FLOT1, ABHD16A, MYADM, ATP2A3, TMX1, RAP2B, ATP2A2, SLC2A3, RTN4, LTBP1, and ABCC4. In various embodiments, the method further comprises assaying for 50-60, 60-70, 70-80, 80-90, or 90-100 additional palmitoyl proteins other than GNAQ, CD9, TLN1, STX11, LYN, SLC4A1, CANX, FLOT2, FLOT1, ABHD16A, MYADM, ATP2A3, TMX1, RAP2B, ATP2A2, SLC2A3, RTN4, LTBP1, and ABCC4.

In various embodiments, the biological sample is blood plasma. In various embodiments, the biological sample is whole blood or blood serum.

In various embodiments, the subject has prostate cancer. In various embodiments, the subject has metastatic prostate cancer.

Isolating the large EVs can be done as described above and herein.

In various embodiments, assaying for the at least 10 palmitoyl proteins comprises a low-background acylbiotinyl exchange (LB-ABE) enrich the palmitoyl proteins. In various embodiments, detecting the at least 10 palmitoyl proteins comprises digesting the palmitoyl proteins; for example, with trypsin, particularly, with MS-grade trypsin and using mass spectrometry to assay the at least 10 palmitoyl proteins and detect one or more of those proteins. For example, LC-MS/MS is used to assay the palmitoyl proteins and detect one or more of those proteins.

Various embodiments provide for an assay kit, comprising: a reagent to isolate large EVs from a biological sample; and a reagent to immobilize the large oncosomes. In various embodiments, the reagent to isolate the large EVs comprises magnetic bead conjugated with antibodies that binds specifically to the large EVs. In various embodiments, the kit further comprises an enzyme to digest palmitoyl proteins isolated from the large oncosomes into peptide fragments.

Thereafter, MS can be used to assay the digested proteins (i.e., peptide fragments) and detect one ore more of those proteins.

In various embodiments, the assay kit further comprises 10 or more antibodies, each of which specifically binds to a different palmitoyl protein selected from the group consisting of GNAQ, CD9, TLN1, STX11, ITGB3, LYN, SLC4A1, CANX, FLOT2, FLOT1, ABHD16A, MYADM, ATP2A3, TMX1, RAP2B, ATP2A2, SLC2A3, RTN4, LTBP1, and ABCC4. That is there are at least 10 different antibodies for 10 different palmitoyl proteins in the aforementioned group. In various embodiments, the assay further comprises 11, 12, 13, 14, 15, 16, 17, 18, 19 or 20 antibodies, each of which specifically binds to a different palmitoyl protein selected from the group consisting of GNAQ, CD9, TLN1, STX11, ITGB3, LYN, SLC4A1, CANX, FLOT2, FLOT1, ABHD16A, MYADM, ATP2A3, TMX1, RAP2B, ATP2A2, SLC2A3, RTN4, LTBP1, and ABCC4. That is there are 11, 12, 13, 14, 15, 16, 17, 18, 19 or 20 antibodies for the 11, 12, 13, 14, 15, 16, 17, 18, 19 or 20 different palmitoyl proteins, respectively, in the aforementioned group.

Large oncosomes are tumor-derived microvesicles that transmit signaling complexes between cell and tissue compartments. Herein, the inventors show that amoeboid tumor cells export large oncosome (1-10 μm diameter) vesicles, derived from bulky cellular protrusions, which contain metalloproteinases, RNA, proteins (for example, caveolin-1 (Cav-1) and the GTPase ARF6), and are biologically active toward tumor cells, endothelial cells and fibroblasts. The inventors also describe methods whereby large oncosomes can be selectively sorted by flow cytometry and analyzed independently of vesicles smaller than 1 μm. Large oncosomes were identified in the circulation of different mouse models of prostate cancer and their abundance correlated with tumor progression. Similar large vesicles were also identified in human tumor tissues, but they were not detected in the benign compartment. They were more abundant in metastases.

Accordingly, some embodiments of the invention are based, at least in part, on the finding that large oncosomes can be visualized and quantified in biological samples (for example, in tissues and in circulation), and isolated and characterized using clinically-adaptable methods. These findings also suggest a mechanism whereby migrating tumor cells condition the tumor microenvironment and distant sites, thereby potentiating advanced disease. The present invention addresses the need for determining the likelihood of cancer metastasis and prognostication of cancer, such as prostate cancer. The invention provides assays and methods for isolating large oncosomes, determining the likelihood of cancer metastasis based on the number and/or molecular content of the large oncosomes and for treating cancer in subjects based on the number and/or molecular content of large oncosomes. In an embodiment, the cancer is prostate cancer.

Figure 10:
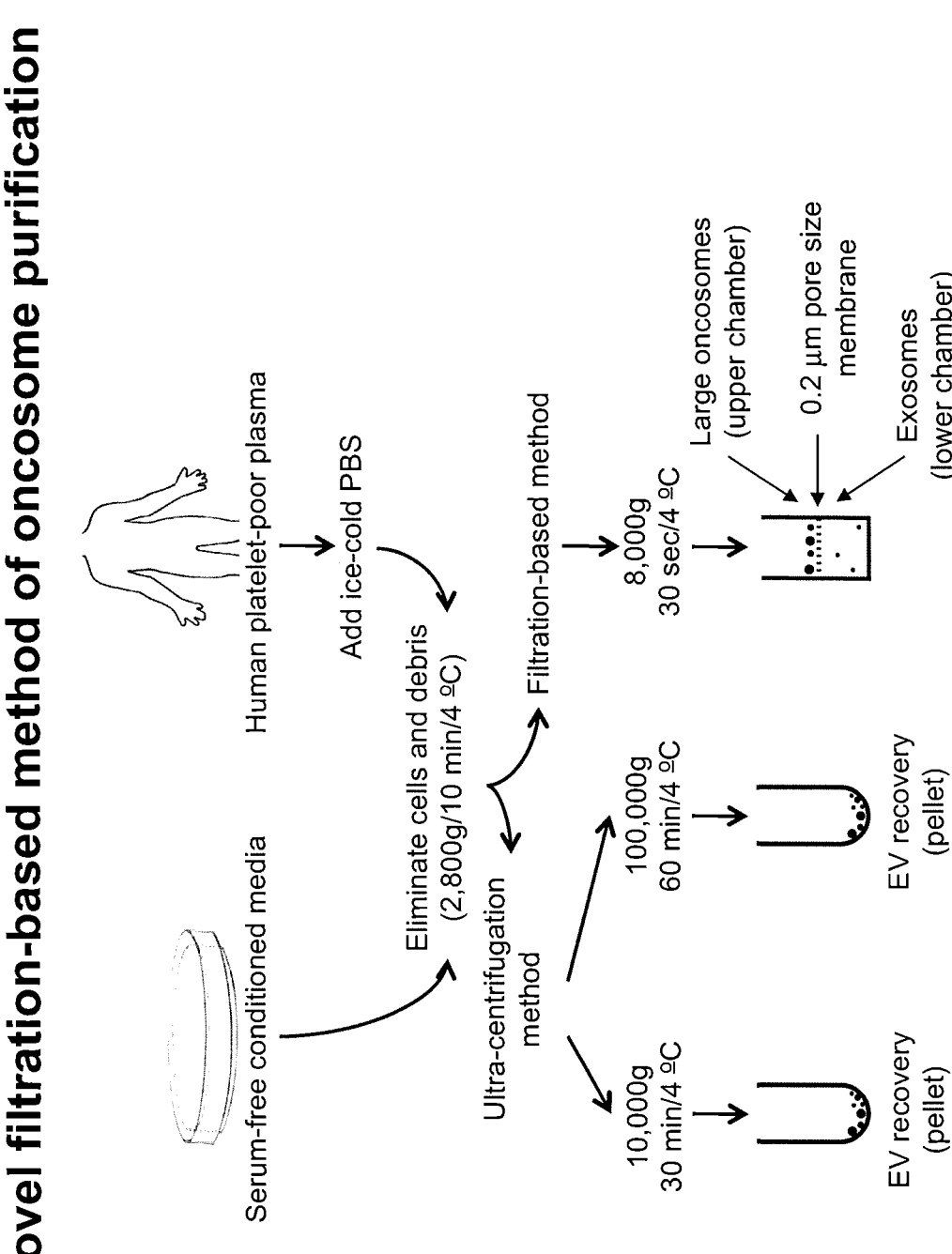
FIG. 10 depicts, in accordance with an embodiment of the invention the filtration-based isolation protocol.

Specifically, provided herein is a process comprising obtaining a biological sample from a subject that has or previously had cancer (for example, prostate cancer), processing the sample to obtain platelet-poor plasma, optionally further centrifuging the platelet-poor plasma to eliminate cells and cellular debris, filtering the supernatant using a filter with an appropriate pore size to separate large oncosomes from other microvesicles and collecting the large oncosomes. In an embodiment, the large oncosomes may be in the upper chamber of the filtration unit and the exosomes and/or other microvesicles may be in the lower chamber of the filtration unit. An embodiment of the process is depicted in FIG. 10.

In an embodiment, the invention provides a method for isolating large oncosomes from a blood sample obtained from a subject that has or previously had cancer. In an embodiment, the cancer is prostate cancer. The method includes processing the blood sample obtained from the subject to obtain platelet-poor plasma and optionally further eliminating cells and cellular debris (for example by centrifugation). The platelet-poor plasma is filtered using a filter with an appropriate pore size to separate large oncosomes from other microvesicles and the large oncosomes are collected. In an embodiment, the large oncosomes may be in the upper chamber of the filtration unit and the exosomes and/or other microvesicles may be in the lower chamber of the filtration unit. The filtration-based method for purifying large oncosomes is depicted in FIG. 10.

In an embodiment, the invention provides a method for isolating large oncosomes from a blood sample obtained from a subject that has or previously had prostate cancer. The method includes processing the blood sample obtained from the subject to obtain platelet-poor plasma and optionally further centrifuging the platelet-poor plasma at 2800 g for 10 minutes at 4° C. so as to eliminate and cells and cellular debris. The supernatant is filtered using a filter with a 0.2 μm pore size as depicted in FIG. 10 and the large oncosomes are collected. The large oncosomes may be collected from the upper chamber of the filtration unit.

For the filtration-based method described herein to isolate the large oncosomes also described herein, the type and size of filters and columns that may be used will be apparent to a person of skill in the art. For example, centrifugal ultracentrifugation devices covering sample volumes from 500 μl to 2 ml with any type of low-protein retentions and wide pH-range (e.g. 2-12 pH) filter membranes, such as polyethersulfone (PES) can be used. The nominal size of the pores can range between any one or more of 0.1 μm to 1 μm, 0.2 μm to 1 μm, 0.3 μm to 1 μm, 0.4 μm to 1 μm, 0.5 μm to 1 μm, 0.6 μm to 1 μm, 0.7 μm to 1 μm, 0.8 μm to 1 μm or 0.9 μm to 1 μm.

The pore size of the filter is selected so as to enrich for large oncosomes, wherein enriching for large oncosomes comprises obtaining a greater number of large oncosomes relative to other microvesicles. For example, to separate the large oncosomes from other microvesicles such as exosomes, the pore size of the filter may be any of 200 nm, 300 nm, 400 nm, 500 nm, 600 nm, 700 nm or 800 nm. In an embodiment, the pore size is 200 nm.

In various embodiments, large oncosomes are purified or enriched-for, if after filtration, the yield is about 100% large oncosomes, 90% large oncosomes, 80% large oncosomes, 70% larger oncosomes, 60% large oncosomes or 55% large oncosomes.

Methods for obtaining platelet-poor plasma will be apparent to a person of skill in the art. For example, platelet-poor plasma may be obtained by the methods described in Floryan, K. and Berghoff, W. (*AORN Journal* October 2004, Vol 80(4), pages 667-674) and/or Cai et al. (*Int J Radiat Oncol Biol Phys* 2010 Vol 77(3), pages 867-76).

Provided herein are methods for identifying large oncosomes in a tissue sample. The method includes providing a tissue sample from the subject, fixing and embedding the tissue (for example, formalin fixing and paraffin embedding tissue) and staining the tissue sample, wherein large oncosomes are identified as large membrane sacs attached to and surrounding the cells. In some embodiments, the tissue is stained with any one or more of hematoxylin and eosin (H&E), Alizarin red S (ARS), Periodic acid-Schiff (PAS), Masson's trichrome, Romanowsky stains, Silver stain, Sudan stain, or a combination thereof. In various embodiments, staining the tissue sample encompasses contacting the embedded tissue sample with reagents that react with any one or more of lipids, proteins, DNA, RNA or a combination thereof present in the large oncosomes. The reagent may be any one or more of a nucleic acid, an antibody, a small molecule, a lipid or a combination thereof. In some embodiments, the sample is contacted with a label to produce a signal so as to detect any one or more of proteins, DNA, RNA or a combination thereof present in the large oncosomes. In exemplary embodiments, the tissue is stained for any one or more of cytokeratins, PSA, PMSA, Cav-1, MCL2, membrane proteins, lipids, carbohydrates or a combination thereof.

Also provided herein are methods for determining the likelihood of cancer metastasis in a subject in need thereof. The method includes providing a sample from a subject that has or previously had cancer and detecting large oncosomes in the sample. If the sample is a tissue sample, the method comprises detecting large oncosomes by staining the tissue, wherein the large oncosomes may be identified as large membrane sacs attached to and surrounding the cells. If the sample is a blood sample, the method comprises isolating large oncosomes by the methods described herein and quantifying the isolated large oncosomes. In various embodiments, the subject has an increased likelihood of cancer metastasis if there is an increase in the number of large oncosomes in the sample from the subject relative to a reference sample, or the subject has a decreased likelihood of cancer metastasis if the number of large oncosomes in the sample from the subject is the same as or decreased relative to the reference sample.

Further provided are methods for determining the likelihood of prostate cancer metastasis in a subject in need thereof. The method includes providing a blood sample from a subject that has or previously had prostate cancer, detecting large oncosomes in the blood sample by isolating large oncosomes according to the methods described herein and subsequently, quantifying the isolated large oncosomes, and determining that the subject has an increased likelihood of prostate cancer metastasis if there is an increase in the number of large oncosomes in the sample from the subject relative to a reference sample, or determining that the subject has a decreased likelihood of prostate cancer metastasis if the number of large oncosomes in the sample from the subject is the same as or decreased relative to the reference sample, so as to determine the likelihood of cancer metastasis in the subject.

Also provided are methods for determining the likelihood of cancer metastasis (for example, prostate cancer metastasis) in a subject in need thereof. The method includes providing a tissue sample from a subject that has or previously had cancer (for example, prostate cancer), detecting large oncosomes in the tissue sample by identifying large oncosomes attached to the cells in the sample or not-attached but surrounding the cells in the sample and determining that the subject has an increased likelihood of cancer metastasis (for example, prostate cancer metastasis) if large oncosomes are present and/or there is an increase in the number of large oncosomes in the sample from the subject relative to a reference sample, or determining that the subject has a decreased likelihood of cancer metastasis (for example, prostate cancer metastasis) if large oncosomes are absent and/or there is a decrease in the number of large oncosomes in the sample from the subject relative to the reference sample, so as to determine the likelihood of cancer metastasis in the subject. In an embodiment, the tissue sample is a prostate tissue sample. In another embodiment, the tissue sample is a sample from any other organ suspected of being cancerous.

The invention also provides methods for treating cancer (for example, prostate cancer) in a subject in need thereof. The method comprises providing a biological sample from the subject, isolating and/or detecting large oncosomes in the sample from the subject by the methods described herein, determining the likelihood of cancer metastasis in the subject by the methods described herein and prescribing a therapy and optionally administering the therapy to the subject if the subject has an increased likelihood of cancer metastasis. In some embodiments, the sample is blood or tissue. In an embodiment, the subject has an increased likelihood of cancer metastasis if large oncosomes are present or if there is an increase in the number of large oncosomes in the sample from the subject relative to a reference sample.

In various embodiments, the samples for use with the methods and processes described herein are obtained from human subjects that have cancer or have had cancer. In an embodiment, the cancer is prostate cancer. In various embodiments, the sample is any one or more of blood, plasma, tissue, urine or a combination thereof.

Detection of Large Oncosomes

As described herein, the determination of likelihood of cancer metastasis (for example, prostate cancer metastasis) in a subject and/or treatment of cancer in a subject (for example, prostate cancer and/or prostate cancer related metastasis) includes detecting and/or quantifying large oncosomes in samples obtained from the subject. In various embodiments, the samples are blood, tissue or a combination thereof.

Further, as described herein, large oncosomes comprise lipids, nucleic acid and proteins (molecular content), each of which or a combination thereof may be used to not only detect and/or quantify large oncosomes but may also be used to identify the type of cancer that may be metastasizing.

The nucleic acid component of the molecular content of large oncosomes includes DNA and/or variants thereof such as single-stranded DNA (ssDNA), double-stranded DNA (dsDNA), cDNA and/or genomic DNA. The nucleic acid component of the molecular content of large oncosomes also includes RNA and its variants including but not limited to mRNA, rRNA, tRNA, siRNA, miRNA and/or non-coding RNA. The nucleic acid component of the molecular content of large oncosomes also includes tandem repeats (such as satellite DNA/RNA, microsatellite DNA/RNA or minisatellite DNA/RNA), interspersed repeats (such as transposons (transposable elements), Short Interspersed Nuclear Elements (SINEs, such as Alu's), Long Interspersed Nuclear Elements (LINEs such LINE-1), global direct repeats, local direct simple repeats, local direct repeats, local direct repeats with spacer and/or endogenous retroviruses (endogenous viral elements). Examples of nucleic acids that may be found in the large oncosomes are shown in Table 1. Examples of microRNAs that may be found in large oncosomes are shown in Table 2.

The protein component of the molecular content of the large oncosomes includes peptides, polypeptides and/or variants thereof. As described herein, the presence of large oncosomes in a sample is indicative of increased likelihood of cancer metastasis. In some exemplary embodiments, the presence of PSA or the presence of Caveolin-1 in the large oncosomes from the subject may be indicative of prostate cancer metastasis or the presence of Arf6 in the large oncosomes may be indicative of breast cancer metastasis or the presence of both PSA and Arf6 may be indicative of prostate cancer metastasis. Other proteins present in large oncosomes may also be indicative of various cancer metastasis, including prostate cancer metastasis.

Polypeptides may be modified or unmodified. Modifications to the polypeptides include but are not limited to any one or more of myristoylation, palmitoylation, prenylation, farnesylation, geranylgeranylation, glypiation, glycosylphosphatidylinositol (GPI) lipoylation, addition of flavin moiety (FMN or FAD), addition of heme C, phosphopantetheinylation, diphthamide formation, addition of ethanolamine phosphoglycerol, hypusine formation, acylation, alkylation, amide bond formation, butyrylation, gamma-carboxylation, glycosylation, hydroxylysine, polysialylation, malonylation, hydroxylation, iodination, nucleotide addition (such as ADP-ribosylation), oxidation, phosphate ester (O-linked) or phosphoramidate (N-linked) formation, phosphorylation, adenylylation, propionylation, pyroglutamate formation, S-glutathionylation, S-nitrosylation, Succinylation, sulfation, selenoylation, ISGylation, SUMOylation, ubiquitination, Neddylation, Pupylation, citrullination, deamidation, eliminylation, carbamylation, disulfide bridges formation, proteolytic cleavage, racemization or a combination thereof.

The lipid component of the molecular content of the large oncosomes includes but is not limited to any one or more of fatty acids, glycerolipids, glycerophospholipids, sphingolipids, sterol lipids, prenol lipids, saccharolipids, polyketides, phosphoglycerides, glycolipids, or a combination thereof.

Large oncosomes may be isolated from biological material including but not limited to any one or more of tissue, cells, blood, plasma, serum, urine, sputum, spinal fluid, pleural fluid, nipple aspirate, lymph fluid, fluid of the respiratory tract, fluid of the intestinal tract, fluid of the genitourinary tract, fluid of the lymphatic system, semen, cerebrospinal fluid, tears, saliva, intra-organ system fluid, tumor cyst fluid, amniotic fluid or a combination thereof.

In some embodiments, large oncosomes are purified from a sample obtained from a subject and detected and/or quantified without labeling the large oncosomes. In an embodiment, unlabeled large oncosomes may be quantified using flow cytometry techniques, for example, using forward scatter flow cytometry. In an embodiment, forward scatter flow cytometry is used with 1 μm to 10 μm beads to enrich for detection large oncosomes. Methods for performing forward scatter flow cytometry would be apparent to a person of skill in the art and may be performed as described in, for example, Di Vizio et al. (*Cell Cycle*. 2009 August; 8(15):2420-4), Dragovic et al. (*Nanomedicine*. 2011 December; 7(6):780-8), Wysoczynski M and Ratajczak M Z (*Int J Cancer*. 2009 Oct. 1; 125(7):1595-603). Broadly, flow cytometry analysis of large oncosomes may be performed by setting forward scatter (FSC) and side scatter (SSC) voltages as low as that the background noise, determined by running double 0.2 μm filtered PBS at the highest flow rate available (in some embodiments, no higher that 0-4 events/second. After data acquisition, large oncosomes can be analyzed by setting FSC and SSC on a logarithmic scale.

In some embodiments, the isolated/purified large oncosomes obtained from a sample from a subject may be labeled and then quantified and/or detected. In such instances, the nucleic acids, lipids and/or proteins in the large oncosomes are labeled. In an embodiment, flow cytometry is used to detect and quantify the labeled large oncosomes. In an embodiment, large oncosomes are labeled with antibodies that bind to specific proteins of interest. For example, in order to detect and/or quantify large oncosomes obtained from a subject that has or had prostate cancer, the isolated large oncosomes may be labeled with antibodies that bind antigens including but not limited to PSA, PMSA, PSMA, FASN, Cav-1 or a combination thereof. In an embodiment, the large oncosomes labeled with antibodies are detected and/or quantified using flow cytometry.

In some embodiments, the labeled large oncosomes may be detected using microfluidic systems as described in Shao et al. (*Nature Medicine December* 2012 Vol 18(12) pages 1835-1841). The methods described in Shao et al. are applied to exosomes but as would be apparent to a person of skill in the art, these methods may be applied to large oncosomes as well. The larger size of the large oncosomes may facilitate better capture of the large oncosomes.

In further embodiments, the isolated/purified large oncosomes may be denatured and the denatured material may be used as an analyte to detect the presence of one or more proteins of interest in the large oncosomes. For example, specific antibodies may be used to detect the presence of one or more proteins of interest. Any suitable immunoassay method may be utilized, including those which are commercially available, to ascertain the presence of, and optionally quantify the amount of, the protein of interest present in the analyte. The presence (and optionally the amount) of the protein of interest in the analyte is indicative of the presence of said protein in large oncosomes. In various embodiments, the proteins of interest may be the cancer specific markers, including but not limited to the markers described herein. In various embodiments, the antibody is any one or more of a monoclonal antibody or fragment thereof, a polyclonal antibody or a fragment thereof, chimeric antibodies, humanized antibodies, human antibodies, and a single chain antibody. Extensive discussion of the known immunoassay techniques is not required here since these are known to those of skill in the art. Typical suitable immunoassay techniques include Western blots, sandwich enzyme-linked immunoassays (ELISA), radioimmunoassays (RIA), competitive binding assays, homogeneous assays, heterogeneous assays, etc. Various known immunoassay methods are reviewed, e.g., in Methods in Enzymology, 70, pp. 30-70 and 166-198 (1980).

Further, "sandwich-type" assays may be used with the methods described herein. Some examples of sandwich-type assays are described in U.S. Pat. Nos. 4,168,146 and 4,366, 241. Alternatively, "competitive-type" assays may be used with the methods described herein. In a competitive assay, the labeled probe is generally conjugated with a molecule that is identical to, or an analog of, the analyte. Thus, the labeled probe competes with the analyte of interest for the available receptive material. Competitive assays are typically used for detection of analytes such as haptens, each hapten being monovalent and capable of binding only one antibody molecule. Examples of competitive immunoassay devices are described in U.S. Pat. Nos. 4,235,601, 4,442,204 and 5,208,535.

Antibodies, that may be used to detect one or more proteins of interest in a large oncosome, may be labeled. In some embodiments, the detection antibody is labeled by covalently linking to an enzyme, labeled with a fluorescent compound or metal or is labeled with a chemiluminescent compound. For example, the detection antibody can be labeled with catalase and the conversion uses a colorimetric substrate composition comprises potassium iodide, hydrogen peroxide and sodium thiosulphate; the enzyme can be alcohol dehydrogenase and the conversion uses a colorimetric substrate composition comprises an alcohol, a pH indicator and a pH buffer, wherein the pH indicator is neutral red and the pH buffer is glycine-sodium hydroxide; the enzyme can also be hypoxanthine oxidase and the conversion uses a colorimetric substrate composition comprises xanthine, a tetrazolium salt and 4,5-dihydroxy-1,3-benzene disulphonic acid. In one embodiment, the detection antibody is labeled by covalently linking to an enzyme, label with a fluorescent compound or metal, or label with a chemiluminescent compound.

Direct and indirect labels can be used in immunoassays. A direct label can be defined as an entity, which in its natural state, is visible either to the naked eye or with the aid of an optical filter and/or applied stimulation, e.g., ultraviolet light, to promote fluorescence. Examples of colored labels which can be used include metallic sol particles, gold sol particles, dye sol particles, dyed latex particles or dyes encapsulated in liposomes. Other direct labels include radionuclides and fluorescent or luminescent moieties. Indirect labels such as enzymes can also be used according to the invention. Various enzymes are known for use as labels such as, for example, alkaline phosphatase, horseradish peroxidase, lysozyme, glucose-6-phosphate dehydrogenase, lactate dehydrogenase and urease. For a detailed discussion of enzymes in immunoassays see Engvall, Enzyme Immunoassay ELISA and EMIT, Methods of Enzymology, 70, 419-439 (1980).

The antibody can be attached to a surface. Examples of useful surfaces on which the antibody can be attached for the purposes of detecting the desired antigen include nitrocellulose, PVDF, polystyrene, and nylon. The surface or support may also be a porous support (see, e.g., U.S. Pat. No. 7,939,342). The assays can be carried out in various assay device formats including those described in U.S. Pat. Nos. 4,906,439; 5,051,237 and 5,147,609 to PB Diagnostic Systems, Inc.

In some embodiments of the processes and methods described herein, detecting the presence and/or level of antibodies reactive to cancer specific markers (for examples, cancer specific proteins) present in large oncosomes includes contacting the isolated large oncosomes from the cancer patient with an antibody or a fragment thereof that specifically binds to the cancer specific marker of interest, forming an antibody-protein complex between the antibody and marker present in the sample, washing the sample to remove the unbound antibody, adding a detection antibody that is labeled and is reactive to the antibody bound to marker in the sample, washing to remove the unbound labeled detection antibody and converting the label to a detectable signal, wherein the detectable signal is indicative of the presence and/or level of the cancer specific marker in the sample from the patient. In some embodiments, the effector component is a detectable moiety selected from the group consisting of a fluorescent label, a radioactive compound, an enzyme, a substrate, an epitope tag, electron-dense reagent, biotin, digonigenin, hapten and a combination thereof. In some embodiments, the detection antibody is labeled by covalently linking to an enzyme, labeled with a fluorescent compound or metal, labeled with a chemiluminescent compound. The level of the marker may be obtained by measuring a light scattering intensity resulting from the formation of an antibody-protein complex formed by a reaction of marker in the sample with the antibody, wherein the light scattering intensity of at least 10% above a control light scattering intensity indicates the likelihood of presence of the cancer specific marker and thereby, presence of large oncosomes in the sample and increased likelihood of cancer metastasis in the subject.

In some embodiments, the isolated/purified large oncosomes obtained from a sample from a subject may be labeled and then quantified and/or detected. In such instances, the nucleic acids, lipids and/or proteins in the large oncosomes are labeled. In some embodiments, the nucleic acids are labeled. For example, mRNA encoding PSA, PMSA, Cav-1 or a combination thereof may be detected with a polynucleotide capable of hybridizing with PSA specific mRNA, PMSA specific mRNA and/or Cav-1 specific mRNA, under stringent hybridization conditions. In various embodiments, micro RNA (miRNA) may also be used to detect and/or quantify large oncosomes. In some embodiments, some miRNAs such as miR-31, miR-145, miR-18a, miR-135a, which have been shown to be de-regulated in various types of cancers including bladder, prostate, breast, and colorectal cancer, may be markers for specific types of cancers may be markers for specific types of cancers. In certain embodiments, the RNA (for example, mRNA or miRNA) expression level is determined using microarray, SAGE, blotting, RT-PCR, quantitative PCR or qPCR.

Techniques that may be used to assess the amount of nucleic acid encoding cancer-specific marker of interest present in the large oncosomes isolated from a sample obtained from a subject include but are not limited to in situ hybridization (e.g., Angerer (1987) *Meth. Enzymol* 152: 649). Preferred hybridization-based assays include, but are not limited to, traditional "direct probe" methods such as Southern blots or in situ hybridization (e.g., FISH and FISH plus SKY), and "comparative probe" methods such as comparative genomic hybridization (CGH), e.g., cDNA-based or oligonucleotide-based CGH. The methods can be used in a wide variety of formats including, but not limited to, substrate (e.g. membrane or glass) bound methods or array-based approaches. Probes that may be used for nucleic acid analysis are typically labeled, e.g., with radioisotopes or fluorescent reporters. Preferred probes are sufficiently long so as to specifically hybridize with the target nucleic acid(s) under stringent conditions. The preferred size range is from about 200 bases to about 1000 bases. Hybridization protocols suitable for use with the methods of the invention are described, e.g., in Albertson (1984) *EMBO J.* 3: 1227-1234; Pinkel (1988) *Proc. Natl. Acad. Sci. USA* 85: 9138-9142; EPO Pub. No. 430,402; Methods in Molecular Biology, Vol. 33: In situ Hybridization Protocols, Choo, ed., Humana Press, Totowa, N.J. (1994), Pinkel, et al. (1998) *Nature Genetics* 20: 207-211, and/or Kallioniemi (1992) *Proc. Natl Acad Sci USA* 89:5321-5325 (1992).

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided in Innis, et al. (1990) PCR Protocols, *A Guide to Methods and Applications*, Academic Press, Inc. N.Y.). Measurement of DNA copy number at microsatellite loci using quantitative PCR analysis is described in Ginzonger, et al. (2000) *Cancer Research* 60:5405-5409. The known nucleic acid sequence for the genes is sufficient to enable one of skill in the art to routinely select primers to amplify any portion of the gene. Fluorogenic quantitative PCR may also be used in the methods of the invention. In fluorogenic quantitative PCR, quantitation is based on amount of fluorescence signals, e.g., TaqMan and sybr green.

Other suitable amplification methods include, but are not limited to, ligase chain reaction (LCR) (see Wu and Wallace (1989) *Genomics* 4: 560, Landegren, et al. (1988) *Science* 241:1077, and Barringer et al. (1990) *Gene* 89: 117), transcription amplification (Kwoh, et al. (1989) *Proc. Nat. Acad. Sci. USA* 86: 1173), self-sustained sequence replication (Guatelli, et al. (1990) *Proc. Nat. Acad. Sci. USA* 87: 1874), dot PCR, and linker adapter PCR, etc.

In certain embodiments, other techniques may be used to determine expression of a polynucleotide gene product, including microarray analysis (Han, M., et al., Nat Biotechnol, 19: 631-635, 2001; Bao, P., et al., Anal Chem, 74: 1792-1797, 2002; Schena et al., Proc. Natl. Acad. Sci. USA 93:10614-19, 1996; and Heller et al., Proc. Natl. Acad. Sci. USA 94:2150-55, 1997) and SAGE (serial analysis of gene expression). Like MPSS, SAGE is digital and can generate a large number of signature sequences. (see e.g., Velculescu, V. E., et al., Trends Genet, 16: 423-425., 2000; Tuteja R. and Tuteja N. Bioessays. 2004 August; 26(8):916-22), although orders of magnitude fewer than that are available from techniques such as MPSS.

In certain embodiments, the term "microarray" includes a "nucleic acid microarray" having a substrate-bound plurality of nucleic acids, hybridization to each of the plurality of bound nucleic acids being separately detectable. The substrate can be solid or porous, planar or non-planar, unitary or distributed. Nucleic acid microarrays include all the devices so called in Schena (ed.), DNA Microarrays: A Practical Approach (Practical Approach Series), Oxford University Press (1999); Nature Genet. 21(1) (suppl.): 1-60 (1999); Schena (ed.), Microarray Biochip: Tools and Technology, Eaton Publishing Company/BioTechniques Books Division (2000). Nucleic acid microarrays may include a substrate-bound plurality of nucleic acids in which the plurality of nucleic acids are disposed on a plurality of beads, rather than on a unitary planar substrate, as described, for example, in Brenner et al., Proc. Natl. Acad. Sci. USA 97(4): 1665-1670 (2000). Examples of nucleic acid microarrays may be found in, for example, U.S. Pat. Nos. 6,391,623, 6,383,754, 6,383, 749, 6,380,377, 6,379,897, 6,376,191, 6,372,431, 6,351,712 6,344,316, 6,316,193, 6,312,906, 6,309,828, 6,309,824, 6,306,643, 6,300,063.

In further embodiments, the large oncosomes isolated from samples (for example, tissue, blood, plasma or a combination thereof) may be identified by detecting cancer specific (also referred to herein as cancer-specific) markers including but not limited to any one or more of cytokeratins (for example basic or neutral cytokeratins (including CK1, CK2, CK3, CK4, CK5, CK6, CK7, CK8 and CK9) and/or acidic cytokeratins (CK10, CK12, CK 13, CK14, CK16, CK17, CK18, CK19 and CK20)), prostate-specific antigen (PSA), prostate-specific membrane antigen (PSMA), caveolin-1 (Cav-1), MCL2, bladder-tumor antigen (BTA), NMP22, carcinoembryonic antigen (CEA), CA 125, CA 19-9, TPA, hormone receptors (for example estrogen and progesterone), HER2/neu antigen, CA15-3, CEA, CA27-29, bcr-abl, CA19-9, EGFR, human chorionic gonadotropin (HCG), alpha fetoprotein (AFP), neuron-specific enolase (NSE), epidermal growth factor receptor (EGFR), TA-90, S-100, immunoglobulins or free light chains, Bence Jones proteins, monoclonal protein (M-protein), CA 125, CA 72-4, LASA-P, HCG, CA 72-4, Lactate dehydrogenase (LDH), FASN or a combination thereof. Additional cancer specific markers include proteins encoded by genes set forth in Table 1. In various embodiments, the aforementioned markers may be detected in the isolated/purified large oncosomes by detecting the nucleic acids that encode the aforementioned cancer-specific markers or by detecting the proteins that encode the aforementioned cancer-specific markers.

Suitable methods for assaying for the expression of various cancer-specific markers present in isolated large oncosomes (for example, non-denatured large oncosomes or denatured large oncosomes) isolated from samples obtained from subjects include but are not limited to any one or more of DNA sequencing, comparative genomic hybridization (CGH), array CGH (aCGH), SNP analysis, mRNA expression assay, RT-PCR, real-time PCR, or a combination thereof. In various embodiments, the assay for detection of nucleic acids encoding cancer-specific markers or protein levels of cancer-specific markers present in the isolated large oncosomes include any one or more of Northern blot analysis, Southern blot analysis, reverse transcription-polymerase chain reaction (RT-PCR), polymerase chain reaction (PCR), enzyme-linked immunosorbent assay (ELISA), radio-immuno assay (RIA), sodium dodecyl sulfate polyacrylamide gel electrophoresis (SDS-PAGE), Western blot analysis, mass spectrometry immune assays (MSIA), stable isotope standard capture with anti-peptide antibodies (SISCAPA), two-dimensional electrophoresis, PROTOMAP, which combines SDS-PAGE with shotgun proteomics, matrix-assisted laser desorption/ionization (MALDI), fast parallel proteolysis (FASTpp), yeast two-hybrid analysis, protein microarrays, immunoaffinity chromatography, immunoaffinity chromatography followed by mass spectrometry, dual polarization interferometry, microscale thermophoresis, phage display method, stable isotope labeling by amino acids in cell culture (SILAC) or a combination thereof. In some embodiments, the presence of cancer-specific markers in isolated large oncosomes may be ascertained by measuring the substrate upon which the marker may act, such that the substrate serves as a surrogate marker for the cancer specific marker.

In various embodiments, tissue samples obtained from subject with cancer (for example, prostate cancer), may be analyzed for large oncosomes. Large oncosomes in the tissue sample may be identified by staining the tissue using any one or more of hematoxylin and eosin (H&E) stain, Periodic acid-Schiff (PAS) stain, Sudan stain, cytostain, Papanicolaou stain, Nissl stain, azocarmine stain, neutral red or janus green. In further embodiments, the tissue sample may be analyzed by immuno-histochemical staining. Immuno-histochemical staining (IHS) may provide information about the presence, location and distribution of large oncosomes that may be bound to the tissue sample or may be present surrounding the tissue sample. Antigens for HIS include proteins, peptides, nucleic acids, small molecules or any other molecule that may be specifically recognized by an antibody. In various embodiments, the antibodies may specifically bind the cancer specific markers described herein. Unbound antibody may be removed by washing. The specifically bound antibody may be detected by treating the bound antibody with, for example a labeled secondary antibody or labeled avidin/streptavidin. Suitable labels for immunohistochemistry include but are not limited to fluorophores such as fluoroscein and rhodamine, enzymes such as alkaline phosphatase and horse radish peroxidase, and radionuclides such as $^{32}P$ and $^{125}I$. Examples of gene product markers that may be detected by immuno-histochemical staining include but are not limited to cytokeratins (for example basic or neutral cytokeratins (including CK1, CK2, CK3, CK4, CK5, CK6, CK7, CK8 and CK9) and/or acidic cytokeratins (CK10, CK12, CK 13, CK14, CK16, CK17, CK18, CK19 and CK20)), prostate-specific antigen (PSA), prostate-specific membrane antigen (PSMA), caveolin-1

(Cav-1), MCL2, bladder-tumor antigen (BTA), NMP22, carcinoembryonic antigen (CEA), CA 125, CA 19-9, TPA, hormone receptors (for example estrogen and progesterone), HER2/neu antigen, CA15-3, CEA, CA27-29, bcr-abl, CA19-9, EGFR, human chorionic gonadotropin (HCG), alpha fetoprotein (AFP), neuron-specific enolase (NSE), epidermal growth factor receptor (EGFR), TA-90, S-100, immunoglobulins or free light chains, Bence Jones proteins, monoclonal protein (M-protein), CA 125, CA 72-4, LASA-P, HCG, CA 72-4, Lactate dehydrogenase (LDH) or a combination thereof. Additional cancer specific markers include proteins encoded by genes set forth in Table 1

Reference Values

In various embodiments of the processes and methods described herein, the reference value is based on the presence and/or number of large oncosomes in a sample obtained from a subject having cancer (for example, prostate cancer). In one embodiment, large oncosomes are isolated from a blood sample obtained from a subject that has cancer or had cancer. In another embodiment, large oncosomes are detected in a tissue sample obtained from a subject that has cancer of had cancer. As used herein, "subjects that had cancer" refers to subjects that had cancer at any point in their lifetimes and the cancer is in remission.

In some embodiments, the reference value is the mean or median presence (for example, number of large oncosomes, molecular content (such as proteins, nucleic acids, lipids) of the large oncosomes) in a population of subjects that do not have cancer. In such subjects, complete absence of large oncosomes may be expected. In some embodiments, the reference value is the mean or median presence (for example, number of large oncosomes, molecular content (such as proteins, nucleic acids, lipids) of the large oncosomes) of large oncosomes in a population of subject that have cancer in remission. In an additional embodiment, the reference value is the mean or median presence (for example, number of large oncosomes, molecular content (such as proteins, nucleic acids, lipids) of the large oncosomes) of large oncosomes in one or more samples from the subject wherein the one or more samples are obtained at a different (for example, an earlier) time point, such as during diagnosis, before treatment, after treatment or a combination thereof. In an embodiment, the cancer is prostate cancer.

In various embodiments, the large oncosomes in the cancer subject compared to the reference value is increased by at least or about 10%, 20%, 30%, 40%, 50%, 60%, 70%, 80%, 90% or 100%. In various embodiments, the large oncosomes in the cancer subject compared to the reference value is increased by at least or about 1-fold, 2-fold, 3-fold, 4-fold, 5-fold, 10-fold, 15-fold, 20-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, 100-fold or a combination thereof.

Therapies

In accordance with various embodiments of the invention, the therapies that may be prescribed to a subject with increased likelihood of cancer metastases may be selected, used and/or administered to treat a cancer patient (for example a prostate cancer patient). Also in accordance with various embodiments of the invention, the therapies that may be prescribed to a subject identified with having clinically significant prostate cancer may be selected, used and/or administered to treat a prostate cancer patient. In various embodiments, the therapy may be any one or more of surgery, radiation, chemotherapy, immunotherapy, vaccine or combinations thereof.

In some embodiments, chemotherapeutic agents may be selected from any one or more of cytotoxic antibiotics, antimetabolities, anti-mitotic agents, alkylating agents, arsenic compounds, DNA topoisomerase inhibitors, taxanes, nucleoside analogues, plant alkaloids, and toxins; and synthetic derivatives thereof. Exemplary compounds include, but are not limited to, alkylating agents: treosulfan, and trofosfamide; plant alkaloids: vinblastine, paclitaxel, docetaxol; DNA topoisomerase inhibitors: doxorubicin, epirubicin, etoposide, camptothecin, topotecan, irinotecan, teniposide, crisnatol, and mitomycin; anti-folates: methotrexate, mycophenolic acid, and hydroxyurea; pyrimidine analogs: 5-fluorouracil, doxifluridine, and cytosine arabinoside; purine analogs: mercaptopurine and thioguanine; DNA anti-metabolites: 2'-deoxy-5-fluorouridine, aphidicolin glycinate, and pyrazoloimidazole; and antimitotic agents: halichondrin, colchicine, and rhizoxin. Compositions comprising one or more chemotherapeutic agents (e.g., FLAG, CHOP) may also be used. FLAG comprises fludarabine, cytosine arabinoside (Ara-C) and G-CSF. CHOP comprises cyclophosphamide, vincristine, doxorubicin, and prednisone. In another embodiment, PARP (e.g., PARP-1 and/or PARP-2) inhibitors are used and such inhibitors are known in the art (e.g., Olaparib, ABT-888, BSI-201, BGP-15 (N-Gene Research Laboratories, Inc.); INO-1001 (Inotek Pharmaceuticals Inc.); PJ34 (Soriano et al., 2001; Pacher et al., 2002b); 3-aminobenzamide (Trevigen); 4-amino-1,8-naphthalimide; (Trevigen); 6(5H)-phenanthridinone (Trevigen); benzamide (U.S. Pat. Re. 36,397); and NU1025 (Bowman et al.).

In various embodiments, therapies include use of chemotherapeutic agents to treat prostate cancer. Such agents include but are not limited to Abiraterone Acetate, Cabazitaxel, Degarelix, Denosumab, Docetaxel, Enzalutamide, Jevtana (Cabazitaxel), Leuprolide Acetate, Lupron (Leuprolide Acetate), Lupron Depot (Leuprolide Acetate), Lupron Depot-3 Month (Leuprolide Acetate), Lupron Depot-4 Month (Leuprolide Acetate), Lupron Depot-Ped (Leuprolide Acetate), Prednisone, Prolia (Denosumab), Provenge (Sipuleucel-T), Radium 223 Dichloride, Sipuleucel-T, Taxotere (Docetaxel), Viadur (Leuprolide Acetate), Xgeva (Denosumab), Xofigo (Radium 223 Dichloride), Xtandi (Enzalutamide), Zytiga (Abiraterone Acetate) or a combination thereof.

In various embodiments, therapies include, for example, radiation therapy. The radiation used in radiation therapy can be ionizing radiation. Radiation therapy can also be gamma rays, X-rays, or proton beams. Examples of radiation therapy include, but are not limited to, external-beam radiation therapy, interstitial implantation of radioisotopes (I-125, palladium, iridium), radioisotopes such as strontium-89, thoracic radiation therapy, intraperitoneal P-32 radiation therapy, and/or total abdominal and pelvic radiation therapy. For a general overview of radiation therapy, see Hellman, Chapter 16: Principles of Cancer Management: Radiation Therapy, 6th edition, 2001, DeVita et al., eds., J. B. Lippencott Company, Philadelphia. The radiation therapy can be administered as external beam radiation or teletherapy wherein the radiation is directed from a remote source. The radiation treatment can also be administered as internal therapy or brachytherapy wherein a radioactive source is placed inside the body close to cancer cells or a tumor mass. Also encompassed is the use of photodynamic therapy comprising the administration of photosensitizers, such as hematoporphyrin and its derivatives, Vertoporfin (BPD-MA), phthalocyanine, photosensitizer Pc4, demethoxy-hypocrellin A; and 2BA-2-DMHA.

In various embodiments, therapies include, for example, immunotherapy. Immunotherapy may comprise, for example, use of cancer vaccines and/or sensitized antigen presenting cells. The immunotherapy can involve passive immunity for short-term protection of a host, achieved by the administration of pre-formed antibody directed against a cancer antigen or disease antigen (e.g., administration of a monoclonal antibody, optionally linked to a chemotherapeutic agent or toxin, to a tumor antigen). Immunotherapy can also focus on using the cytotoxic lymphocyte-recognized epitopes of cancer cell lines.

In various embodiments, therapies include, for example, hormonal therapy, Hormonal therapeutic treatments can comprise, for example, hormonal agonists, hormonal antagonists (e.g., flutamide, bicalutamide, tamoxifen, raloxifene, leuprolide acetate (LUPRON), LH-RH antagonists), inhibitors of hormone biosynthesis and processing, and steroids (e.g., dexamethasone, retinoids, deltoids, betamethasone, cortisol, cortisone, prednisone, dehydrotestosterone, glucocorticoids, mineralocorticoids, estrogen, testosterone, progestins), vitamin A derivatives (e.g., all-trans retinoic acid (ATRA)); vitamin D3 analogs; antigestagens (e.g., mifepristone, onapristone), or antiandrogens (e.g., cyproterone acetate).

The duration and/or dose of treatment with anti-cancer therapies may vary according to the particular anti-cancer agent or combination thereof. An appropriate treatment time for a particular cancer therapeutic agent will be appreciated by the skilled artisan. The invention contemplates the continued assessment of optimal treatment schedules for each cancer therapeutic agent, where the genetic signature of the cancer of the subject as determined by the methods of the invention is a factor in determining optimal treatment doses and schedules.

In various embodiments, the subject for whom predicted efficacy of an anti-cancer therapy is determined, is a mammal (e.g., mouse, rat, primate, non-human mammal, domestic animal such as dog, cat, cow, horse), and is preferably a human. In another embodiment of the methods of the invention, the subject has not undergone chemotherapy or radiation therapy. In alternative embodiments, the subject has undergone chemotherapy or radiation therapy. In related embodiments, the subject has not been exposed to levels of radiation or chemotoxic agents above those encountered generally or on average by the subjects of a species. In certain embodiments, the subject has had surgery to remove cancerous or precancerous tissue. In other embodiments, the cancerous tissue has not been removed, e.g., the cancerous tissue may be located in an inoperable region of the body, such as in a tissue that is essential for life, or in a region where a surgical procedure would cause considerable risk of harm to the patient, or e.g., the subject is given the anti-cancer therapy prior to removal of the cancerous tissue.

The invention provides a system for determining the likelihood of cancer metastasis wherein large oncosomes are isolated from biological samples obtained from cancer patients. The system includes a sample analyzer configured to produce a signal for mRNA encoding a cancer marker of interest or an miRNA that may be a cancer marker present in the isolated large oncosomes and a computer sub-system programmed to calculate, based on the mRNA or miRNA, whether the signal is greater than or not greater than a reference value.

The invention also provides a system for determining the likelihood of cancer metastasis wherein large oncosomes are isolated from biological samples obtained from cancer patients. The system comprises a sample analyzer configured to produce a signal when a cancer marker specific antibody binds the cancer marker in the isolated large and a computer sub-system programmed to calculate, based on the antibody binding whether the signal is greater than or not greater than a reference value.

In some embodiments, the computer sub-system is programmed to compare the aforementioned signals to reference values to determine a likelihood of cancer metastasis based on an algorithm that classifies the patient as likely to have metastasized form of cancer if the presence of large oncosomes is increased in the subject relative to a reference value.

The invention further provides a computer program product embodied in a computer readable medium that, when executed on a computer, performs steps comprising detecting cancer marker expression in a sample comprising isolated large oncosomes obtained from a cancer patient and comparing the cancer marker expression to a reference value.

The invention further provides combinations and kits comprising isolated large oncosomes and one or more reagents to react with the lipids, carbohydrates, proteins, DNA, RNA or a combination thereof, in the large oncosomes. The reagent may be any one or more of a nucleic acid, an antibody, a small molecule, a lipid or a combination thereof. The reagent may further comprises a label to produce a signal so as to detect the proteins, DNA, RNA or a combination thereof in the oncosomes. The label may be any one or more of a radiolabel, a chromophore, a fluorophore or a combination thereof.

Advantages

Figure 11:
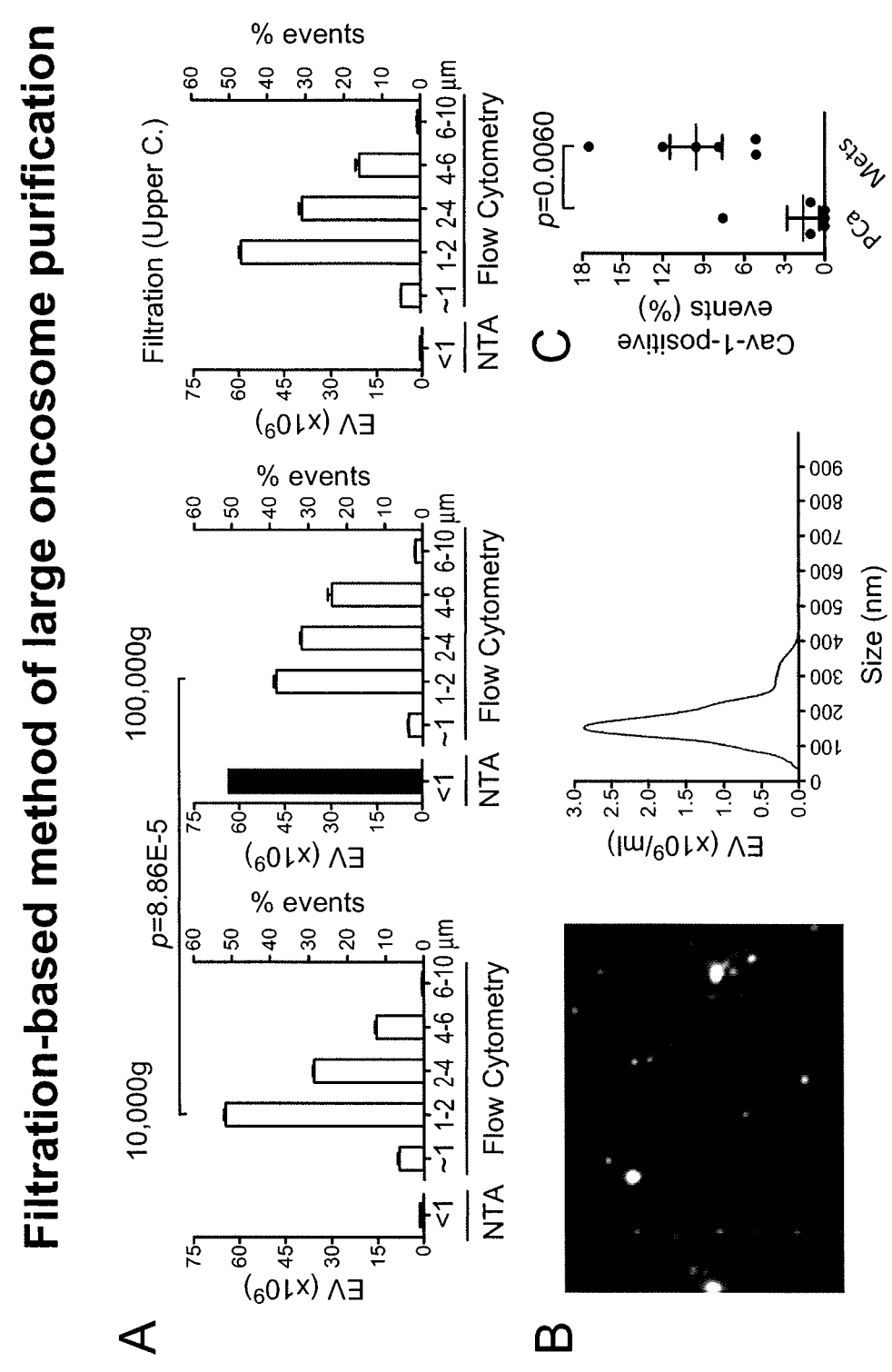
FIG. 11, panels A-C, depicts, in accordance with an embodiment of the invention a comparison between ultracentrifugation and filtration-based protocols. (A) Comparative analysis, by flow cytometry (clear bars), of EV isolated from the medium of the glioblastoma cell line U87, using ultracentrifugation-based protocols (10,000 and 100,000 g) versus the filtration-based protocol, showing that our new method allows detection of large oncosomes in the upper chamber. The comparative analysis was also performed by Nanoparticle Tracking Analysis (NTA) using the NanoSight (black bars) showing that our new method excludes exosomes and microvesicles <1 mm. (B) Snapshot and NTA profile of particles isolated using ultracentrifugation protocol (100,000 g). (C) Using the new method, we show that Cav-1 positive large oncosomes discriminate metastatic prostate cancer.

The "oncosomes" described in Di Vizio et al. (Cancer Res 2009 Vol 69(13) pages 5601-5609), are a mixture exosomes and large oncosomes. Specifically, as shown in FIGS. 10 and 11(*a*), the oncosome purification method described in DiVizio et al. results in a mixture of exosomes (FIG. 11(*a*) middle panel black bar) and large oncosomes (FIG. 11(*a*), middle panel white bars), compared to the filtration method described herein (FIG. 11(*a*) right panel) which yields an isolated population of large oncosomes.

As described herein, presence of large oncosomes in a subject is indicative of increased likelihood of cancer metastasis. The isolation methods described herein, such as (i) the filtration method described in FIG. 11(*a*), optionally followed by fluorescence-activated cell sorting (FACS) with size beads of 1 μm to 10 μm, and (ii) differential centrifugation followed by FACS with size beads of 1 μm to 10 μm, rapidly and selectively enrich for large oncosomes. The purified large oncosomes are selected away from other microvesicles, including exosomes to yield essentially purified large oncosomes (FIG. 1 and (FIG. 11(*a*) right panel)). Since presence and/or an increase in the number of large oncosomes are indicative of increased likelihood of cancer metastasis, the invention provides a quick and simple test (for example a blood test) that may be used to detect cancer metastasis. Since, as described herein, the large oncosomes are produced by cancer cells only and may be detected even without a label, metastasis of any cancer that results in formation and circulation of large oncosomes, may be detected by a simple blood test. Exosomes in contrast may be produced by any cell type (Cocucci et al, 2009; Momen-Heravi F et al. 2013) and exosomes are not necessarily indicative cancer metastasis (compare FIGS. 6C and 6D).

As shown in the exosome field, in vitro results are not necessarily predictive of in vivo events. For example, (see Peinado et al. (*Nature Medicine* 2012 Vol 18(6) pages 883-891) page 884 left column line 16). Di Vizio et al. described in vitro observations in a mixture of microvesicles shed by cultured cancer cells, but it wasn't until the large oncosomes were isolated by the methods described herein that it was apparent that not only are the large oncosomes not an in vitro artifact but are in fact, biologically active comparably if not superior to exosomes and are a marker for cancer metastasis.

EXAMPLES

Example 1

Methods of the Invention

Cell Culture

LNCaP, DU145, PC3 and WPMY-1 were from the American Type Culture Collection (ATCC) (Di Vizio D et al., Oncosome formation in prostate cancer: association with a region of frequent chromosomal deletion in metastatic disease, Cancer Res 2009, 69:5601-5609; Adam R M et al., Cholesterol sensitivity of endogenous and myristoylated Akt, Cancer Res 2007, 67:6238-6246; Di Vizio D et al., Caveolin-1 interacts with a lipid raft-associated population of fatty acid synthase, Cell Cycle 2008, 7:2257-2267). LNCaP/LacZ and LNCaP/MyrAkt1 lines were described (Adam R M et al., Cholesterol sensitivity of endogenous and myristoylated Akt, Cancer Res 2007, 67:6238-6246). For the generation of LNCaP/Vo and LNCaP/Cav-1, parental LNCaP were plated at 70-80% confluence and transfected using Lipofectamine™ 2000 Transfection Reagent (Invitrogen). Stable populations were isolated following selection with Gentamicin G418 0.5 mg/ml. LNCaP were cultured in RPMI-1640 medium supplemented with 10% fetal bovine serum (FBS; Valley Biomedical) 2 mmol/L L-glutamine, 100 U/ml penicillin, and 100 μg/ml streptomycin (all from Invitrogen). DU145 and PC3 were cultured in DMEM supplemented with 10% and 5% (WPMY-1) FBS, 2 mmol/L L-glutamine, 100 U/ml penicillin, and 100 μg/ml streptomycin.

DNA and RNA Extraction

Total nucleic acid was isolated by the TRIzol (Invitrogen) extraction method, and concentration determined by Nano-Drop 2000c spectrophotometer (Biolab). RNA and DNA were fractionated by gel electrophoresis on a 2% agarose gel (Invitrogen) and nucleic acid purity was evaluated by RNase A (Invitrogen) and DNase 1 (Sigma) digestion. 100 ng nucleic acid from vesicles obtained from $2\times10^7$ LNCaP/MyrAkt1 cells was suspended in 15 μl buffer for gel electrophoresis.

Immunoblot Analysis

Cells and purified vesicles were lysed and analyzed by SDS-PAGE and western blotting with the following antibodies: rabbit polyclonal Cav-1 (N-20) (Santa Cruz); HA.11 mAb, clone 16B12 (Covance); Akt1 and p-Akt1 (S473), clone D9E (Cell Signaling), at a dilution of 1:1000; β-actin mAb, clone AC-15 (Sigma), at a dilution of 1:5000. ARF6 antibody was obtained from Brigham and Women Hospital, Boston, MA (Powelka A M et al., Stimulation-dependent recycling of integrin beta1 regulated by ARF6 and Rab11, Traffic 2004, 5:20-36; Di Vizio D et al., Oncosome formation in prostate cancer: association with a region of frequent chromosomal deletion in metastatic disease, Cancer Res 2009, 69:5601-5609). 15 μg protein per lane was loaded for western blotting.

Immunofluorescence Microscopy

Cells were incubated on ice with FITC-conjugated cholera toxin B (CTxB) subunit (Sigma) or Alexa 594-conjugated CTxB (Molecular Probes) and analyzed as previously described (Di Vizio D et al., Caveolin-1 interacts with a lipid raft-associated population of fatty acid synthase, Cell Cycle 2008, 7:2257-2267). For selected experiments, LNCaP/MyrAkt1 were then fixed in 4% paraformaldehyde (PFA), stained with FITC conjugated HA (MyrAkt1) tag (Santa Cruz Biotechnology), and imaged using an Axioplan 2 microscope (Zeiss) (Di Vizio D et al., Caveolin-1 interacts with a lipid raft-associated population of fatty acid synthase, Cell Cycle 2008, 7:2257-2267).

Animal Models and Tumor Xenografts

All experiments were performed in compliance with the guidelines of the Institutional Animal Care and Use Committee, Children's Hospital Boston. We established subcutaneous xenografts injecting $2 \times 10^6$ LNCaP/LacZ or LNCaP/MyrAkt1 cells into the flanks of 8 and 16 SCID mice, respectively. Tumor growth was monitored 3 times per week from detection of the first palpable tumors and the mice were sacrificed before reaching the maximum tumor burden of 2,000 cm³ at all 4 sites (6 weeks post implantation). At necropsy, tumors were removed, weighed, fixed in 10% buffered formalin and embedded in paraffin for histological analysis. The colony of TRAMP and age-matched wild-type mice were maintained in a C57BL6/J background and genotyped as described (Wang S et al., Prostate-specific deletion of the murine Pten tumor suppressor gene leads to metastatic prostate cancer, Cancer Cell 2003, 4:209-221; Chen Z et al., Crucial role of p53-dependent cellular senescence in suppression of Pten-deficient tumorigenesis, Nature 2005, 436:725-730). In some experiments, TRAMP mice from an F1 C57BL6/J X FVB/N cross were used. Pten$^{PbKO}$/Trp53$^{PbKo}$ and PtenI$^{PbKO}$/KRAS mice were maintained as described (Wang S et al., Prostate-specific deletion of the murine Pten tumor suppressor gene leads to metastatic prostate cancer, Cancer Cell 2003, 4:209-221).

Large Oncosome Isolation

Large oncosomes were purified from conditioned medium or from 500 μl of platelet-poor plasma as previously described (Di Vizio D et al., Oncosome formation in prostate cancer: association with a region of frequent chromosomal deletion in metastatic disease, Cancer Res 2009, 69:5601-5609). Briefly, cells and debris were eliminated by centrifugation at 2,800×g per 10 min. The supernatant was centrifuged at 100,000×g for 80 min. Purified oncosomes were washed in PBS, stained with the indicated antibodies, fixed and permeabilized in ethanol, then analyzed by FACS and sorted using 1 and 10 μm bead standards, followed by microscopic examination. In selected experiments, unfixed large oncosomes were sorted using size gates with 1 and 10 μm bead standards and used for biological experiments.

Gelatin Zymography and In Vitro Degradation Assay

Lysed particles isolated from growth media were analyzed by gelatin zymography (substrate gel electrophoresis) (Braunhut S J and Moses M A. Retinoids modulate endothelial cell production of matrix-degrading proteases and tissue inhibitors of metalloproteinases (TIMP), J Biol Chem 1994, 269:13472-13479). The gelatin degradation assay was performed by seeding isolated particles (1-5 μg) on FITC-labeled gelatin coated coverslips for 1.5 hr, at 37° C. using a modification of a published protocol (Ramachandran A et al., An Akt- and Fra-1-dependent pathway mediates platelet-derived growth factor-induced expression of thrombomodulin, a novel regulator of smooth muscle cell migration, Am J Pathol 2010, 177:119-131).

Migration Assays $1 \times 10^5$ mouse dermal endothelial cells (MDEC), tumor endothelial cells (TEC), or DU145 cells treated with vesicles shed from cells (10 μg/mL) were stained with CellTracker RED CMPTX (Invitrogen), and assayed in Transwell FluoroBlok inserts for 16 hours. Cell migration was measured as described (Ramachandran A et al., An Akt- and Fra-1-dependent pathway mediates platelet-derived growth factor-induced expression of thrombomodulin, a novel regulator of smooth muscle cell migration, Am J Pathol 2010, 177:119-131). Alternatively, WPMY-1 cells ($1.5 \times 10^5$) were seeded into the bottom of 24-well plates and treated for 24 hr with 10 μg/mL LNCaP/MyrAkt1 vesicles. DU145 cells ($1 \times 10^5$), labeled with CellTracker, were seeded into FluoroBlok inserts placed into the WPMY-1-conditioned media and migration monitored as above. Vesicles were unfixed when used in migration assays. Results represent fold-changes from the average of biological triplicates performed in technical duplicate.

Flow Cytometry

Purified vesicles were stained with propidium iodide (PI) Staining Buffer (BD Bioscience) or with the indicated antibodies, were processed on a Moflo High-Speed Cell Sorter (Beckman-Coulter) and analyzed using FlowJo software (Treestar). 1 and 10 μm bead standards (Spherotech Inc.) were used to set size gates. At least 3,000 events were recorded (Wersto R P et al., Doublet discrimination in DNA cell-cycle analysis, Cytometry 2001, 46:296-306). The following antibodies were used: HA-probe (F-7) FITC (Santa Cruz), at a dilution of 1:200, Cav-1 (N-20) (Santa Cruz), at dilution 1:200.

Electron Microscopy

Large Oncosomes.

Purified material was adsorbed to glow-discharged, carbon-coated copper grids and stained with 0.75% (w/v) uranyl formate as described (Ohi M et al. Negative Staining and Image Classification—Powerful Tools in Modern Electron Microscopy, Biol Proced Online 2004, 6:23-34). Images were collected on a Philips CM10 electron microscope (FEI) operated at an acceleration voltage of 100 kV. Images were recorded on a 1K CCD camera (Gatan) at a magnification of 50,000× and a defocus of about −1.5 μm.

Human Xenografts.

Sections from the paraffin embedded subcutaneous tumors were deparaffinized and fixed for 2 hours in Karnovsky fixative before post-fixation with 1% OsO4 and 0.03 g/4 ml of potassium ferrocyanide. Sections were then stained overnight with 2% uranyl acetate, dehydrated and embedded overnight with a 1:1 mixture of LX 112 resin and 100% ethanol. Electron micrographs were collected on a JEOL 1400 TEM operated at an acceleration voltage of 120 kV.

Immunohistochemistry

Sections from the paraffin embedded mice tumors, human core biopsies, and human TMA were stained (Adam R M et al., Cholesterol sensitivity of endogenous and myristoylated Akt, Cancer Res 2007, 67:6238-6246; Di Vizio D et al., Caveolin-1 interacts with a lipid raft-associated population of fatty acid synthase, Cell Cycle 2008, 7:2257-2267Di Vizio D et al., Caveolin-1 is required for the upregulation of fatty acid synthase (FASN), a tumor promoter, during prostate cancer progression, Cancer Biol Ther 2007, 6:1263-1268) with the following antibodies: Akt mAb (Cell Signaling) at a dilution of 1:500; HA.11 mAb, clone 16B12 (Covance), at a dilution of 1:100, CK18 rabbit polyclonal Ab (Epitomics), at dilution of 1:200.

Patients and Samples

Three human tissue cohorts were used: 1) core biopsies with localized prostate cancer from 15 patients from the Department of Pathology of University of Naples, Italy; 2) a TMA from Ulm, Germany, containing 26 multifocal specimens, with at least 2 distinct cancer foci in the prostate gland and 1 lymph node metastasis; 3) a TMA containing 36 benign prostate samples, 36 organ confined, and 36 metastatic tumors, of which 11, 20 and 23 samples, respectively, were available for the analysis (Di Vizio D et al., Caveolin-1 interacts with a lipid raft-associated population of fatty acid synthase, Cell Cycle 2008, 7:2257-2267; Di Vizio D et al., An absence of stromal caveolin-1 is associated with advanced prostate cancer, metastatic disease and epithelial Akt activation, Cell Cycle 2009, 8:2420-2424; Mukhopadhyay N K et al., Heterogeneous nuclear ribonucleoprotein K is a novel regulator of androgen receptor translation, Cancer Res 2009, 69:2210-2218; Cinar B et al., The pro-apoptotic kinase Mst1 and its caspase cleavage products are direct inhibitors of Akt1, EMBO J 2007, 26:4523-4534). Informed consent was obtained from all subjects.

Statistical Analysis

Comparisons between experimental groups were performed using two-tailed, unpaired Student's t test. Pearson's chi-square test was used to assess the correlation between percentage of MyrAkt1-positive events and tumor weight. Fisher exact test was applied to assess association between presence of large oncosome-like structures and Gleason score groups and metastases. In all experiments, a $p<0.05$ was considered significant.

Example 2

Filtration-Based Isolation Protocol

Serum-free conditioned media or human platelet-poor plasma are centrifuged at low speed (2,800 g/10 min) to eliminate cells and cell-debris. In comparison with the ultra-centrifugation based protocol, in which extracellular vesicles (EV) are recovered from the supernatant after centrifugation at 10,000 g/30 min or 100,000 g/60 min, in our new protocol supernatant is filtered at 8,000 g/30 sec using Vivaspin ultrafiltration spin columns. Large oncosomes are recovered from the top of the filter membrane (upper chamber), whereas small EV, are eluted (lower chamber) (FIGS. 10 and 11).

Figure 2:
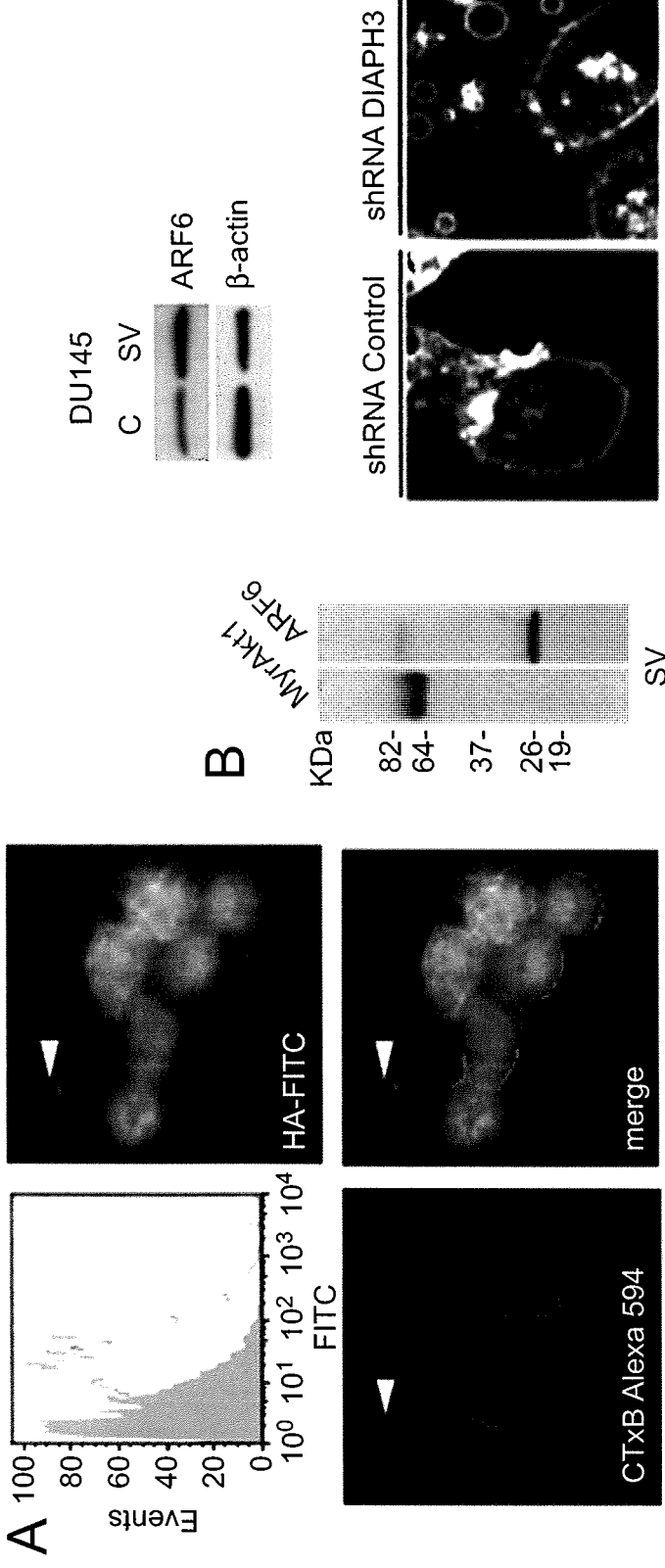
FIG. 2, panels A-G, depicts, in accordance with an embodiment of the invention that large oncosomes are bioactive and can be identified by FACS. (A) LNCaP/MyrAkt1-derived vesicles, stained with HA-FITC-labeled antibody to detect MyrAkt1, were analyzed by FACS. Unstained vesicles were used as a negative control (grey-shaded). LNCaP/MyrAkt1 cells, stained with Alexa-594-CTxB and FITC-HA-labeled antibody to detect MyrAkt1 (40×). Arrowheads point to a shed large oncosome. (B) Shed vesicles (SV) and/or cell lysates (C) from LNCaP/MyrAkt1 and DU145 cells were blotted with the indicated antibodies. The micrographs show DU145 shRNA control and DU145 DIAPH3-silenced (shRNA) cells stained with CTxB, revealing large oncosomes produced by DIAPH3 silencing. (C) Mouse dermal endothelial cell (MDEC) and tumor endothelial cell (TEC) migration induced by incubation with LNCaP/MyrAkt1-derived vesicles. The image depicts a heat map of a 24-well plate showing an increase in CellTracker fluorescence (red) from migrated cells, in response to treatment with LNCaP/MyrAkt1 vesicles or vehicle. Experiments were performed in technical duplicate and biological triplicates (Exp. A, B, and C). Treatment with SV increased migration rates in both cells lines significantly: p=0.038 and p=0.028, respectively. (D) Fold change in CellTracker fluorescence of DU145 incubated with SV or vehicle; SV induced significantly higher migration than vehicle in DU145 prostate cancer cells p=0.011. (E) Fold change in CellTracker fluorescence of DU145 cells migrating in response to WPMY-1 stromal cells as attractant. WPMY-1 cells were incubated with SV or vehicle, and DU145 cell migration toward the stromal cells monitored as in (D) p=0.021. (F) Protein extracts from SV (lane 1), cells (lane 2) and cells+SV (lane 3) were blotted with the indicated antibodies. Lane 1: Protein extracts from LNCaP/MyrAkt1-derived SV; Lane 2: Protein extracts from WPMY-1 cells before exposure to SV; Lane 3: Protein extracts from WPMY-1 cells after exposure to LNCaP/MyrAkt-derived SV. (G) Wild type mouse prostate fibroblasts were incubated with SV and analyzed by qRT-PCR (RT2 profiler PCR array (Qiagen)) for BDNF, CXCL12, osteopontin, and IL-6 mRNA levels. Exposure to SV resulted in a significant upregulation of these pro-metastatic factors in comparison to vehicle (Ctrl). Changes are shown as relative units of gene expression in comparison with a pool of 5 housekeeping genes.
Figure 2:
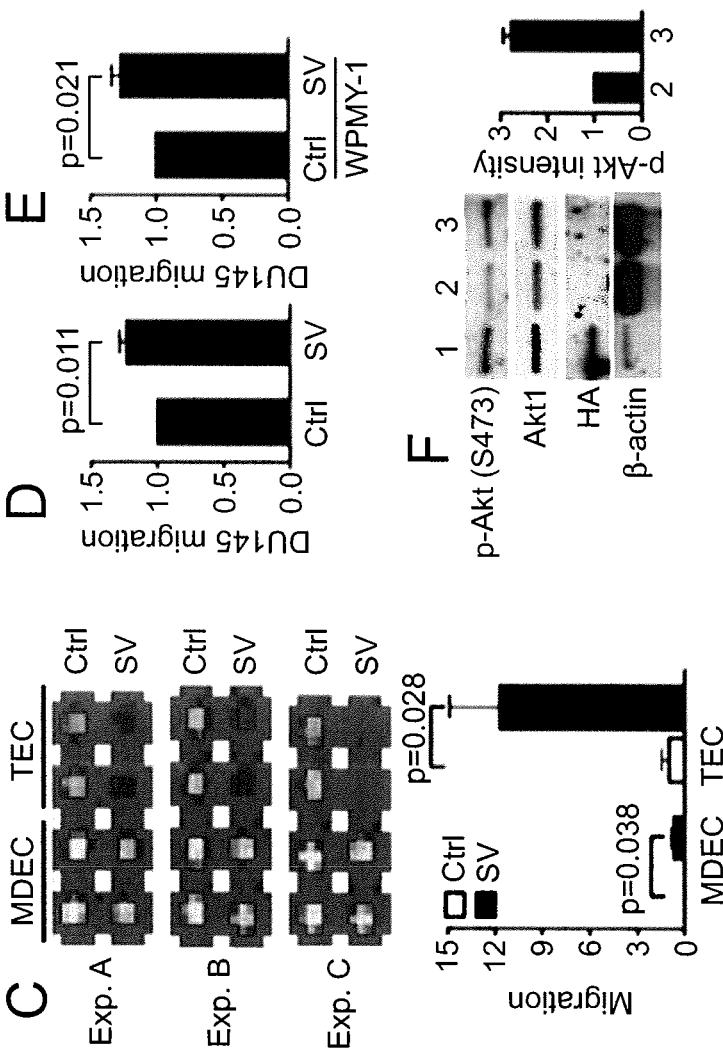

Tumor cells that exhibit the amoeboid feature of membrane blebbing can release large, plasma membrane-derived vesicles into the extracellular space (Di Vizio D et al., Oncosome formation in prostate cancer: association with a region of frequent chromosomal deletion in metastatic disease, Cancer Res 2009, 69:5601-5609) (FIGS. 1A, 1B, 2A). To determine whether these vesicles can be isolated and analyzed, shed vesicles were purified from the conditioned medium of LNCaP human prostate cancer cells stably expressing the potent oncogene MyrAkt1 (Adam R M et al., Cholesterol sensitivity of endogenous and myristoylated Akt, Cancer Res 2007, 67:6238-6246), and from WPMY-1 prostate stromal cells. The contents of the purified vesicles reacted with propidium iodide (PI) (FIG. 7A), consistent with the presence of RNA (FIG. 1C). This allowed detection of a PI-positive vesicle population by fluorescence activated cell sorting (FACS). The stromal cells produced substantially fewer vesicles than LNCaP/MyrAkt1 cells ($p<0.001$) (FIG. 1D). Biochemical purification coupled with FACS sorting was thus in agreement with results using a visual quantitative bleb-formation assay (Di Vizio D et al., Oncosome formation in prostate cancer: association with a region of frequent chromosomal deletion in metastatic disease, Cancer Res 2009, 69:5601-5609). Shed vesicles from LNCaP/MyrAkt1 cells produced zones of proteolytic clearance in a fluorescent gelatin matrix assay (Ayala I et al., Multiple regulatory inputs converge on cortactin to control invadopodia biogenesis and extracellular matrix degradation, J Cell Sci 2008, 121:369-378) (FIG. 1E) in a similar size range (2-4 μm) and modal distribution to >1 μm diameter membrane blebs observed microscopically (FIGS. 1F, G). MMP zymography showed that the vesicle preparations contained bioactive MMP9 and MMP2, two key proteases involved in tumor cell invasion (FIG. 1E).

Shed vesicles isolated from LNCaP/MyrAkt1 cells contained abundant, membrane-localized MyrAkt1 as demonstrated by FACS and immunofluorescence staining (IF) (FIG. 2A) and by western blotting (FIG. 2B). These results indicated that MyrAkt1 is a potentially useful marker with which to track large shed vesicles produced by LNCaP/MyrAkt1 cells in vivo. Vesicles shed and purified from U87 glioma cells, which exhibit amoeboid properties, contained Caveolin-1 (Cav-1), similar to DU145 prostate cancer cell-derived vesicles (Di Vizio D et al., Oncosome formation in prostate cancer: association with a region of frequent chromosomal deletion in metastatic disease, Cancer Res 2009, 69:5601-5609). DU145- and LNCaP/MyrAkt1 vesicle preparations also contained ARF6 (FIG. 2B), a GTPase shown recently to mediate large microvesicle shedding from tumor cells and to be enriched in TMV (Muralidharan-Chari V. et al., ARF6-regulated shedding of tumor cell-derived plasma membrane microvesicles, Curr Biol 2009, 19:1875-1885). As reported previously (Di Vizio D., et al., Oncosome formation in prostate cancer: association with a region of frequent chromosomal deletion in metastatic disease, Cancer Res 2009, 69:5601-5609), silencing of the GTPase-regulated form in DIAPH3 in DU145 cells potentiated shedding of large microvesicles (FIG. 2B). As reported in another recent study, DIAPH3 loss in DU145 and other tumor cell backgrounds results in amoeboid behavior[10], providing further evidence that shedding of large TMV are a feature of the amoeboid tumor phenotype.

Figure 7:
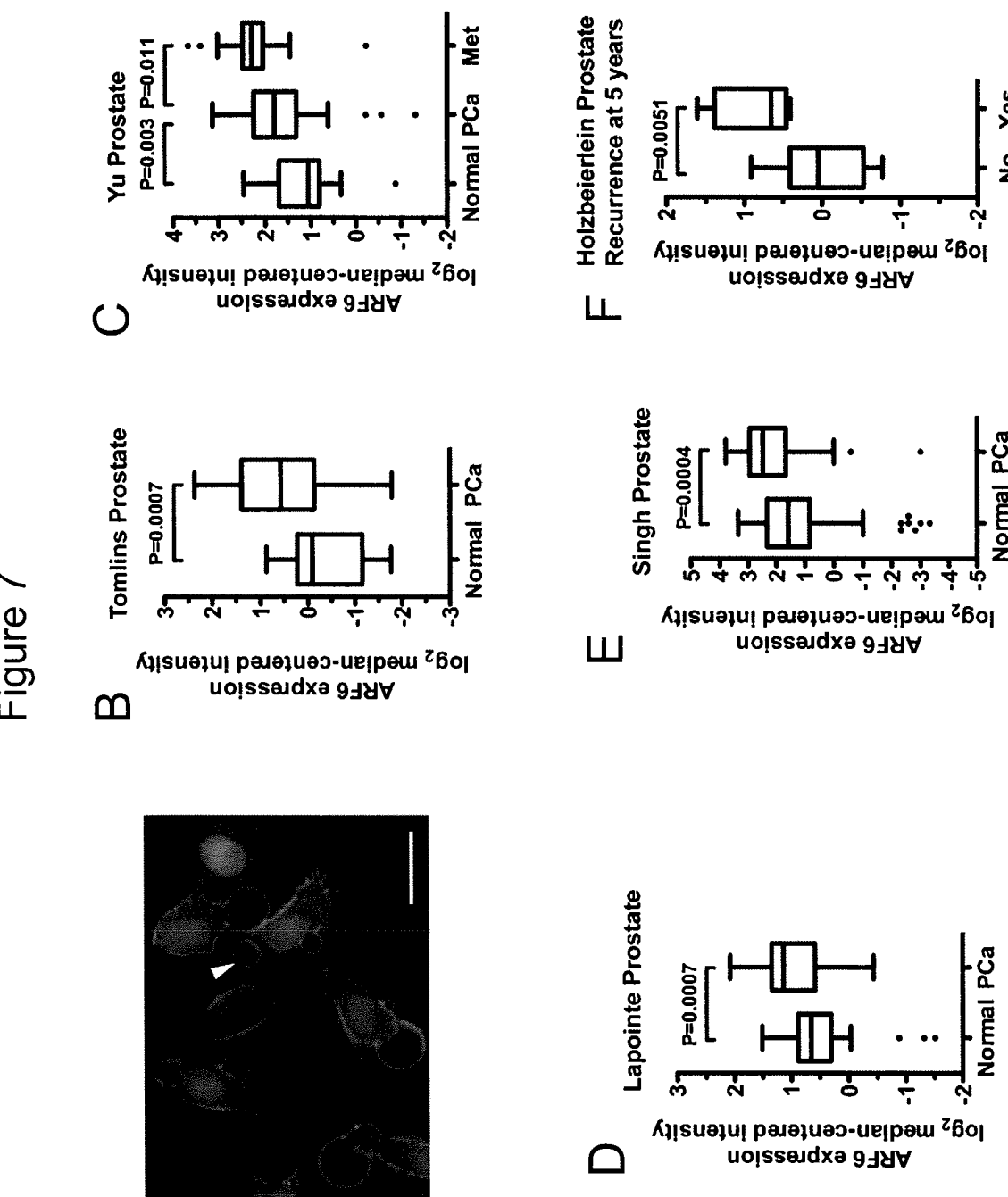
FIG. 7, panels A-G, depicts, in accordance with an embodiment of the invention that ARF6 is overexpressed in human prostate cancer. (A) EGF-treated blebbing PC3 cells labeled with FITC-CTxB and propidium iodide (PI) were imaged using an Axioplan 2 microscope (scale bar: 10 μm). (B) 9 independent expression data sets comparing normal prostate tissue and prostate adenocarcinoma consistently show significant upregulation of ARF6 expression levels in prostate cancer. Of these, 4 studies rank ARF6 expression levels in the top fifth percentile of all upregulated genes and 3 studies rank ARF6 in the tenth percentile. (C-F) Box plots showing AFR6 expression levels in normal prostate, prostate adenocarcinomas and metastatic lesions of 4 representative and high-powered expression profiles (Tomlins at al., Yu et al., Lapointe et al., Singh et al.) (G) Elevated ARF6 expression correlates with disease recurrence at 5 years (Holzbeierlein et al.)

Sustained ARF6 activation enhances tumor cell invasion in cell and animal model systems and vesicle shedding may be a potential mechanism for ARF6-induced acquisition of invasive potential. Interrogation of publicly available prostate cancer expression data sets demonstrated that ARF6 mRNA levels are higher in prostate cancer in comparison with benign tissue (FIG. 7). ARF6 ranked in the top 10 percentile of overexpressed genes in these data sets, and ARF6 mRNA was significantly upregulated in metastases and in recurrent disease.

The MMP activity seen with large vesicles shed from LNCaP/MyrAkt1 cells (FIG. 1F-H) indicates that they are bioactive. In separate bioactivity tests, these vesicle preparations stimulated migration of mouse tumor endothelial cells (TEC), mouse dermal endothelial cells (MDEC) (Dudley A C et al., Calcification of multipotent prostate tumor endothelium, Cancer Cell 2008, 14:201-211) (FIG. 2C) and DU145 cells (FIG. 2D). LNCaP/MyrAkt1 vesicles also activated WPMY-1 stromal cells to produce factors that stimulated migration of DU145 cells (FIG. 2E). LNCaP/MyrAkt1 vesicles also activated Akt1 in WPMY-1 stromal cells (FIG. 2F). Finally, incubation of mouse prostatic fibroblastic cells with LNCaP/MyrAkt1 vesicles resulted in increased expression of the pro-metastatic factors BDNF, CXCL12, and osteopontin (FIG. 2G). Collectively, these data indicate that LNCaP/MyrAkt1 cells shed oncosomes, including particles considerably larger than nanosized microvesicles, with the potential to contribute to oncogenic signaling by acting as paracrine effectors of inter-tumor cell, tumor cell-endothelial cell, and epithelial-stromal reaction.

Example 3

Large Oncosomes in the Circulation and In Situ

Figure 3:
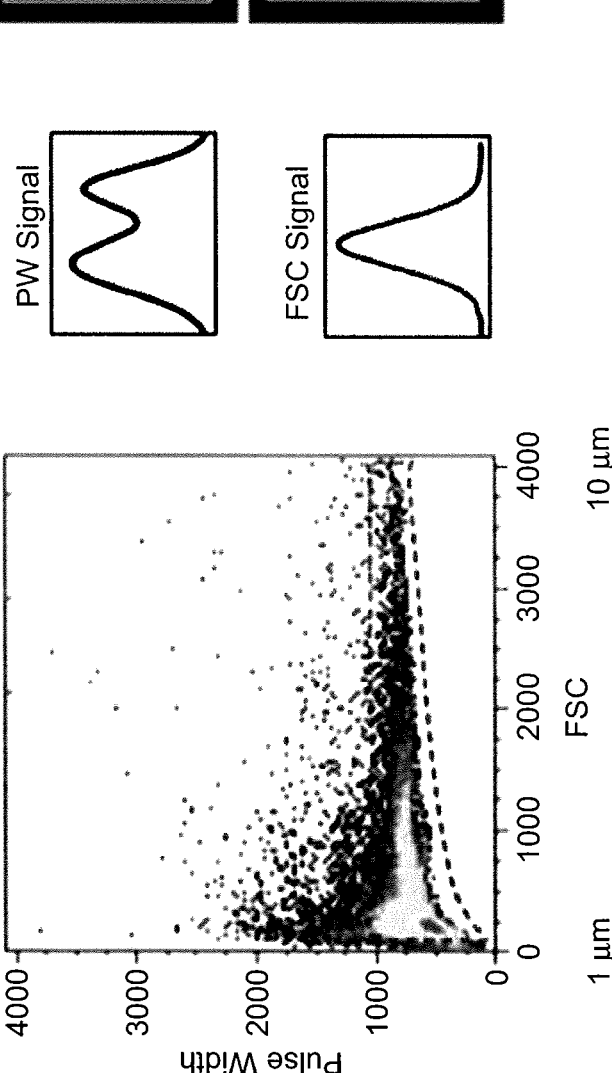
FIG. 3, panels A-B, depicts, in accordance with an embodiment of the invention the analysis of shed vesicles and detection of large oncosomes by FACS and microscopy. (A) Purified vesicles derived from LNCaP/MyrAkt1 cells, stained with a FITC-conjugated HA antibody, were plotted by setting FSC vs. PW signal on a linear scale (left panel). A schematic representation of two signal pulses from the flow cytometer detector, corresponding to single particles (bottom) and doublet particles (top) is shown in the right panels. Gated single events (within the red dotted line on the left panel) were visualized at the microscope and considered for further analysis. Signal pulses generated from aggregates (outside of the red dotted line) were excluded. (B) Fluorescence and electron micrographs of MyrAkt1-positive particles sorted using size beads smaller and larger than 1 μm. The arrowhead highlights the lipid bilayer structure of the vesicle-encapsulating membrane.

Microvesicles range from about 20 nm to about 10 μm. Exosomes (a type of microvesicles) range from about 20 nm to about 100 nm. Large oncosomes (another type of microvesicles) range in size from about 1 μm to about 10 μm. To distinguish large oncosomes from smaller TMV unequivocally, ultracentrifugation and immuno-flow cytometry were used in combination with sizing beads to create a calibrated domain of analysis based on size. Following biochemical purification, shed vesicles were stained with DAPI to verify the absence of cellular contamination and subsequently labeled with an HA antibody, for detection of membrane-localized MyrAkt1. MyrAkt1-negative and -positive populations were then distinguished on a cell sorter, with gates set using 1 and 10 μm beads (FIG. 3A). Because aggregates may potentially be a significant component of the vesicle preparation, we excluded them from the analysis. To do this, forward scatter signal (FSS) was plotted against pulse width (PW) of the same signal on a linear scale (FIG. 3A). Electronic signal pulses are composed of pulse height (PH) and PW, and the latter is a function of the time necessary to traverse the laser beam, which is shorter for single particles. Electric pulses from a flow cytometer detector with narrow PW identify a singlet (bottom), whereas those with broader PW identify doublets or possibly clumps (top). In order to restrict our analysis to single vesicles, we delineated a region in which only single events were analyzed based on their smaller and more homogeneous PW signals and their corresponding forward scatter signals (FIG. 3A, red dotted line). Only these events were gated and considered for further analysis (FIG. 3A, right bottom panel). Electric pulses generated from aggregates, as indicated by increased PW (FIG. 3A, right top panel), were excluded from the analysis, as validated microscopically (FIG. 3A, B).

Sorted single events <1 μm and >1 μm were visualized by both fluorescence and electron microscopy (EM), indicating that large, single vesicles can be distinguished within a mixed population. Microscopic analysis of retrieved vesicles following ultracentrifugation and other sorting procedures indicated that they were not aggregates of smaller particles and they had a definable structure (FIG. 3A,B). These results indicate that large vesicles can be isolated as discrete events using a tumor cell-specific marker.

Figure 4:
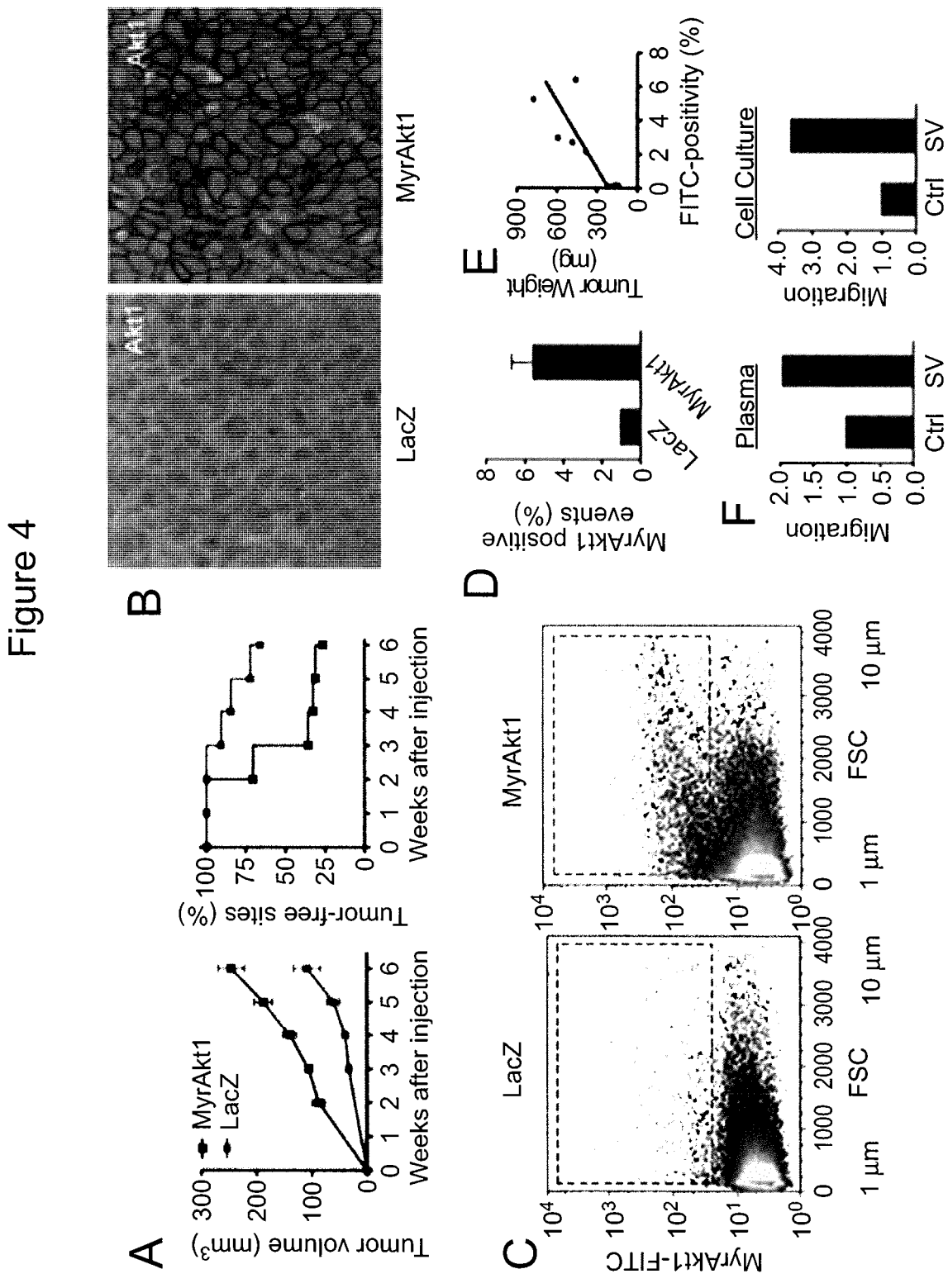
FIG. 4, panels A-H, depicts, in accordance with an embodiment of the invention the identification of large oncosomes in vivo. (A) Tumor growth and tumor take in LNCaP/MyrAkt1 and LNCaP/LacZ xenografts (growth, p<0.01); (sc sites free of tumor, p=0.01). (B) Akt1 immunostaining of paraffin sections of the indicated xenografts. Note the prominent Akt membrane staining in the MyrAkt1 tumors, in contrast to its diffuse cytosolic staining in the LacZ tumor sections. (C) Left, FACS analysis of 1-10 μm MyrAkt1-positive vesicles purified from the plasma of mice carrying LNCaP/MyrAkt1 and LNCaP/LacZ xenografts. The dot plot depicts FSC and FL1 (MyrAkt1), and the red gate indicates positive events. (D) Quantitative evaluation of MyrAkt1-positive events. A cutoff corresponding to the 99th percentile of vesicles isolated from the plasma of mice with LNCaP/LacZ tumors was chosen to segregate negative and positive events. (E) In mice with LNCaP/MyrAkt1 tumors, the percentage of MyrAkt1-positive vesicles correlated with tumor weight (p-value: 0.007). (F) Mouse dermal endothelial cells (MDEC) exhibited increased migration when exposed to oncosomes in comparison to vehicle. In the left panel, the vesicles were isolated from the plasma of mice with MyrAkt1 tumors. In the right panel, vesicles were derived from the medium of LNCaP/MyrAkt1 cells. (G) Tumor sections of LNCaP/MyrAkt1 xenografts stained with hematoxylin and eosin (H&E); arrowheads point to large vesicles, similar in appearance to large oncosomes. Sections were also immunostained with an Akt1 antibody, which identified Akt1 at the plasma membrane and allowed visualization of large vesicles. (H) Tumor sections of LNCaP/MyrAkt1 xenografts imaged by TEM. Membrane blebs protruding from tumor cells near blood vessels are highlighted.
Figure 4:
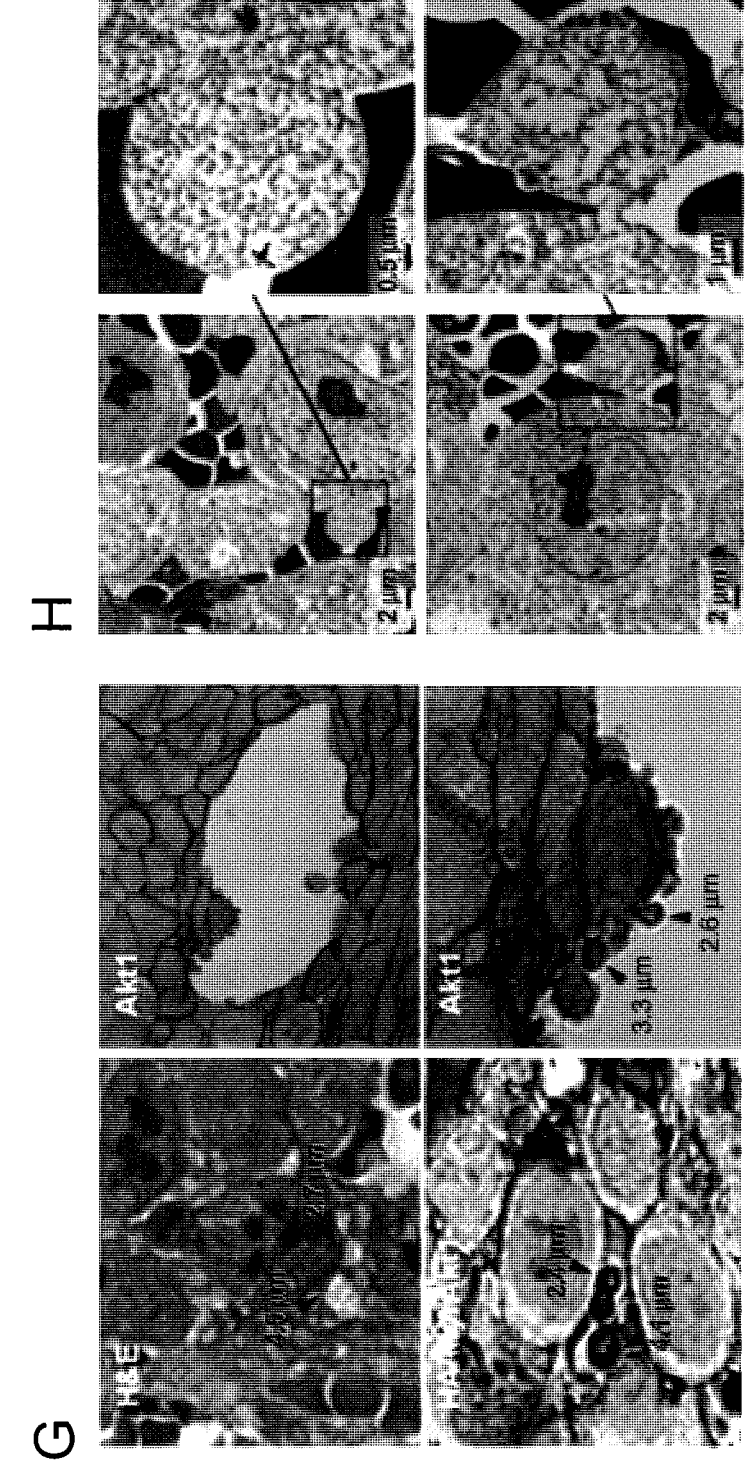

Having demonstrated that membrane blebs shed by cells can be sorted by FACS as discrete large vesicles, a similar approach was used to isolate and quantify these in the circulation of SCID mice carrying LNCaP/MyrAkt1 xenograft tumors. All mice injected subcutaneously with either LNCaP/MyrAkt1 or LNCaP/LacZ control cells in Matrigel developed tumors; however, LNCaP/MyrAkt1 tumors were significantly larger than LNCaP/LacZ tumors (FIG. 4A). Akt1 was membrane localized in LNCaP/MyrAkt1 tumors as detected with both Akt1 and HA antibodies (FIG. 4B). Plasma from mice carrying LNCaP/MyrAkt1 tumors contained MyrAkt1-positive events in the 1-10 μm size range that were sorted with the HA antibody (FIG. 4C,D). The number of MyrAkt1 events detected by FACS correlated with tumor weight (p<0.01) (FIG. 4*e*). Because the HA antibody does not recognize an endogenous epitope in the mouse, these data indicate that tumor-derived large vesicles from the subcutaneous xenografts gain access to the circulation.

MyrAkt1-positive vesicles isolated from the blood of mice with MyrAkt1 tumors stimulated migration of normal endothelial cells (FIG. 4F, left panel), suggesting the capability of oncosomes in the circulation to evoke progression-related changes in the microvasculature. A similar result was obtained with MyrAkt1-positive vesicles sorted by FACS in the 1-10 μm size range from the medium of LNCaP/MyrAkt1 cells (FIG. 4F, right panel), indicating that large oncosomes are bioactive.

High magnification microscopy of LNCaP/MyrAkt1 tumors revealed membrane vesicles within a similar size range to the large oncosomes identified in vitro and in the circulation of the same animals (FIG. 4G). To our knowledge, this type of membrane vesicle has not been previously described in paraffin sections of prostate tumors. Large oncosome-like structures were evident when sections of LNCaP/MyrAkt1 tumors were stained with hematoxylin and eosin, and immunostained with Akt1 and HA antibodies (FIG. 4G). Morphological features with the appearance of intravasating amoeboid cells were identifiable by immunostaining with Akt1 antibody (FIG. 4G, right panels). Akt1-positive vesicles in tumor tissues were also positive for ARF6, thus resembling large oncosomes secreted from LNCaP/MyrAkt1, and DU145 cells (FIG. 2B), and in accordance with the amoeboid character of these cell lines. Transmission electron microscopy (TEM) of LNCaP/MyrAkt1 tumor sections showed that the tumor cells produced large, bulbous structures with the appearance of membrane sacs, often in the proximity of vascular lacunae (FIG. 4H). Higher magnification revealed internal structures with features resembling polyribosomes. These results suggest that MyrAkt1-positive vesicles detected in the circulation of tumor-bearing mice arise from membrane blebs similar or identical to amoeboid blebs produced in cell culture.

Example 4

Large Oncosome-Like Vesicles as a Feature of Metastatic Prostate Cancer

Figure 5:
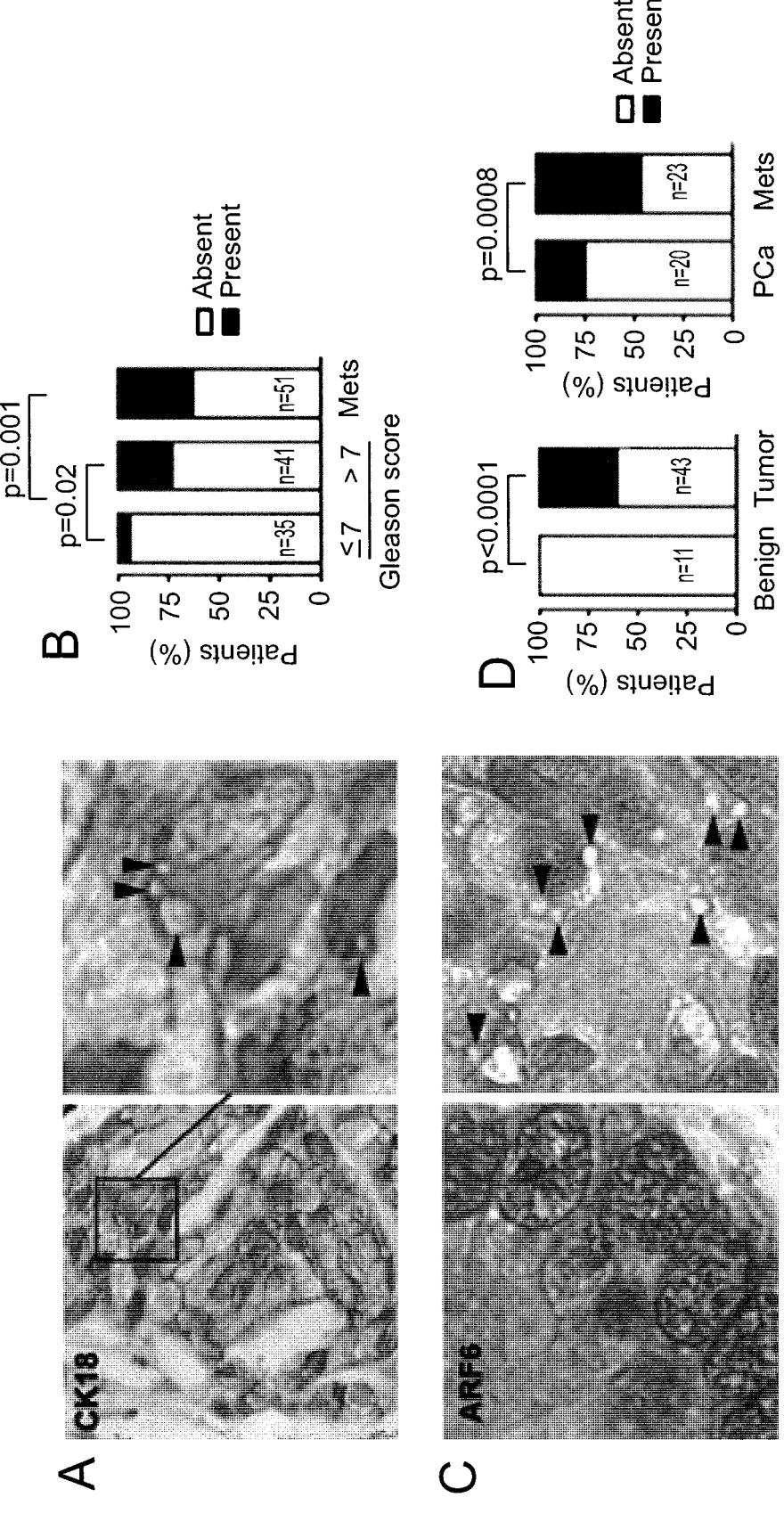
FIG. 5, panels A-D, depicts, in accordance with an embodiment of the invention the large oncosome-like vesicles in metastatic prostate cancer. (A) Representative paraffin section of human core biopsies of patients with prostate cancer (Gleason score 4+3) immunostained with CK18 antibody. Arrowheads point to structures resembling large oncosomes. (B) Quantitative analysis of the distribution of ARF6 positive large oncosome-like vesicles among the diagnostic categories, showing vesicles are significantly more abundant in Gleason score >7 than in Gleason score <7 (p=0.020) and in Mets than in organ-confined tumors (PCa) (p=0.001). (C) Representative sections of an additional prostate cancer TMA stained with ARF6 showing absence (left) and presence (right) of large oncosome-like vesicles in the right panel (arrowheads). (D) The presence of structures resembling large oncosomes significantly discriminates between normal and tumor samples (p<0.0001), and between organ confined disease and metastasis (p=0.0008).

Identification of similar large vesicles in human prostate cancer specimens was investigated. ARF6 staining revealed vesicular structures in the 1-10 μm size range. Initially a small cohort of human core biopsies (n=15) with localized prostate cancer was examined, and ARF6-positive large oncosome-like structures in the tumor tissue of 3 specimens were identified. Significantly, similar vesicular structures were also identified using a CK18 antibody, which detects prostate luminal epithelial cells (FIG. 5A). To determine whether the identification of ARF6-positive vesicles in tissues may reflect clinical status, a tissue microarray (TMA) containing over 120 punches from foci of localized and metastatic human prostate cancer was examined (Perner S et al., ERG rearrangement metastasis patterns in locally advanced prostate cancer, Urology 2010, 75:762-767). High magnification revealed ARF6-positive vesicles more frequently in foci of Gleason score >7 in comparison with foci of lower Gleason score (p=0.02), suggesting that identification of large oncosome-like structures in situ may indicate tumor progression. Notably, metastatic foci exhibited significantly more vesicles (p=0.001) (FIG. 5B). These characteristics represent a previously unrecognized histologic feature of aggressive prostate cancer.

To determine whether the presence of vesicular structures identified using similar criteria can differentiate indolent vs.

fatal cancer, two models of Pten-deficient mice with greatly different biological course were used. Pten$^{PbKO}$/Trp53$^{PBKO}$ mice develop prostate adenocarcinoma that remains organ-confined within 10-16 weeks after gestation. In comparison, Pten$^{PbKO}$/KRAS mice develop distant metastases in the liver and lung, and also develop castrate resistance following androgen ablation. ARF6-positive vesicles, similar in appearance and size to those seen in the LNCaP/MyrAkt1 tumors, were abundant in Pten$^{PbKO}$/KRAS tissues but were absent in the Pten$^{PbKO}$/Trp53$^{PBKO}$ prostatic tissues. These findings suggest that large oncosome features in prostate tumors may generally report aggressive disease.

Also analyzed was an additional human prostate TMA containing benign samples, organ confined tumors, and metastatic tumors. FIG. 5C shows representative images of absence (left) and presence (right) of large oncosome-like structures detected using anti-ARF6. These features were present in less than 30% of the tumors and were not detected in benign prostate tissue. A significant correlation between the presence of large oncosome-like features and metastasis (p=0.0008) was observed. The presence of these features also discriminated between benign and tumor tissue (p<0.0001) (FIG. 5D).

Example 5

Large Oncosomes Containing Caveolin-I Identify Aggressive Prostate Cancer

Figure 8:
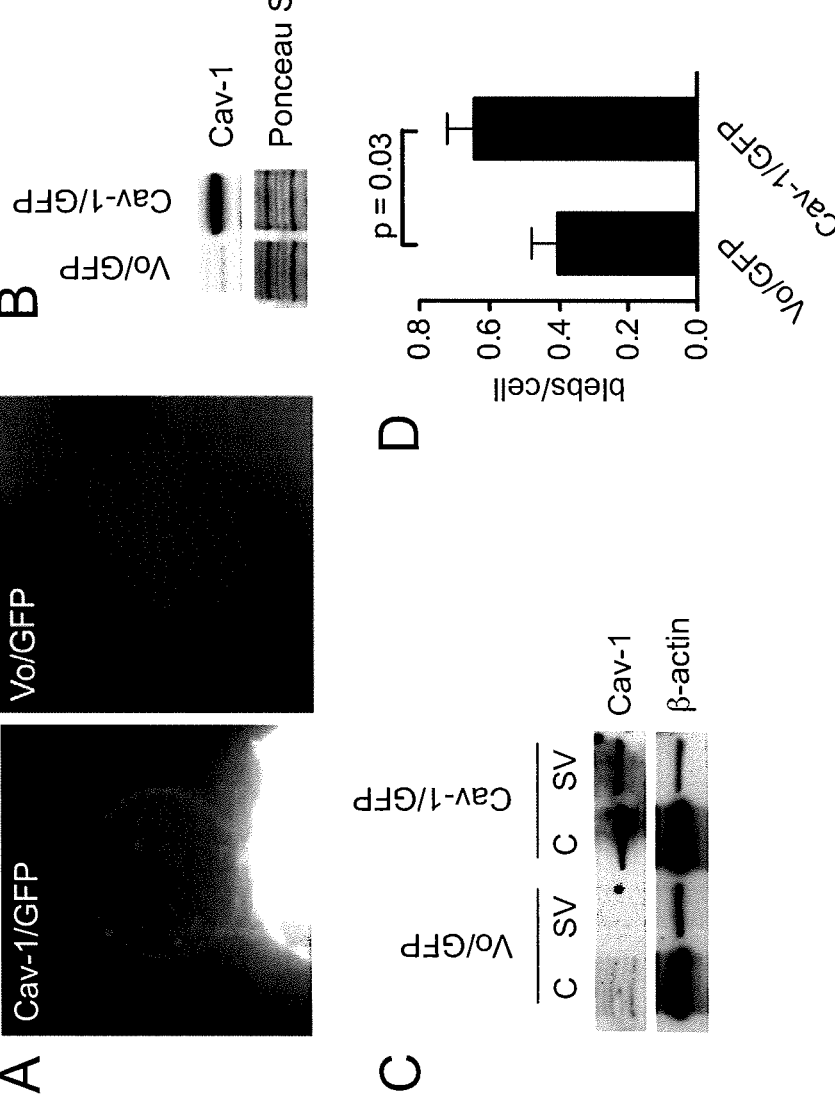
FIG. 8, panels A-D, depicts, in accordance with an embodiment of the invention the establishment of LNCaP cells overexpressing Cav-1/GFP. (A) LNCaP cells were engineered to overexpress a Cav-1/GFP fusion protein or vector only (Vo)/GFP and photographed by fluorescence microscopy (40×). (B) Whole cell lysates from LNCaP expressing Vo/GFP and Cav-1/GFP were blotted using Cav-1 antibody. (C) Whole cell lysates (C) and SV from LNCaP expressing Vo/GFP and Cav-1/GFP were blotted using the indicated antibodies. (D) Quantitative analysis of bleb formation in LNCaP cells overexpressing Vo/GFP and Cav-1/GFP (p=0.03).
Figure 9:
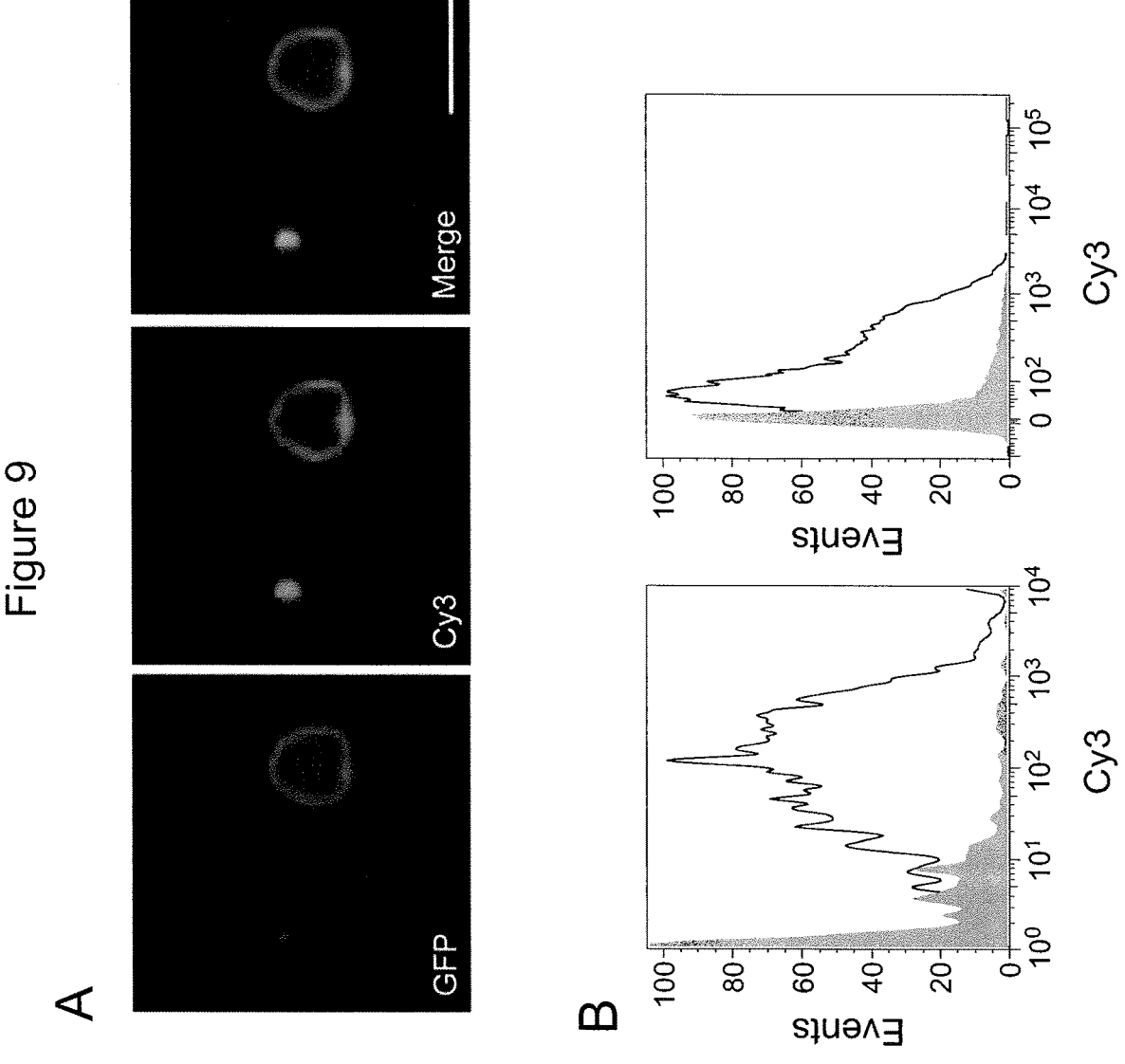
FIG. 9, panels A-B, depicts, in accordance with an embodiment of the invention that particles purified from LNCaP cells overexpressing Cav-1/GFP can be sorted by flow cytometry and visualized by microscopy. (A) Purified particles from LNCaP cells overexpressing Cav-1/GFP were stained with a Cav-1 antibody, sorted by flow cytometry, and examined by microscopy (scale bar: 10 μm). (B) Purified particles from LNCaP cells overexpressing Cav-1/GFP (left) and DU145 cells (right), stained with α-Cav-1, were analyzed by flow cytometry. A Cy3-conjugated secondary antibody was used for detection. Unstained particles were used as a negative control (grey shaded).

To determine whether large oncosomes can be identified using an endogenous tumor progression marker, large shed vesicles were sorted using Cav-1, a validated prostate cancer biomarker found in the circulation of patients with advanced disease (Tahir S A et al., Secreted caveolin-1 stimulates cell survival/clonal growth and contributes to metastasis in androgen-insensitive prostate cancer, Cancer Res 2001, 61:3882-3885). Cav-1 was present in membrane vesicles produced by DU145 cells, suggesting that large shed vesicles are a mobile vehicle for circulating Cav-1 (FIG. 2B). Cav-1-null LNCaP cells stably expressing Cav-1-GFP produced membrane vesicles that were shed and which contained the fluorescent GFP fusion protein (FIG. 8A-C). Enforced expression of Cav-1 in LNCaP cells significantly increased the rate of membrane blebbing and shedding (FIG. 8D), suggesting that Cav-1 may play an active role in vesiculation. The ability to sort Cav-1-GFP-positive particles by FACS in the 1-10 μm size range was validated with a Cav-1-Cy3 antibody, which decorated large oncosome-like GFP-positive vesicles (FIG. 9A). Using the same approach, endogenous Cav-1 in shed vesicle preparations from DU145 cells was detected (FIG. 9B). These results suggest that Cav-1 is a viable target for identifying large oncosomes.

Cav-1-positive vesicles from the plasma of transgenic mice with autochthonous prostate tumors (TRAMP) were sorted. TRAMP prostate tissues express high levels of intra-tumoral Cav-1 (Di Vizio D et al., Caveolin-1 is required for the upregulation of fatty acid synthase (FASN), a tumor promoter, during prostate cancer progression, Cancer Biol Ther 2007, 6:1263-1268; Williams™ et al., Caveolin-1 promotes tumor progression in an autochthonous mouse model of prostate cancer: genetic ablation of Cav-1 delays advanced prostate tumor development in tramp mice, J Biol Chem 2005, 280:25134-25145). Age-matched, non-transgenic littermates were used as controls. Analysis was focused on vesicles of 1-10 μm in diameter. As a validation method, Cav-1-positive vesicles >2-3 μm detected in plasma were sorted by FACS and visualized by direct optical imaging. Vesicles meeting these criteria were detected in plasma from TRAMP mice with prostate cancer, but levels were negligible in plasma of non-transgenic animals and of TRAMP animals with prostate intraepithelial neoplasia (PIN) (FIG. 6A), as confirmed by western blotting (FIG. 6B). These vesicles were substantially more abundant in the circulation of TRAMP mice with lymph node and lung metastases (p=0.03) (FIGS. 6A, C). These results suggest that large oncosomes containing Cav-1 reach the circulation of mice with prostate cancer and their presence can reflect the extent of disease progression. Notably, the presence of Cav-1-positive vesicles <1 μm, which were also detected in the plasma, were not correlated with disease progression in this model (FIG. 6D). Significantly, large oncosome-like vesicles recognized using ARF6 staining were also identified in situ in metastatic TRAMP tumors (FIG. 6E), whereas they were not detected in organ-confined tumors or in benign tissue.

Example 6

In order to understand the degree to which the large oncosomes resemble or are distinct from smaller microvesicles, next generation sequencing (whole genome and RNA-seq) and quantitative proteomics studies (LC-MS/MS SILAC) were performed. The results demonstrated the feasibility of RNA-seq analysis of microvesicles purified from human platelet-poor plasma and have obtained a minimum of 50 million paired end reads per sample. Mapping to RefSeq-annotated human gene loci and quantification as FPKM (fragments per kilobase of exon per million fragments mapped) identified a number of transcripts as differentially expressed between patients with breast cancer and normal subjects (FDR <0.05). Whole genome paired-end sequencing (Illumina) of large oncosome DNA demonstrated that single nucleotide mutations, insertions/deletions, and translocations present in donor cells can be identified in the large oncosome DNA. Stable isotope labeling by amino acids in cell culture (SILAC) profiling of tumor cell-derived large oncosomes in comparison with smaller microvesicles demonstrated enrichment in large oncosomes of cell cycle, anti-apoptosis, and cell motility-associated proteins. Among classes of microvesicle proteins, significant cohorts of the exosome biomarkers were enriched in large oncosomes. These findings identify large oncosomes as a novel class of mircovesicles that harbor clinically relevant biomarkers.

Example 7

This study describes a type of bioactive membrane vesicle previously unrecognized in vivo, which can originate from amoeboid tumor cells. This class of microvesicle is large (~1-10 μm diameter) in comparison to other types of bioactive vesicles (<1 μm), in particular, the substantially smaller exosome-sized vesicles (Duijvesz D et al., Exosomes as biomarker treasure chests for prostate cancer, Eur Urol 2011, 59:823-831) (30-100 nm). Consequently, we propose the term "large oncosome" as a descriptor.

The data herein describes several independent approaches for the detection of large oncosomes in the circulation and in formalin-fixed paraffin embedded (FFPE) sections from mouse models and human tumors. Unlike smaller particles, shown herein is that large oncosome-like structures are visible in tissues using conventional methods, including detection with a clinical biomarker (CK18, FIG. 4D) in FFPE tissue sections, suggesting that a method for detecting these pathologic features could be adapted for routine histopathology. Also described herein is that large oncosomes can be quantified in platelet poor plasma. In several prostate cancer models, as well as in human TMAs and core biopsies, large oncosome-like structures are a feature associated with high Gleason grade and metastatic disease. The results described herein using the LNCaP/MyrAkt1 model, in which the oncosomes can be followed from the point of secretion in tissues to circulation in the blood stream in vivo, support the conclusion that large oncosomes are produced by aggressive tumor cells and gain access to the circulation. The present study focused on prostate cancer models. However, because similar processes occur in other solid tumors, we believe it is likely that similar particles may be detected in other malignancies using comparable approaches.

Figure 6:
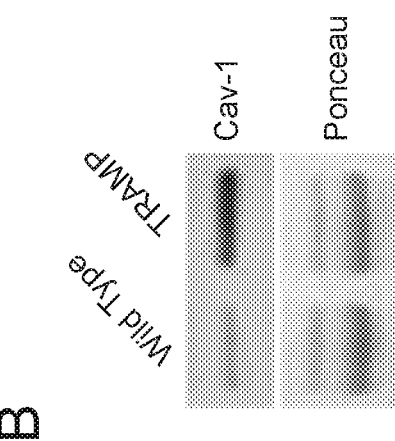
FIG. 6, panels A-E, depicts, in accordance with an embodiment of the invention the large oncosome-like structures containing Cav-1 identify aggressive prostate cancer. (A) FACS analysis of 1-10 μm Cav-1 positive vesicles purified from the plasma of TRAMP mice (n=15) and non-transgenic littermates (WT) (n=10), plotted in a FSC histogram, and analyzed with respect to the diagnostic categories. (B) Large oncosome-like structures, isolated from the plasma of TRAMP and WT mice, were analyzed by western blot. (C) The abundance of Cav-1-positive large oncosome-like structures (1-10 μm) was significantly increased in tumor-bearing mice than in controls p=0.0007, and dramatically correlated with disease progression (almost 30-fold difference between mice with organ-confined tumors vs. mice with lung metastases), p=0.0002. (D) The abundance of Cav-1-positive events <1 μm did not reflect changes across the diagnostic categories. (E) Representative paraffin section of a TRAMP metastatic tumor stained with ARF6 antibody. Arrowheads point to large oncosome-like structures.
Figure 6:
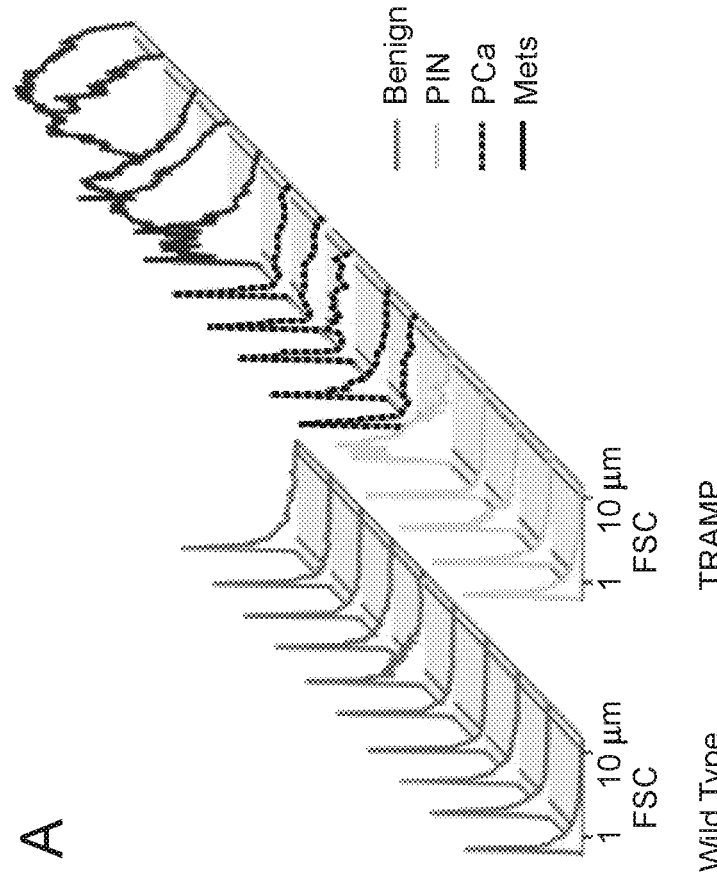
Figure 6:
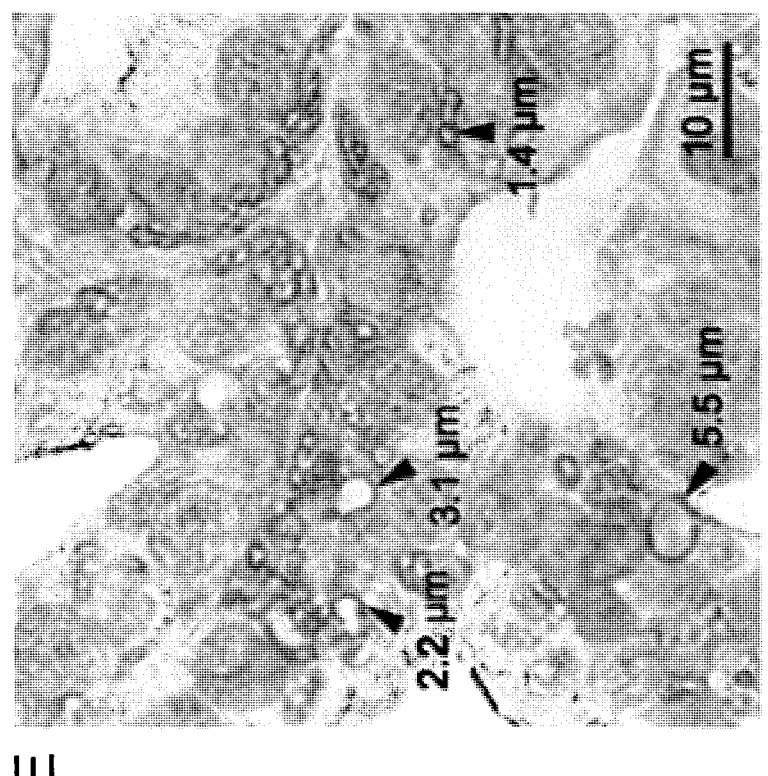
Figure 6:
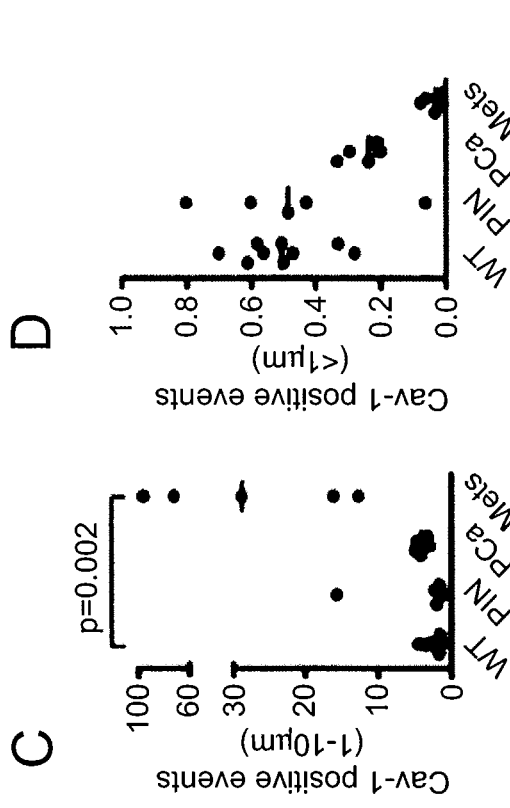

Using specific markers and a FACS method that allowed sorting of vesicles of 1-10 μm diameter and exclusion of aggregates, the results herein show a correlation between the abundance of large oncosomes in the plasma and tumor weight, in mice carrying LNCaP/MyrAkt1 xenograft tumors. In tissues, large vesicles were detected by direct inspection of H&E-stained tumor sections. ARF6 immunostaining facilitated the detection of similar structures in paraffin-embedded tissue, including in $Pten^{PbKO}$/KRAS metastatic prostate tumors, whereas they were not observed in organ-confined $Pten^{PbKO}$ tumors. $Pten^{PbKO}$/KRAS mice develop resistance to androgen ablation, suggesting that quantification of large oncosome-like features may facilitate assessment of tumor aggressiveness at initial presentation or disease progression during therapy. In TRAMP mice, the abundance of Cav-1-positive circulating large oncosome-like structures was highly associated with the presence of metastatic tumors, and similar vesicular structures were observed in paraffin sections only from advanced tumors (FIG. 6). Notably, the number of smaller events (<1 μm) in the circulation of TRAMP mice did not correlate with disease progression.

Using independent cohorts of human prostate cancer tissues, the findings herein demonstrate that the large oncosome features discriminate between tumor and benign tissue, including benign prostatic hyperplasia (BPH), and also between organ-confined and metastatic tumors. Identifying predictive criteria for prostate tumor progression has been extremely problematic, and current paradigms, including PSA levels, Gleason score and clinical stage, are inadequate as predictive tools. In particular, serum PSA can be elevated in benign conditions such as inflammation and BPH. Collectively, these observations indicate that assessment of large oncosome features in tumor sections or in the circulation may inform clinical evaluation. Identification of proteins other than Cav-1 and ARF6 in oncosomes, as well as discrete RNA species, may result in additional biomarker tools applicable to clinical medicine. Cav-1 is expressed by normal endothelial cells and has been identified as a constituent of circulating nanovesicles. For this reason, it is possible that gating particle size above 1 μm when Cav-1 is used as a sorting marker will provide information about disease course that collection of smaller TMV may not.

Quantitation of circulating tumor cells (CTCs) is currently being evaluated to assess the risk of disease progression for prostate and other types of cancer. However, the clinical significance of CTCs remains to be established because of their extremely small number in peripheral blood as compared with the number of blood cells (Park Y, et al., Expected clinical applications of circulating tumor cells in breast cancer, World J Clin Oncol 2011, 2:303-310). We have demonstrated that large oncosome-like structures can be separated from plasma in a manner that does not require the capture of CTCs or other cells. The molecular characterization of large oncosomes may potentially offer a more sensitive and specific 'liquid biopsy' than CTCs for patient selection, monitoring of treatment efficacy and assessment of drug-resistance.

TABLE 1

| Examples of cancer genes | | | | |
| --- | --- | --- | --- | --- |
| Gene | Description | Chr | Chr Band | Tumor Types |
| ABL1 | v-abl Abelson murine leukemia viral oncogene homolog 1 | 9 | 9q34.1 | CML, ALL, T-ALL |
| ABL2 | v-abl Abelson murine leukemia viral oncogene homolog 2 | 1 | 1q24-q25 | AML |
| ACSL3 | acyl-CoA synthetase long-chain family member 3 | 2 | 2q36 | prostate |
| AF15Q14 | AF15q14 protein | 15 | 15q14 | AML |
| AF1Q | ALL1-fused gene from chromosome 1q | 1 | 1q21 | ALL |
| AF3p21 | SH3 protein interacting with Nck, 90 kDa (ALL1 fused gene from 3p21) | 3 | 3p21 | ALL |
| AF5q31 | ALL1 fused gene from 5q31 | 5 | 5q31 | ALL |
| AKAP9 | A kinase (PRKA) anchor protein (yotiao) 9 | 7 | 7q21-q22 | papillary thyroid |
| AKT1 | v-akt murine thymoma viral oncogene homolog 1 | 14 | 14q32.32 | breast, colorectal, ovarian, NSCLC |
| AKT2 | v-akt murine thymoma viral oncogene homolog 2 | 19 | 19q13.1-q13.2 | ovarian, pancreatic |
| ALDH2 | aldehyde dehydrogenase 2 family (mitochondrial) | 12 | 12q24.2 | leiomyoma |
| ALK | anaplastic lymphoma kinase (Ki-1) | 2 | 2p23 | ALCL, NSCLC, neuroblastoma |
| ALO17 | KIAA1618 protein | 17 | 17q25.3 | ALCL |
| APC | adenomatous polyposis of the colon gene | 5 | 5q21 | colorectal, pancreatic, desmoid, hepatoblastoma, glioma, other CNS |

TABLE 1-continued

| | Examples of cancer genes | | | |
|---|---|---|---|---|
| Gene | Description | Chr | Chr Band | Tumor Types |
| ARHGEF12 | RHO guanine nucleotide exchange factor (GEF) 12 (LARG) | 11 | 11q23.3 | AML |
| ARHH | RAS homolog gene family, member H (TTF) | 4 | 4p13 | NHL |
| ARID1A | AT rich interactive domain 1A (SWI-like) | 1 | 1p35.3 | clear cell ovarian carcinoma, RCC |
| ARID2 | AT rich interactive domain 2 | 12 | 12q12 | hepatocellular carcinoma |
| ARNT | aryl hydrocarbon receptor nuclear translocator | 1 | 1q21 | AML |
| ASPSCR1 | alveolar soft part sarcoma chromosome region, candidate 1 | 17 | 17q25 | alveolar soft part sarcoma |
| ASXL1 | additional sex combs like 1 | 20 | 20q11.1 | MDS, CMML |
| ATF1 | activating transcription factor 1 | 12 | 12q13 | malignant melanoma of soft parts, angiomatoid fibrous histiocytoma |
| ATIC | 5-aminoimidazole-4-carboxamide ribonucleotide formyltransferase/IMP cyclohydrolase | 2 | 2q35 | ALCL |
| ATM | ataxia telangiectasia mutated | 11 | 11q22.3 | T-PLL |
| ATRX | alpha thalassemia/mental retardation syndrome X-linked | X | Xq21.1 | Pancreatic neuroendocrine tumours, paediatric GBM |
| AXIN1 | axin 1 | 16 | 16p13.3 | colorectal, endometrial, prostate and hepatocellular carcinomas, hepatoblastoma, sporadic medulloblastoma |
| BAP1 | BRCA1 associated protein-1 (ubiquitin carboxy-terminal hydrolase) | 3 | 3p21.31-p21.2 | uveal melanoma, breast, NSCLC, RCC |
| BCL10 | B-cell CLL/lymphoma 10 | 1 | 1p22 | MALT |
| BCL11A | B-cell CLL/lymphoma 11A | 2 | 2p13 | B-CLL |
| BCL11B | B-cell CLL/lymphoma 11B (CTIP2) | 14 | 14q32.1 | T-ALL |
| BCL2 | B-cell CLL/lymphoma 2 | 18 | 18q21.3 | NHL, CLL |
| BCL3 | B-cell CLL/lymphoma 3 | 19 | 19q13 | CLL |
| BCL5 | B-cell CLL/lymphoma 5 | 17 | 17q22 | CLL |
| BCL6 | B-cell CLL/lymphoma 6 | 3 | 3q27 | NHL, CLL |
| BCL7A | B-cell CLL/lymphoma 7A | 12 | 12q24.1 | BNHL |
| BCL9 | B-cell CLL/lymphoma 9 | 1 | 1q21 | B-ALL |
| BCOR | BCL6 corepressor | X | Xp11.4 | retinoblastoma, AML, APL (translocation) |
| BCR | breakpoint cluster region | 22 | 22q11.21 | CML, ALL, AML |
| BHD | folliculin, Birt-Hogg-Dube syndrome | 17 | 17p11.2 | |
| BIRC3 | baculoviral IAP repeat-containing 3 | 11 | 11q22-q23 | MALT |
| BLM | Bloom Syndrome | 15 | 15q26.1 | |
| BMPR1A | bone morphogenetic protein receptor, type IA | 10 | 10q22.3 | |
| BRAF | v-raf murine sarcoma viral oncogene homolog B1 | 7 | 7q34 | melanoma, colorectal, papillary thyroid, borderline ovarian, NSCLC, cholangiocarcinoma, pilocytic astrocytoma |
| BRCA1 | familial breast/ovarian cancer gene 1 | 17 | 17q21 | ovarian |
| BRCA2 | familial breast/ovarian cancer gene 2 | 13 | 13q12 | breast, ovarian, pancreatic |
| BRD3 | bromodomain containing 3 | 9 | 9q34 | lethal midline carcinoma of young people |
| BRD4 | bromodomain containing 4 | 19 | 19p13.1 | lethal midline carcinoma of young people |
| BRIP1 | BRCA1 interacting protein C-terminal helicase 1 | 17 | 17q22 | |
| BTG1 | B-cell translocation gene 1, anti-proliferative | 12 | 12q22 | BCLL |
| BUB1B | BUB1 budding uninhibited by benzimidazoles 1 homolog beta (yeast) | 15 | 15q15 | |

TABLE 1-continued

| | Examples of cancer genes | | | |
|---|---|---|---|---|
| Gene | Description | Chr | Chr Band | Tumor Types |
| C12orf9 | chromosome 12 open reading frame 9 | 12 | 12q14.3 | lipoma |
| C15orf21 | chromosome 15 open reading frame 21 | 15 | 15q21.1 | prostate |
| C15orf55 | chromosome 15 open reading frame 55 | 15 | 15q14 | lethal midline carcinoma |
| C16orf75 | chromosome 16 open reading frame 75 | 16 | 16p13.13 | PMBL, Hodgkin lymphoma |
| C2orf44 | chromosome 2 open reading frame 44 | 2 | 2p23.3 | NSCLC |
| CAMTA1 | calmodulin binding transcription activator 1 | 1 | 1p36.31-p36.23 | epithelioid haemangioendothelioma |
| CANT1 | calcium activated nucleotidase 1 | 17 | 17q25 | prostate |
| CARD11 | caspase recruitment domain family, member 11 | 7 | 7p22 | DLBCL |
| CARS | cysteinyl-tRNA synthetase | 11 | 11p15.5 | ALCL |
| CBFA2T1 | core-binding factor, runt domain, alpha subunit 2; translocated to, 1 (ETO) | 8 | 8q22 | AML |
| CBFA2T3 | core-binding factor, runt domain, alpha subunit 2; translocated to, 3 (MTG-16) | 16 | 16q24 | AML |
| CBFB | core-binding factor, beta subunit | 16 | 16q22 | AML |
| CBL | Cas-Br-M (murine) ecotropic retroviral transforming | 11 | 11q23.3 | AML, JMML, MDS |
| CBLB | Cas-Br-M (murine) ecotropic retroviral transforming sequence b | 3 | 3q13.11 | AML |
| CBLC | Cas-Br-M (murine) ecotropic retroviral transforming sequence c | 19 | 19q13.2 | AML |
| CCDC6 | coiled-coil domain containing 6 | 10 | 10q21 | NSCLC |
| CCNB1IP1 | cyclin B1 interacting protein 1, E3 ubiquitin protein ligase | 14 | 14q11.2 | leiomyoma |
| CCND1 | cyclin D1 | 11 | 11q13 | CLL, B-ALL, breast |
| CCND2 | cyclin D2 | 12 | 12p13 | NHL, CLL |
| CCND3 | cyclin D3 | 6 | 6p21 | MM |
| CCNE1 | cyclin E1 | 19 | 19q12 | serous ovarian |
| CD273 | programmed cell death 1 ligand 2 | 9 | 9p24.2 | PMBL, Hodgkin lymphoma |
| CD274 | CD274 molecule | 9 | 9p24 | PMBL, Hodgkin lymphoma |
| CD74 | CD74 molecule, major histocompatibility complex, class II invariant chain | 5 | 5q32 | NSCLC |
| CD79A | CD79a molecule, immunoglobulin-associated alpha | 19 | 19q13.2 | DLBCL |
| CD79B | CD79b molecule, immunoglobulin-associated beta | 17 | 17q23 | DLBCL |
| CDH1 | cadherin 1, type 1, E-cadherin (epithelial) (ECAD) | 16 | 16q22.1 | lobular breast, gastric |
| CDH11 | cadherin 11, type 2, OB-cadherin (osteoblast) | 16 | 16q22.1 | aneurysmal bone cyst |
| CDK12 | cyclin-dependent kinase 12 | 17 | 17q12 | serous ovarian |
| CDK4 | cyclin-dependent kinase 4 | 12 | 12q14 | |
| CDK6 | cyclin-dependent kinase 6 | 7 | 7q21-q22 | ALL |
| CDKN2A | cyclin-dependent kinase inhibitor 2A (p16(INK4a)) gene | 9 | 9p21 | melanoma, multiple other tumour types |
| CDKN2a(p14) | cyclin-dependent kinase inhibitor 2A-- p14ARF protein | 9 | 9p21 | melanoma, multiple other tumour types |
| CDKN2C | cyclin-dependent kinase inhibitor 2C (p18, inhibits CDK4) | 1 | 1p32 | glioma, MM |
| CDX2 | caudal type homeo box transcription factor 2 | 13 | 13q12.3 | AML |

TABLE 1-continued

| Gene | Description | Chr | Chr Band | Tumor Types |
|---|---|---|---|---|
| | Examples of cancer genes | | | |
| CEBPA | CCAAT/enhancer binding protein (C/EBP), alpha | 19 | 19q13.1 | AML, MDS |
| CEP1 | centrosomal protein 1 | 9 | 9q33 | MPD, NHL |
| CHCHD7 | coiled-coil-helix-coiled-coil-helix domain containing 7 | 8 | 8q11.2 | salivary gland adenoma |
| CHEK2 | CHK2 checkpoint homolog (*S. pombe*) | 22 | 22q12.1 | |
| CHIC2 | cysteine-rich hydrophobic domain 2 | 4 | 4q11-q12 | AML |
| CHN1 | chimerin (chimaerin) 1 | 2 | 2q31-q32.1 | extraskeletal myxoid chondrosarcoma |
| CIC | capicua homolog | 19 | 19q13.2 | oligodendroglioma, soft tissue sarcoma |
| CIITA | class II, major histocompatibility complex, transactivator | 16 | 16p13 | PMBL, Hodgkin lymphoma |
| CLTC | clathrin, heavy polypeptide (Hc) | 17 | 17q11-qter | ALCL, renal |
| CLTCL1 | clathrin, heavy polypeptide-like 1 | 22 | 22q11.21 | ALCL |
| CMKOR1 | chemokine orphan receptor 1 | 2 | 2q37.3 | lipoma |
| CNOT3 | CCR4-NOT transcription complex subunit 3 | 19 | 19q13.4 | T-ALL |
| COL1A1 | collagen, type I, alpha 1 | 17 | 17q21.31-q22 | dermatofibrosarcoma protuberans, aneurysmal bone cyst |
| COPEB | core promoter element binding protein (KLF6) | 10 | 10p15 | prostate, glioma |
| COX6C | cytochrome c oxidase subunit Vic | 8 | 8q22-q23 | uterine leiomyoma |
| CREB1 | cAMP responsive element binding protein 1 | 2 | 2q34 | clear cell sarcoma, angiomatoid fibrous histiocytoma |
| CREB3L1 | cAMP responsive element binding protein 3-like 1 | 11 | 11p11.2 | myxofibrosarcoma |
| CREB3L2 | cAMP responsive element binding protein 3-like 2 | 7 | 7q34 | fibromyxoid sarcoma |
| CREBBP | CREB binding protein (CBP) | 16 | 16p13.3 | ALL, AML, DLBCL, B-NHL |
| CRLF2 | cytokine receptor-like factor 2 | X, Y | Xp22.3; Yp11.3 | B-ALL, Downs associated ALL |
| CRTC3 | CREB regulated transcription coactivator 3 | 15 | 15q26.1 | salivary gland mucoepidermoid |
| CTNNB1 | catenin (cadherin-associated protein), beta 1 | 3 | 3p22-p21.3 | colorectal, ovarian, hepatoblastoma, pleomorphic salivary gland adenoma, other tumour types |
| CYLD | familial cylindromatosis gene | 16 | 16q12-q13 | cylindroma |
| D10S170 | DNA segment on chromosome 10 (unique) 170, H4 gene (PTC1) | 10 | 10q21 | papillary thyroid, CML |
| DAXX | death-domain associated protein | 6 | 6p21.3 | pancreatic neuroendocrine tumour, paediatric glioblastoma |
| DDB2 | damage-specific DNA binding protein 2 | 11 | 11p12 | |
| DDIT3 | DNA-damage-inducible transcript 3 | 12 | 12q13.1-q13.2 | liposarcoma |
| DDX10 | DEAD (Asp-Glu-Ala-Asp) box polypeptide 10 | 11 | 11q22-q23 | AML* |
| DDX5 | DEAD (Asp-Glu-Ala-Asp) box polypeptide 5 | 17 | 17q21 | prostate |
| DDX6 | DEAD (Asp-Glu-Ala-Asp) box polypeptide 6 | 11 | 11q23.3 | B-NHL |
| DEK | DEK oncogene (DNA binding) | 6 | 6p23 | AML |
| DICER1 | dicer 1, ribonuclease type III | 14 | 14q32.13 | sex cord-stromal tumour, TGCT, embryonal rhabdomyosarcoma |
| DNM2 | dynamin 2 | 19 | 19p13.2 | ETP ALL |
| DNMT3A | DNA (cytosine-5-)-methyltransferase 3 alpha | 2 | 2p23 | AML |

TABLE 1-continued

| | Examples of cancer genes | | | |
| --- | --- | --- | --- | --- |
| Gene | Description | Chr | Chr Band | Tumor Types |
| DUX4 | double homeobox, 4 | 4 | 4q35 | soft tissue sarcoma |
| EBF1 | early B-cell factor 1 | 5 | 5q34 | lipoma |
| ECT2L | epithelial cell transforming sequence 2 oncogene-like | 6 | 6q24.1 | ETP ALL |
| EGFR | epidermal growth factor receptor (erythroblastic leukemia viral (v-erb-b) oncogene homolog, avian) | 7 | 7p12.3-p12.1 | glioma, NSCLC |
| EIF4A2 | eukaryotic translation initiation factor 4A, isoform 2 | 3 | 3q27.3 | NHL |
| ELF4 | E74-like factor 4 (ets domain transcription factor) | X | Xq26 | AML |
| ELK4 | ELK4, ETS-domain protein (SRF accessory protein 1) | 1 | 1q32 | prostate |
| ELKS | ELKS protein | 12 | 12p13.3 | papillary thyroid |
| ELL | ELL gene (11-19 lysine-rich leukemia gene) | 19 | 19p13.1 | AL |
| ELN | elastin | 7 | 7q11.23 | B-ALL |
| EML4 | echinoderm microtubule associated protein like 4 | 2 | 2p21 | NSCLC |
| EP300 | 300 kd E1A-Binding protein gene | 22 | 22q13 | colorectal, breast, pancreatic, AML, ALL, DLBCL |
| EPS15 | epidermal growth factor receptor pathway substrate 15 (AF1p) | 1 | 1p32 | ALL |
| ERBB2 | v-erb-b2 erythroblastic leukemia viral oncogene homolog 2, neuro/glioblastoma derived oncogene homolog (avian) | 17 | 17q21.1 | breast, ovarian, other tumour types, NSCLC, gastric |
| ERCC2 | excision repair cross-complementing rodent repair deficiency, complementation group 2 (xeroderma pigmentosum D) | 19 | 19q13.2-q13.3 | |
| ERCC3 | excision repair cross-complementing rodent repair deficiency, complementation group 3 (xeroderma pigmentosum group B complementing) | 2 | 2q21 | |
| ERCC4 | excision repair cross-complementing rodent repair deficiency, complementation group 4 | 16 | 16p13.3-p13.13 | |
| ERCC5 | excision repair cross-complementing rodent repair deficiency, complementation group 5 (xeroderma pigmentosum, complementation group G (Cockayne syndrome)) | 13 | 13q33 | |
| ERG | v-ets erythroblastosis virus E26 oncogene like (avian) | 21 | 21q22.3 | Ewing sarcoma, prostate, AML |
| ETV1 | ets variant gene 1 | 7 | 7p22 | Ewing sarcoma, prostate |
| ETV4 | ets variant gene 4 (E1A enhancer binding protein, E1AF) | 17 | 17q21 | Ewing sarcoma, prostate carcinoma |
| ETV5 | ets variant gene 5 | 3 | 3q28 | prostate |
| ETV6 | ets variant gene 6 (TEL oncogene) | 12 | 12p13 | congenital fibrosarcoma, multiple leukaemia and lymphoma, secretory breast, MDS, ALL |
| EVI1 | ecotropic viral integration site 1 | 3 | 3q26 | AML, CML |
| EWSR1 | Ewing sarcoma breakpoint region 1 (EWS) | 22 | 22q12 | Ewing sarcoma, desmoplastic small round cell tumour, ALL, clear cell sarcoma, sarcoma, myoepithelioma |

TABLE 1-continued

Examples of cancer genes

| Gene | Description | Chr | Chr Band | Tumor Types |
|---|---|---|---|---|
| EXT1 | multiple exostoses type 1 gene | 8 | 8q24.11-q24.13 | |
| EXT2 | multiple exostoses type 2 gene | 11 | 11p12-p11 | |
| EZH2 | enhancer of zeste homolog 2 | 7 | 7q35-q36 | DLBCL |
| EZR | ezrin | 6 | 6q25.3 | NSCLC |
| FACL6 | fatty-acid-coenzyme A ligase, long-chain 6 | 5 | 5q31 | AML, AEL |
| FAM22A | family with sequence similarity 22, member A | 10 | 10q23.2 | endometrial stromal sarcoma |
| FAM22B | family with sequence similarity 22, member B | 10 | 10q22.3 | endometrial stromal sarcoma |
| FAM46C | family with sequence similarity 46, member C | 1 | 1p12 | MM |
| FANCA | Fanconi anemia, complementation group A | 16 | 16q24.3 | |
| FANCC | Fanconi anemia, complementation group C | 9 | 9q22.3 | |
| FANCD2 | Fanconi anemia, complementation group D2 | 3 | 3p26 | |
| FANCE | Fanconi anemia, complementation group E | 6 | 6p21-p22 | |
| FANCF | Fanconi anemia, complementation group F | 11 | 11p15 | |
| FANCG | Fanconi anemia, complementation group G | 9 | 9p13 | |
| FBXO11 | F-box protein 11 | 2 | 2p16.3 | DLBCL |
| FBXW7 | F-box and WD-40 domain protein 7 (archipelago homolog, *Drosophila*) | 4 | 4q31.3 | colorectal, endometrial, T-ALL |
| FCGR2B | Fc fragment of IgG, low affinity IIb, receptor for (CD32) | 1 | 1q23 | ALL |
| FEV | FEV protein - (HSRNAFEV) | 2 | 2q36 | Ewing sarcoma |
| FGFR1 | fibroblast growth factor receptor 1 | 8 | 8p11.2-p11.1 | MPD, NHL |
| FGFR1OP | FGFR1 oncogene partner (FOP) | 6 | 6q27 | MPD, NHL |
| FGFR2 | fibroblast growth factor receptor 2 | 10 | 10q26 | gastric, NSCLC, endometrial |
| FGFR3 | fibroblast growth factor receptor 3 | 4 | 4p16.3 | bladder, MM, T-cell lymphoma |
| FH | fumarate hydratase | 1 | 1q42.1 | |
| FHIT | fragile histidine triad gene | 3 | 3p14.2 | pleomorphic salivary gland adenoma |
| FIP1L1 | FIP1 like 1 (*S. cerevisiae*) | 4 | 4q12 | idiopathic hypereosinophilic syndrome |
| FLI1 | Friend leukemia virus integration 1 | 11 | 11q24 | Ewing sarcoma |
| FLJ27352 | BX648577, FLJ27352 hypothetical LOC145788 | 15 | 15q21.3 | PMBL, Hodgkin lymphoma |
| FLT3 | fms-related tyrosine kinase 3 | 13 | 13q12 | AML, ALL |
| FNBP1 | formin binding protein 1 (FBP17) | 9 | 9q23 | AML |
| FOXL2 | forkhead box L2 | 3 | 3q23 | granulosa-cell tumour of the ovary |
| FOXO1A | forkhead box O1A (FKHR) | 13 | 13q14.1 | alveolar rhabdomyosarcoma |
| FOXO3A | forkhead box O3A | 6 | 6q21 | AL |
| FOXP1 | forkhead box P1 | 3 | 3p14.1 | ALL |
| FSTL3 | follistatin-like 3 (secreted glycoprotein) | 19 | 19p13 | B-CLL |
| FUBP1 | far upstream element (FUSE) binding protein 1 | 1 | 1p13.1 | oligodendroglioma |
| FUS | fusion, derived from t(12; 16) malignant liposarcoma | 16 | 16p11.2 | liposarcoma, AML, Ewing sarcoma, angiomatoid fibrous histiocytoma, fibromyxoid sarcoma |
| FVT1 | follicular lymphoma variant translocation 1 | 18 | 18q21.3 | B-NHL |

TABLE 1-continued

Examples of cancer genes

| Gene | Description | Chr | Chr Band | Tumor Types |
|---|---|---|---|---|
| GAS7 | growth arrest-specific 7 | 17 | 17p | AML* |
| GATA1 | GATA binding protein 1 (globin transcription factor 1) | X | Xp11.23 | megakaryoblastic leukaemia of Downs syndrome |
| GATA2 | GATA binding protein 2 | 3 | 3q21.3 | AML (CML blast transformation) |
| GATA3 | GATA binding protein 3 | 10 | 10p15 | breast |
| GMPS | guanine monphosphate synthetase | 3 | 3q24 | AML |
| GNA11 | guanine nucleotide binding protein (G protein), alpha 11 (Gq class) | 19 | 19p13.3 | uveal melanoma |
| GNAQ | guanine nucleotide binding protein (G protein), q polypeptide | 9 | 9q21 | uveal melanoma |
| GNAS | guanine nucleotide binding protein (G protein), alpha stimulating activity polypeptide 1 | 20 | 20q13.2 | pituitary adenoma |
| GOLGA5 | golgi autoantigen, golgin subfamily a, 5 (PTC5) | 14 | 14q | papillary thyroid |
| GOPC | golgi associated PDZ and coiled-coil motif containing | 6 | 6q21 | glioblastoma |
| GPC3 | glypican 3 | X | Xq26.1 | |
| GPHN | gephyrin (GPH) | 14 | 14q24 | AL |
| GRAF | GTPase regulator associated with focal adhesion kinase pp125(FAK) | 5 | 5q31 | AML, MDS |
| H3F3A | H3 histone, family 3 A | 1 | 1q42.12 | glioma |
| HCMOGT-1 | sperm antigen HCMOGT-1 | 17 | 17p11.2 | JMML |
| HEAB | ATP_GTP binding protein | 11 | 11q12 | AML |
| HERPUD1 | homocysteine-inducible, endoplasmic reticulum stress-inducible, ubiquitin-like domain member 1 | 16 | 16q12.2-q13 | prostate |
| HEY1 | hairy/enhancer-of-split related with YRPW motif 1 | 8 | 8q21 | mesenchymal chondrosarcoma |
| HIP1 | huntingtin interacting protein 1 | 7 | 7q11.23 | CMML |
| HIST1H3B | histone cluster 1, H3b | 6 | 6p22.1 | glioma |
| HIST1H4I | histone 1, H4i (H4FM) | 6 | 6p21.3 | NHL |
| HLF | hepatic leukemia factor | 17 | 17q22 | ALL |
| HLXB9 | homeo box HB9 | 7 | 7q36 | AML |
| HMGA1 | high mobility group AT-hook 1 | 6 | 6p21 | microfollicular thyroid adenoma, various benign mesenchymal tumours |
| HMGA2 | high mobility group AT-hook 2 (HMGIC) | 12 | 12q15 | lipoma, leiomyoma, pleomorphic salivary gland adenoma |
| HNRNPA2B1 | heterogeneous nuclear ribonucleoprotein A2/B1 | 7 | 7p15 | prostate |
| HOOK3 | hook homolog 3 | 8 | 8p11.21 | papillary thyroid |
| HOXA11 | homeo box A11 | 7 | 7p15-p14.2 | CML |
| HOXA13 | homeo box A13 | 7 | 7p15-p14.2 | AML |
| HOXA9 | homeo box A9 | 7 | 7p15-p14.2 | AML* |
| HOXC11 | homeo box C11 | 12 | 12q13.3 | AML |
| HOXC13 | homeo box C13 | 12 | 12q13.3 | AML |
| HOXD11 | homeo box D11 | 2 | 2q31-q32 | AML |
| HOXD13 | homeo box D13 | 2 | 2q31-q32 | AML* |
| HRAS | v-Ha-ras Harvey rat sarcoma viral oncogene homolog | 11 | 11p15.5 | infrequent sarcomas, rare other tumour types |
| HRPT2 | hyperparathyroidism 2 | 1 | 1q21-q31 | parathyroid adenoma |
| HSPCA | heat shock 90 kDa protein 1, alpha | 14 | 14q32.31 | NHL |
| HSPCB | heat shock 90 kDa protein 1, beta | 6 | 6p12 | NHL |
| IDH1 | isocitrate dehydrogenase 1 (NADP+), soluble | 2 | 2q33.3 | glioblastoma |
| IDH2 | socitrate dehydrogenase 2 (NADP+), mitochondrial | 15 | 15q26.1 | glioblastoma |
| IGH@ | immunoglobulin heavy locus | 14 | 14q32.33 | MM, Burkitt lymphoma, NHL, CLL, B-ALL, MALT, MLCLS |
| IGK@ | immunoglobulin kappa locus | 2 | 2p12 | Burkitt lymphoma, B-NHL |

TABLE 1-continued

| | Examples of cancer genes | | | |
|---|---|---|---|---|
| Gene | Description | Chr | Chr Band | Tumor Types |
| IGL@ | immunoglobulin lambda locus | 22 | 22q11.1-q11.2 | Burkitt lymphoma |
| IKZF1 | IKAROS family zinc finger 1 | 7 | 7p12.2 | ALL, DLBCL |
| IL2 | interleukin 2 | 4 | 4q26-q27 | intestinal T-cell lymphoma |
| IL21R | interleukin 21 receptor | 16 | 16p11 | NHL |
| IL6ST | interleukin 6 signal transducer (gp130, oncostatin M receptor) | 5 | 5q11 | hepatocellular carcinoma |
| IL7R | interleukin 7 receptor | 5 | 5p13 | ALL, ETP ALL |
| IRF4 | interferon regulatory factor 4 | 6 | 6p25-p23 | MM |
| IRTA1 | immunoglobulin superfamily receptor translocation associated 1 | 1 | 1q21 | B-NHL |
| ITK | IL2-inducible T-cell kinase | 5 | 5q31-q32 | peripheral T-cell lymphoma |
| JAK1 | Janus kinase 1 | 1 | 1p32.3-p31.3 | ALL |
| JAK2 | Janus kinase 2 | 9 | 9p24 | ALL, AML, MPD, CML |
| JAK3 | Janus kinase 3 | 19 | 19p13.1 | acute megakaryocytic leukaemia, ETP ALL |
| JAZF1 | juxtaposed with another zinc finger gene 1 | 7 | 7p15.2-p15.1 | endometrial stromal tumour |
| JUN | jun oncogene | 1 | 1p32-p31 | sarcoma |
| KCNJ5 | potassium inwardly-rectifying channel, subfamily J, member 5 | 11 | 11q24 | adrenal |
| KDM5A | lysine (K)-specific demethylase 5A, JARID1A | 12 | 12p11 | AML |
| KDM5C | lysine (K)-specific demethylase 5C (JARID1C) | X | Xp11.22-p11.21 | clear cell renal carcinoma |
| KDM6A | lysine (K)-specific demethylase 6A, UTX | X | Xp11.2 | renal, oesophageal SCC, MM |
| KDR | vascular endothelial growth factor receptor 2 | 4 | 4q11-q12 | NSCLC, angiosarcoma |
| KIAA1549 | KIAA1549 | 7 | 7q34 | pilocytic astrocytoma |
| KIF5B | kinesin family member 5B | 10 | 10p11.22 | NSCLC |
| KIT | v-kit Hardy-Zuckerman 4 feline sarcoma viral oncogene homolog | 4 | 4q12 | GIST, AML, TGCT, mastocytosis, mucosal melanoma |
| KLF4 | Kruppel-like factor 4 | 9 | 9q31 | meningioma |
| KLK2 | kallikrein-related peptidase 2 | 19 | 19q13.41 | prostate |
| KRAS | v-Ki-ras2 Kirsten rat sarcoma 2 viral oncogene homolog | 12 | 12p12.1 | pancreatic, colorectal, lung, thyroid, AML, other tumour types |
| KTN1 | kinectin 1 (kinesin receptor) | 14 | 14q22.1 | papillary thyroid |
| LAF4 | lymphoid nuclear protein related to AF4 | 2 | 2q11.2-q12 | ALL, T-ALL |
| LASP1 | LIM and SH3 protein 1 | 17 | 17q11-q21.3 | AML |
| LCK | lymphocyte-specific protein tyrosine kinase | 1 | 1p35-p34.3 | T-ALL |
| LCP1 | lymphocyte cytosolic protein 1 (L-plastin) | 13 | 13q14.1-q14.3 | NHL |
| LCX | leukemia-associated protein with a CXXC domain | 10 | 10q21 | AML |
| LHFP | lipoma HMGIC fusion partner | 13 | 13q12 | lipoma |
| LIFR | leukemia inhibitory factor receptor | 5 | 5p13-p12 | salivary adenoma |
| LMO1 | LIM domain only 1 (rhombotin 1)(RBTN1) | 11 | 11p15 | T-ALL, neuroblastoma |
| LMO2 | LIM domain only 2 (rhombotin-like 1)(RBTN2) | 11 | 11p13 | T-ALL |
| LPP | LIM domain containing preferred translocation partner in lipoma | 3 | 3q28 | lipoma, leukaemia |
| LRIG3 | leucine-rich repeats and immunoglobulin-like domains 3 | 12 | 12q14.1 | NSCLC |
| LYL1 | lymphoblastic leukemia derived sequence 1 | 19 | 19p13.2-p13.1 | T-ALL |
| MADH4 | Homolog of *Drosophila* Mothers Against Decapentaplegic 4 gene | 18 | 18q21.1 | colorectal, pancreatic, small intestine |

TABLE 1-continued

| | Examples of cancer genes | | | |
| --- | --- | --- | --- | --- |
| Gene | Description | Chr | Chr Band | Tumor Types |
| MAF | v-maf musculoaponeurotic fibrosarcoma oncogene homolog | 16 | 16q22-q23 | MM |
| MAFB | v-maf musculoaponeurotic fibrosarcoma oncogene homolog B (avian) | 20 | 20q11.2-q13.1 | MM |
| MALT1 | mucosa associated lymphoid tissue lymphoma translocation gene 1 | 18 | 18q21 | MALT |
| MAML2 | mastermind-like 2 (*Drosophila*) | 11 | 11q22-q23 | salivary gland mucoepidermoid |
| MAP2K1 | mitogen-activated protein kinase 1 | 15 | 15q22.1-q22.33 | NSCLC, melanoma, colorectal |
| MAP2K2 | mitogen-activated protein kinase 2 | 19 | 19p13.3 | NSCLC, melanoma |
| MAP2K4 | mitogen-activated protein kinase 4 | 17 | 17p11.2 | pancreatic, breast, colorectal |
| MAX | Myc associated factor X | 14 | 14q23 | pheochromocytoma |
| MDM2 | Mdm2 p53 binding protein homolog | 12 | 12q15 | sarcoma, glioma, colorectal, other tumour types |
| MDM4 | Mdm4 p53 binding protein homolog | 1 | 1q32 | glioblastoma, bladder, retinoblastoma |
| MDS1 | myelodysplasia syndrome 1 | 3 | 3q26 | MDS, AML |
| MDS2 | myelodysplastic syndrome 2 | 1 | 1p36 | MDS |
| MECT1 | mucoepidermoid translocated 1 | 19 | 19p13 | salivary gland mucoepidermoid |
| MED12 | mediator complex subunit 12 | X | Xq13 | uterine leiomyoma |
| MEN1 | multiple endocrine neoplasia type 1 gene | 11 | 11q13 | parathyroid tumours, pancreatic neuroendocrine tumour |
| MET | met proto-oncogene (hepatocyte growth factor receptor) | 7 | 7q31 | papillary renal, head-neck squamous cell |
| MITF | microphthalmia-associated transcription factor | 3 | 3p14.1 | melanoma |
| MKL1 | megakaryoblastic leukemia (translocation) 1 | 22 | 22q13 | acute megakaryocytic leukaemia |
| MLF1 | myeloid leukemia factor 1 | 3 | 3q25.1 | AML |
| MLH1 | *E. coli* MutL homolog gene | 3 | 3p21.3 | colorectal, endometrial, ovarian, CNS |
| MLL | myeloid/lymphoid or mixed-lineage leukemia (trithorax homolog, *Drosophila*) | 11 | 11q23 | AML, ALL |
| MLL2 | myeloid/lymphoid or mixed-lineage leukemia 2 | 12 | 12q12-q14 | medulloblastoma, renal |
| MLL3 | myeloid/lymphoid or mixed-lineage leukemia 3 | 7 | 7q36.1 | medulloblastoma |
| MLLT1 | myeloid/lymphoid or mixed-lineage leukemia (trithorax homolog, *Drosophila*); translocated to, 1 (ENL) | 19 | 19p13.3 | AL |
| MLLT10 | myeloid/lymphoid or mixed-lineage leukemia (trithorax homolog, *Drosophila*); translocated to, 10(AF10) | 10 | 10p12 | AL |
| MLLT2 | myeloid/lymphoid or mixed-lineage leukemia (trithorax homolog, *Drosophila*); translocated to, 2 (AF4) | 4 | 4q21 | AL |
| MLLT3 | myeloid/lymphoid or mixed-lineage leukemia (trithorax homolog, *Drosophila*); translocated to, 3 (AF9) | 9 | 9p22 | ALL |
| MLLT4 | myeloid/lymphoid or mixed-lineage leukemia (trithorax homolog, *Drosophila*); translocated to, 4 (AF6) | 6 | 6q27 | AL |

TABLE 1-continued

| | Examples of cancer genes | | | |
|---|---|---|---|---|
| Gene | Description | Chr | Chr Band | Tumor Types |
| MLLT6 | myeloid/lymphoid or mixed-lineage leukemia (trithorax homolog, *Drosophila*); translocated to, 6(AF17) | 17 | 17q21 | AL |
| MLLT7 | myeloid/lymphoid or mixed-lineage leukemia (trithorax homolog, *Drosophila*); translocated to, 7 (AFX1) | X | Xq13.1 | AL |
| MN1 | meningioma (disrupted in balanced translocation) 1 | 22 | 22ql3 | AML, meningioma |
| MPL | myeloproliferative leukemia virus oncogene, thrombopoietin receptor | 1 | p34 | MPD |
| MSF | MLL septin-like fusion | 17 | 17q25 | AML* |
| MSH2 | mutS homolog 2 (*E. coli*) | 2 | 2p22-p21 | colorectal, endometrial, ovarian |
| MSH6 | mutS homolog 6 (*E. coli*) | 2 | 2p16 | colorectal |
| MSI2 | musashi homolog 2 (*Drosophila*) | 17 | 17q23.2 | CML |
| MSN | moesin | X | Xq11.2-q12 | ALCL |
| MTCP1 | mature T-cell proliferation 1 | X | Xq28 | T cell prolymphocytic leukaemia |
| MUC1 | mucin 1, transmembrane | 1 | 1q21 | B-NHL |
| MUTYH | mutY homolog (*E. coli*) | 1 | 1p34.3-1p32.1 | |
| MYB | v-myb myeloblastosis viral oncogene homolog | 6 | 6q22-23 | adenoid cystic carcinoma |
| MYC | v-myc myelocytomatosis viral oncogene homolog (avian) | 8 | 8q24.12-q24.13 | Burkitt lymphoma, amplified in other cancers, B-CLL |
| MYCL1 | v-myc myelocytomatosis viral oncogene homolog 1, lung carcinoma derived (avian) | 1 | 1p34.3 | small cell lung carcinoma |
| MYCN | v-myc myelocytomatosis viral related oncogene, neuroblastoma derived (avian) | 2 | 2p24.1 | neuroblastoma |
| MYD88 | myeloid differentiation primary response gene (88) | 3 | 3p22 | ABC-DLBCL |
| MYH11 | myosin, heavy polypeptide 11, smooth muscle | 16 | 16p13.13-p13.12 | AML |
| MYH9 | myosin, heavy polypeptide 9, non-muscle | 22 | 22q13.1 | ALCL |
| MYST4 | MYST histone acetyltransferase (monocytic leukemia) 4 (MORF) | 10 | 10q22 | AML |
| NACA | nascent-polypeptide-associated complex alpha polypeptide | 12 | 12q23-q24.1 | NHL |
| NBS1 | Nijmegen breakage syndrome 1 (nibrin) | 8 | 8q21 | |
| NCOA1 | nuclear receptor coactivator 1 | 2 | 2p23 | alveolar rhabdomyosarcoma |
| NCOA2 | nuclear receptor coactivator 2 (TIF2) | 8 | 8q13.1 | AML, chondrosarcoma |
| NCOA4 | nuclear receptor coactivator 4 - PTC3 (ELE1) | 10 | 10q11.2 | papillary thyroid |
| NDRG1 | N-myc downstream regulated 1 | 8 | 8q24.3 | prostate |
| NF1 | neurofibromatosis type 1 gene | 17 | 17q12 | neurofibroma, glioma |
| NF2 | neurofibromatosis type 2 gene | 22 | 22q12.2 | meningioma, acoustic neuroma, renal |
| NFE2L2 | nuclear factor (erythroid-derived 2)-like 2 (NRF2) | 2 | 2q31 | NSCLC, HNSCC |
| NFIB | nuclear factor I/B | 9 | 9p24.1 | adenoid cystic carcinoma, lipoma |
| NFKB2 | nuclear factor of kappa light polypeptide gene enhancer in B-cells 2 (p49/p100) | 10 | 10q24 | B-NHL |
| NIN | ninein (GSK3B interacting protein) | 14 | 14q24 | MPD |
| NKX2-1 | NK2 homeobox 1 | 14 | 14q13 | NSCLC |

TABLE 1-continued

| Gene | Description | Chr | Chr Band | Tumor Types |
|---|---|---|---|---|
| | Examples of cancer genes | | | |
| NONO | non-POU domain containing, octamer-binding | X | Xq13.1 | papillary renal |
| NOTCH1 | Notch homolog 1, translocation-associated (*Drosophila*) (TAN1) | 9 | 9q34.3 | T-ALL |
| NOTCH2 | Notch homolog 2 | 1 | 1p13-p11 | marginal zone lymphoma, DLBCL |
| NPM1 | nucleophosmin (nucleolar phosphoprotein B23, numatrin) | 5 | 5q35 | NHL, APL, AML |
| NR4A3 | nuclear receptor subfamily 4, group A, member 3 (NOR1) | 9 | 9q22 | extraskeletal myxoid chondrosarcoma |
| NRAS | neuroblastoma RAS viral (v-ras) oncogene homolog | 1 | 1p13.2 | melanoma, MM, AML, thyroid |
| NSD1 | nuclear receptor binding SET domain protein 1 | 5 | 5q35 | AML |
| NT5C2 | 5'-nucleotidase, cytosolic II | 10 | 10q24.32 | relapse ALL |
| NTRK1 | neurotrophic tyrosine kinase, receptor, type 1 | 1 | 1q21-q22 | papillary thyroid |
| NTRK3 | neurotrophic tyrosine kinase, receptor, type 3 | 15 | 15q25 | congenital fibrosarcoma, secretory breast |
| NUMA1 | nuclear mitotic apparatus protein 1 | 11 | 11q13 | APL |
| NUP214 | nucleoporin 214 kDa (CAN) | 9 | 9q34.1 | AML, T-ALL |
| NUP98 | nucleoporin 98 kDa | 11 | 11p15 | AML |
| OLIG2 | oligodendrocyte lineage transcription factor 2 (BHLHB1) | 21 | 21q22.11 | T-ALL |
| OMD | osteomodulin | 9 | 9q22.31 | aneurysmal bone cyst |
| P2RY8 | purinergic receptor P2Y, G-protein coupled, 8 | X, Y | Xp22.3; Yp11.3 | B-ALL, Down syndrome associated ALL |
| PAFAH1B2 | platelet-activating factor acetylhydrolase, isoform Ib, beta subunit 30 kDa | 11 | 11q23 | MLCLS |
| PALB2 | partner and localizer of BRCA2 | 16 | 16p12.1 | |
| PAX3 | paired box gene 3 | 2 | 2q35 | alveolar rhabdomyosarcoma |
| PAX5 | paired box gene 5 (B-cell lineage specific activator protein) | 9 | 9p13 | NHL, ALL, B-ALL |
| PAX7 | paired box gene 7 | 1 | 1p36.2-p36.12 | alveolar rhabdomyosarcoma |
| PAX8 | paired box gene 8 | 2 | 2q12-q14 | follicular thyroid |
| PBRM1 | polybromo 1 | 3 | 3p21 | clear cell renal carcinoma, breast |
| PBX1 | pre-B-cell leukemia transcription factor 1 | 1 | 1q23 | pre B-ALL, myoepithelioma |
| PCM1 | pericentriolar material 1 (PTC4) | 8 | 8p22-p21.3 | papillary thyroid, CML, MPD |
| PCSK7 | proprotein convertase subtilisin/kexin type 7 | 11 | 11q23.3 | MLCLS |
| PDE4DIP | phosphodiesterase 4D interacting protein (myomegalin) | 1 | 1q12 | MPD |
| PDGFB | platelet-derived growth factor beta polypeptide (simian sarcoma viral (v-sis) oncogene homolog) | 22 | 22q12.3-q13.1 | DFSP |
| PDGFRA | platelet-derived growth factor, alpha-receptor | 4 | 4q11-q13 | GIST, idiopathic hypereosinophilic syndrome, paediatric glioblastoma |
| PDGFRB | platelet-derived growth factor receptor, beta polypeptide | 5 | 5q31-q32 | MPD, AML, CMML, CML |
| PER1 | period homolog 1 (*Drosophila*) | 17 | 17p13.1-17p12 | AML, CMML |
| PHF6 | PHD finger protein 6 | X | Xq26.3 | ETP ALL |
| PHOX2B | paired-like homeobox 2b | 4 | 4p12 | neuroblastoma |
| PICALM | phosphatidylinositol binding clathrin assembly protein (CALM) | 11 | 11q14 | TALL, AML, |
| PIK3CA | phosphoinositide-3 -kinase, catalytic, alpha polypeptide | 3 | 3q26.3 | colorectal, gastric, glioblastoma, breast |

TABLE 1-continued

| | Examples of cancer genes | | | |
|---|---|---|---|---|
| Gene | Description | Chr | Chr Band | Tumor Types |
| PIK3R1 | phosphoinositide-3 -kinase, regulatory subunit 1 (alpha) | 5 | 5q13.1 | glioblastoma, ovarian, colorectal |
| PIM1 | pim-1 oncogene | 6 | 6p21.2 | NHL |
| PLAG1 | pleiomorphic adenoma gene 1 | 8 | 8q12 | salivary adenoma |
| PML | promyelocytic leukemia | 15 | 15q22 | APL, ALL |
| PMS1 | PMS1 postmeiotic segregation increased 1 (*S. cerevisiae*) | 2 | 2q31-q33 | |
| PMS2 | PMS2 postmeiotic segregation increased 2 (*S. cerevisiae*) | 7 | 7p22 | |
| PMX1 | paired mesoderm homeo box 1 | 1 | 1q24 | AML |
| PNUTL1 | peanut-like 1 (*Drosophila*) | 22 | 22q11.2 | AML |
| POT1 | protection of telomeres 1 | 7 | 7q31.33 | CLL |
| POU2AF1 | POU domain, class 2, associating factor 1 (OBF1) | 11 | 11q23.1 | NHL |
| POU5F1 | POU domain, class 5, transcription factor 1 | 6 | 6p21.31 | sarcoma |
| PPARG | peroxisome proliferative activated receptor, gamma | 3 | 3p25 | follicular thyroid |
| PPP2R1A | protein phosphatase 2, regulatory subunit A, alpha | 19 | 19q13.41 | clear cell ovarian carcinoma |
| PRCC | papillary renal cell carcinoma (translocation-associated) | 1 | 1q21.1 | papillary renal |
| PRDM1 | PR domain containing 1, with ZNF domain | 6 | 6q21 | DLBCL |
| PRDM16 | PR domain containing 16 | 1 | 1p36.23-p33 | MDS, AML |
| PRF1 | perforin 1 (pore forming protein) | 10 | 10q22 | |
| PRKAR1A | protein kinase, cAMP-dependent, regulatory, type I, alpha (tissue specific extinguisher 1) | 17 | 17q23-q24 | papillary thyroid |
| PRO1073 | PRO1073 protein (ALPHA) | 11 | 11q31.1 | renal cell carcinoma (childhood epithelioid) |
| PSIP2 | PC4 and SFRS1 interacting protein 2 (LEDGF) | 9 | 9p22.2 | AML |
| PTCH | Homolog of *Drosophila* Patched gene | 9 | 9q22.3 | skin basal cell, medulloblastoma |
| PTEN | phosphatase and tensin homolog gene | 10 | 10q23.3 | glioma, prostate, endometrial |
| PTPN11 | protein tyrosine phosphatase, non-receptor type 11 | 12 | 12q24.1 | JMML, AML, MDS |
| RAB5EP | rabaptin, RAB GTPase binding effector protein 1 (RABPT5) | 17 | 17p13 | CMML |
| RAC1 | ras-related C3 botulinum toxin substrate 1 (rho family, small GTP binding protein Rac1) | 7 | 7p22 | melanoma |
| RAD51L1 | RAD51-like 1 (*S. cerevisiae*) (RAD51B) | 14 | 14q23-q24.2 | lipoma, uterine leiomyoma |
| RAF1 | v-raf-1 murine leukemia viral oncogene homolog 1 | 3 | 3p25 | pilocytic astrocytoma |
| RALGDS | ral guanine nucleotide dissociation stimulator | 9 | 9q34.3 | PMBL, Hodgkin lymphoma, |
| RANBP17 | RAN binding protein 17 | 5 | 5q34 | ALL |
| RAP1GDS1 | RAP1, GTP-GDP dissociation stimulator 1 | 4 | 4q21-q25 | T-ALL |
| RARA | retinoic acid receptor, alpha | 17 | 17q12 | APL |
| RB1 | retinoblastoma gene | 13 | 13q14 | retinoblastoma, sarcoma, breast, small cell lung carcinoma |
| RBM15 | RNA binding motif protein 15 | 1 | 1p13 | acute megakaryocytic leukaemia |
| RECQL4 | RecQ protein-like 4 | 8 | 8q24.3 | |
| REL | v-rel reticuloendotheliosis viral oncogene homolog (avian) | 2 | 2p13-p12 | Hodgkin lymphoma |

TABLE 1-continued

| | Examples of cancer genes | | | |
|---|---|---|---|---|
| Gene | Description | Chr | Chr Band | Tumor Types |
| RET | ret proto-oncogene | 10 | 10q11.2 | medullary thyroid, papillary thyroid, pheochromocytoma, NSCLC |
| RNF43 | Ring finger protein 43 | 17 | 17q22 | cholangiocarcinoma, ovary, pancreas |
| ROS1 | v-ros UR2 sarcoma virus oncogene homolog 1 (avian) | 6 | 6q22 | glioblastoma, NSCLC |
| RPL10 | ribosomal protein L10 | X | Xq28 | T-ALL |
| RPL22 | ribosomal protein L22 (EAP) | 1 | 1p36.31 | AML, CML |
| RPL5 | ribososomal protein L5 | 1 | 1p22.1 | T-ALL |
| RPN1 | ribophorin I | 3 | 3q21.3-q25.2 | AML |
| RUNDC2A | RUN domain containing 2A | 16 | 16p13.13 | PMBL, Hodgkin lymphoma |
| RUNX1 | runt-related transcription factor 1 (AML1) | 21 | 21q22.3 | AML, preB- ALL, T-ALL |
| RUNXBP2 | runt-related transcription factor binding protein 2 (MOZ/ZNF220) | 8 | 8p11 | AML |
| SBDS | Shwachman-Bodian-Diamond syndrome protein | 7 | 7q11 | |
| SDC4 | syndecan 4 | 20 | 20q12 | NSCLC |
| SDH5 | chromosome 11 open reading frame 79 | 11 | 11q12.2 | |
| SDHB | succinate dehydrogenase complex, subunit B, iron sulfur (Ip) | 1 | 1p36.1-p35 | |
| SDHC | succinate dehydrogenase complex, subunit C, integral membrane protein, 15 kDa | 1 | 1q21 | |
| SDHD | succinate dehydrogenase complex, subunit D, integral membrane protein | 11 | 11q23 | |
| SEPT6 | septin 6 | X | Xq24 | AML |
| SET | SET translocation | 9 | 9q34 | AML |
| SETBP1 | SET binding protein 1 | 18 | 18q21.1 | atypical CML |
| SETD2 | SET domain containing 2 | 3 | 3p21.31 | clear cell renal carcinoma |
| SF3B1 | splicing factor 3b, subunit 1, 155 kDa | 2 | 2q33.1 | myelodysplastic syndrome |
| SFPQ | splicing factor proline/glutamine rich(polypyrimidine tract binding protein associated) | 1 | 1p34.3 | papillary renal |
| SFRS3 | splicing factor, arginine/serine-rich 3 | 6 | 6p21 | follicular lymphoma |
| SH2B3 | SH2B adaptor protein 3 | 12 | 12q24.12 | MPD, sAML, erythrocytosis, B-ALL |
| SH3GL1 | SH3-domain GRB2-like 1 (EEN) | 19 | 19p13.3 | AL |
| SIL | TAL1 (SCL) interrupting locus | 1 | 1p32 | T-ALL |
| SLC34A2 | solute carrier family 34 (sodium phosphate), member 2 | 4 | 4p15.2 | NSCLC |
| SLC45A3 | solute carrier family 45, member 3 | 1 | 1q32 | prostate |
| SMARCA4 | SWI/SNF related, matrix associated, actin dependent regulator of chromatin, subfamily a, member 4 | 19 | 19p13.2 | NSCLC |
| SMARCB1 | SWI/SNF related, matrix associated, actin dependent regulator of chromatin, subfamily b, member 1 | 22 | 22q11 | malignant rhabdoid |
| SMARCE1 | SWI/SNF related, matrix associated, actin dependent regulator of chromatin, subfamily e, member 1 | 17 | 17q21.2 | |
| SMO | smoothened homolog (Drosophila) | 7 | 7q31-q32 | skin basal cell |
| SOCS1 | suppressor of cytokine signaling 1 | 16 | 16p13.13 | Hodgkin lymphoma, PMBL |
| SOX2 | SRY (sex determining region Y)-box 2 | 3 | 3q26.3-q27 | NSCLC, oesophageal squamous carcinoma |

TABLE 1-continued

Examples of cancer genes

| Gene | Description | Chr | Chr Band | Tumor Types |
|------|-------------|-----|----------|-------------|
| SRGAP3 | SLIT-ROBO Rho GTPase activating protein 3 | 3 | 3p25.3 | pilocytic astrocytoma |
| SRSF2 | serine/arginine-rich splicing factor 2 | 17 | 17q25 | MDS, CLL |
| SS18 | synovial sarcoma translocation, chromosome 18 | 18 | 18q11.2 | synovial sarcoma |
| SS18L1 | synovial sarcoma translocation gene on chromosome 18-like 1 | 20 | 20q13.3 | synovial sarcoma |
| SSH3BP1 | spectrin SH3 domain binding protein 1 | 10 | 10p11.2 | AML |
| SSX1 | synovial sarcoma, X breakpoint 1 | X | Xp11.23-p11.22 | synovial sarcoma |
| SSX2 | synovial sarcoma, X breakpoint 2 | X | Xp11.23-p11.22 | synovial sarcoma |
| SSX4 | synovial sarcoma, X breakpoint 4 | X | Xp11.23 | synovial sarcoma |
| STAT3 | signal transducer and activator of transcription 3 (acute-phase response factor) | 17 | 17q21.31 | T-cell large granular lymphocytic lymphoma |
| STK11 | serine/threonine kinase 11 gene (LKB1) | 19 | 19p13.3 | NSCLC, pancreatic |
| STL | Six-twelve leukemia gene | 6 | 6q23 | B-ALL |
| SUFU | suppressor of fused homolog (Drosophila) | 10 | 10q24.32 | medulloblastoma |
| SUZ12 | suppressor of zeste 12 homolog (Drosophila) | 17 | 17q11.2 | endometrial stromal tumour |
| SYK | spleen tyrosine kinase | 9 | 9q22 | MDS, peripheral T-cell lymphoma |
| TAF15 | TAF15 RNA polymerase II, TATA box binding protein (TBP)-associated factor, 68 kDa | 17 | 17q11.1-q11.2 | extraskeletal myxoid chondrosarcoma, ALL |
| TAL1 | T-cell acute lymphocytic leukemia 1 (SCL) | 1 | 1p32 | lymphoblastic leukaemia/biphasic |
| TAL2 | T-cell acute lymphocytic leukemia 2 | 9 | 9q31 | T-ALL |
| TCEA1 | transcription elongation factor A (SII), 1 | 8 | 8q11.2 | salivary adenoma |
| TCF1 | transcription factor 1, hepatic (HNF1) | 12 | 12q24.2 | hepatic adenoma, hepatocellular |
| TCF12 | transcription factor 12 (HTF4, helix-loop-helix transcription factors 4) | 15 | 15q21 | Extraskel etal ,myxoi d chondrosarcoma |
| TCF3 | transcription factor 3 (E2A immunoglobulin enhancer binding factors E12/E47) | 19 | 19p13.3 | pre B-ALL |
| TCF7L2 | transcription factor 7-like 2 | 10 | 10q25.3 | colorectal |
| TCL1A | T-cell leukemia/lymphoma 1A | 14 | 14q32.1 | T-CLL |
| TCL6 | T-cell leukemia/lymphoma 6 | 14 | 14q32.1 | T-ALL |
| TERT | telomerase reverse transcriptase | 5 | 5p15.33 | melanoma |
| TET2 | tet oncogene family member 2 | 4 | 4q24 | MDS |
| TFE3 | transcription factor binding to IGHM enhancer 3 | X | Xp11.22 | papillary renal, alveolar soft part sarcoma, renal |
| TFEB | transcription factor EB | 6 | 6p21 | renal cell carcinoma (childhood epithelioid) |
| TFG | TRK-fused gene | 3 | 3q11-q12 | papillary thyroid, ALCL, NSCLC |
| TFPT | TCF3 (E2A) fusion partner (in childhood leukaemia) | 19 | 19q13 | pre-B ALL |
| TFRC | transferrin receptor (p90, CD71) | 3 | 3q29 | NHL |
| THRAP3 | thyroid hormone receptor associated protein 3 (TRAP150) | 1 | 1p34.3 | aneurysmal bone cyst |
| TIF1 | transcriptional intermediary factor 1 (PTC6, TIF1A) | 7 | 7q32-q34 | APL |
| TLX1 | T-cell leukemia, homeobox 1 (HOX11) | 10 | 10q24 | T-ALL |

TABLE 1-continued

Examples of cancer genes

| Gene | Description | Chr | Chr Band | Tumor Types |
|------|-------------|-----|----------|-------------|
| TLX3 | T-cell leukemia, homeobox 3 (HOX11L2) | 5 | 5q35.1 | T-ALL |
| TMPRSS2 | transmembrane protease, serine 2 | 21 | 21q22.3 | prostate |
| TNFAIP3 | tumor necrosis factor, alpha-induced protein 3 | 6 | 6q23 | marginal zone B-cell lymphomas, Hodgkin lymphoma, PMBL |
| TNFRSF14 | tumor necrosis factor receptor superfamily, member 14 (herpesvirus entry mediator) | 1 | 1p36.32 | follicular lymphoma |
| TNFRSF17 | tumor necrosis factor receptor superfamily, member 17 | 16 | 16p13.1 | intestinal T-cell lymphoma |
| TNFRSF6 | tumor necrosis factor receptor superfamily, member 6 (FAS) | 10 | 10q24.1 | TGCT, nasal NK/T lymphoma, skin squamous cell carcinoma-burn scar related |
| TOP1 | topoisomerase (DNA) I | 20 | 20q12-q13.1 | AML* |
| TP53 | tumor protein p53 | 17 | 17p13 | breast, colorectal, lung, sarcoma, adrenocortical, glioma, multiple other tumour types |
| TPM3 | tropomyosin 3 | 1 | 1q22-q23 | papillary thyroid, ALCL, NSCLC |
| TPM4 | tropomyosin 4 | 19 | 19p13.1 | ALCL |
| TPR | translocated promoter region | 1 | 1q25 | papillary thyroid |
| TRA@ | T cell receptor alpha locus | 14 | 14q11.2 | T-ALL |
| TRAF7 | tumour necrosis factor receptor-associated factor 7 | 16 | 16p13.3 | meningioma |
| TRB@ | T cell receptor beta locus | 7 | 7q35 | T-ALL |
| TRD@ | T cell receptor delta locus | 14 | 14q11 | T-cell leukaemia |
| TRIM27 | tripartite motif-containing 27 | 6 | 6p22 | papillary thyroid |
| TRIM33 | tripartite motif-containing 33 (PTC7, TIF1G) | 1 | 1p13 | papillary thyroid |
| TRIP11 | thyroid hormone receptor interactor 11 | 14 | 14q31-q32 | AML |
| TSC1 | tuberous sclerosis 1 gene | 9 | 9q34 | renal cell carcinoma, bladder carcinoma |
| TSC2 | tuberous sclerosis 2 gene | 16 | 16p13.3 | pulmonary lymphangioleiomyomatosis (LAM), renal angiomyolipoma and head and neck cancer |
| TSHR | thyroid stimulating hormone receptor | 14 | 14q31 | toxic thyroid adenoma |
| TTL | tubulin tyrosine ligase | 2 | 2q13 | acute lymphocytic leukaemia |
| U2AF1 | U2 small nuclear RNA auxiliary factor 1 | 21 | 21q22.3 | chronic lymphatic leukaemia, myelodysplastic syndrome |
| USP6 | ubiquitin specific peptidase 6 (Tre-2 oncogene) | 17 | 17p13 | aneurysmal bone cyst |
| VHL | von Hippel-Lindau syndrome gene | 3 | 3p25 | renal, haemangioma, pheochromocytoma |
| VTI1A | vesicle transport through interaction with t-SNAREs homolog 1A | 10 | 10q25.2 | colorectal |
| WAS | Wiskott-Aldrich syndrome | X | Xp11.23-p11.22 | |
| WHSC1 | Wolf-Hirschhorn syndrome candidate 1(MMSET) | 4 | 4p16.3 | Multiple myeloma |
| WHSC1L1 | Wolf-Hirschhorn syndrome candidate 1-like 1 (NSD3) | 8 | 8p12 | AML |
| WIF1 | WNT inhibitory factor 1 | 12 | 12q14.3 | pleomorphic salivary gland adenoma |
| WRN | Werner syndrome (RECQL2) | 8 | 8p12-p11.2 | |
| WT1 | Wilms tumour 1 gene | 11 | 11p13 | Wilms tumour, desmoplastic small round cell tumour |
| WTX | family with sequence similarity 123B (FAM123B) | X | Xq11.1 | Wilms tumour |
| WWTR1 | WW domain containing transcription regulator 1 | 3 | 3q23-q24 | epithelioid haemangioendothelioma |

TABLE 1-continued

| | Examples of cancer genes | | | |
|---|---|---|---|---|
| Gene | Description | Chr | Chr Band | Tumor Types |
| XPA | xeroderma pigmentosum, complementation group A | 9 | 9q22.3 | |
| XPC | xeroderma pigmentosum, complementation group C | 3 | 3p25 | |
| XPO1 | exportin 1 (CRM1 homolog, yeast) | 2 | 2p15 | CLL |
| YWHAE | tyrosine 3-monooxygenase/tryptophan 5-monooxygenase activation protein, epsilon polypeptide (14-3-3 epsilon) | 17 | 17p13.3 | edometrial stromal sarcoma |
| ZNF145 | zinc finger protein 145 (PLZF) | 11 | 11q23.1 | APL |
| ZNF198 | zinc finger protein 198 | 13 | 13q11-q12 | MPD, NHL |
| ZNF278 | zinc finger protein 278 (ZSG) | 22 | 22q12-q14 | Ewing sarcoma |
| ZNF331 | zinc finger protein 331 | 19 | 19q13.3-q13.4 | follicular thyroid adenoma |
| ZNF384 | zinc finger protein 384 (CIZ/NMP4) | 12 | 12p13 | ALL |
| ZNF521 | zinc finger protein 521 | 18 | 18q11.2 | ALL |
| ZNF9 | zinc finger protein 9 (a cellular retroviral nucleic acid binding protein) | 3 | 3q21 | aneurysmal bone cyst |
| ZRSR2 | zinc finger (CCCH type), RNA-binding motif and serine/arginine rich 2 | X | Xp22.1 | MDS, CLL |

TABLE 2

| | Exemplary microRNAs | | | |
|---|---|---|---|---|
| hsa-miR-197 | hsa-miR-99b | hsa-miR-422a | hsa-miR-663b | hsa-miR-1272 |
| hsa-miR-23b | hsa-miR-30b | hsa-miR-375 | hsa-miR-325 | hsa-miR-20b |
| hsa-miR-1295 | hsa-miR-488* | hsa-miR-222 | hsa-miR-224 | hsa-miR-9 |
| hsa-miR-567 | hsa-miR-588 | hsa-miR-548d-5p | hsa-miR-875-3p | hsa-miR-1183 |
| hsa-miR-1268 | hsa-miR-1279 | hsa-miR-10a* | hsa-miR-181a* | hsa-miR-379* |
| hsa-miR-15b | hsa-miR-132 | hsa-miR-151-5p | hsa-miR-518e | hsa-miR-603 |
| hsa-miR-1246 | hsa-miR-185* | hsa-let-7a-1 | hsa-let-7a-2 | hsa-let-7a-3 |
| hsa-let-7e | hsa-let-7f-1 | hsa-let-7f-2 | hsa-let-7g | hsa-let-7i |
| hsa-mir-101-1 | hsa-mir-101-2 | hsa-mir-103-1 | hsa-mir-103-2 | hsa-mir-105-1 |
| hsa-mir-107 | hsa-mir-10a | hsa-mir-10b | hsa-mir-122 | hsa-mir-1226 |
| hsa-mir-1249 | hsa-mir-125a | hsa-mir-125b-1 | hsa-mir-125b-2 | hsa-mir-126 |
| hsa-mir-129-1 | hsa-mir-129-2 | hsa-mir-1291 | hsa-mir-1295 | hsa-mir-1296 |
| hsa-mir-132 | hsa-mir-133a-1 | hsa-mir-133a-2 | hsa-mir-133b | hsa-mir-134 |
| hsa-miR-107 | hsa-miR-767-3p | hsa-miR-422a | hsa-miR-1263 | hsa-miR-181a |
| hsa-mir-100 | hsa-mir-106b | hsa-mir-124-3 | hsa-mir-128-2 | hsa-mir-130b |
| hsa-let-7f | hsa-miR-662 | hsa-miR-325 | hsa-miR-1207-5p | hsa-miR-519a* |
| hsa-let-7c | hsa-mir-1-2 | hsa-mir-106a | hsa-mir-124-2 | hsa-mir-128-1 |
| hsa-let-7d | hsa-mir-135b | hsa-mir-136 | hsa-mir-137 | hsa-mir-138-1 |
| hsa-mir-139 | hsa-miR-139-5p | hsa-mir-140 | hsa-mir-141 | hsa-mir-142 |
| hsa-mir-144 | hsa-mir-145 | hsa-mir-146a | hsa-mir-146b | hsa-mir-147 |
| hsa-mir-148b | hsa-mir-149 | hsa-mir-150 | hsa-mir-151 | hsa-mir-152 |
| hsa-mir-153-2 | hsa-mir-154 | hsa-mir-155 | hsa-mir-15a | hsa-mir-15b |
| hsa-mir-16-2 | hsa-mir-17 | hsa-mir-181a-1 | hsa-mir-181a-2 | hsa-mir-181b-1 |
| hsa-mir-181c | hsa-mir-181d | hsa-mir-182 | hsa-mir-183 | hsa-mir-184 |
| hsa-mir-186 | hsa-mir-187 | hsa-mir-188 | hsa-mir-18a | hsa-mir-18b |
| hsa-mir-191 | hsa-mir-192 | hsa-mir-193a | hsa-mir-193a | hsa-mir-193b |
| hsa-mir-194-2 | hsa-mir-195 | hsa-mir-196a-1 | hsa-mir-196a-2 | hsa-mir-196b |
| hsa-mir-198 | hsa-mir-199a-1 | hsa-mir-199a-2 | hsa-mir-199b | hsa-mir-19a |
| hsa-mir-19b-2 | hsa-mir-200a | hsa-mir-200b | hsa-mir-200c | hsa-mir-202 |
| hsa-mir-204 | hsa-mir-205 | hsa-mir-206 | hsa-mir-208a | hsa-mir-20a |
| hsa-mir-21 | hsa-mir-210 | hsa-mir-211 | hsa-mir-212 | hsa-mir-214 |
| hsa-mir-216a | hsa-mir-217 | hsa-mir-218-1 | hsa-mir-218-2 | hsa-mir-219-1 |
| hsa-mir-22 | hsa-mir-220a | hsa-mir-221 | hsa-mir-222 | hsa-mir-223 |
| hsa-mir-23a | hsa-mir-23b | hsa-mir-24-1 | hsa-mir-24-2 | hsa-mir-25 |
| hsa-mir-26a-1 | hsa-mir-26a-2 | hsa-mir-26b | hsa-mir-27a | hsa-mir-27b |
| hsa-mir-296 | hsa-mir-299 | hsa-mir-29a | hsa-mir-29b-1 | hsa-mir-29b-2 |
| hsa-mir-301a | hsa-mir-302a | hsa-mir-302b | hsa-mir-302c | hsa-mir-302d |

TABLE 2-continued

| Exemplary microRNAs | | | | |
|---|---|---|---|---|
| hsa-mir-30b | hsa-mir-30c-1 | hsa-mir-30c-2 | hsa-mir-30d | hsa-mir-30e |
| hsa-mir-32 | hsa-miR-32* | hsa-miR-320 | hsa-mir-320a | hsa-mir-323 |
| hsa-mir-325 | hsa-mir-326 | hsa-mir-328 | hsa-mir-329-1 | hsa-mir-329-2 |
| hsa-mir-331 | hsa-mir-335 | hsa-mir-337 | hsa-mir-338 | hsa-mir-339 |
| hsa-mir-33b | hsa-mir-340 | hsa-mir-342 | hsa-mir-345 | hsa-mir-346 |
| hsa-mir-34b | hsa-mir-34c | hsa-mir-361 | hsa-mir-362 | hsa-mir-363 |
| hsa-mir-365-2 | hsa-mir-367 | hsa-mir-369 | hsa-mir-370 | hsa-mir-371 |
| hsa-mir-373 | hsa-mir-374a | hsa-mir-374b | hsa-mir-375 | hsa-mir-376a-1 |
| hsa-mir-376c | hsa-mir-377 | hsa-mir-378 | hsa-mir-379 | hsa-mir-380 |
| hsa-mir-382 | hsa-mir-383 | hsa-mir-384 | hsa-mir-409 | hsa-mir-410 |
| hsa-mir-421 | hsa-mir-422a | hsa-mir-423 | hsa-mir-424 | hsa-mir-425 |
| hsa-mir-431 | hsa-mir-432 | hsa-mir-433 | hsa-mir-449a | hsa-mir-449b |
| hsa-mir-451 | hsa-mir-452 | hsa-mir-453 | hsa-mir-454 | hsa-mir-455 |
| hsa-mir-484 | hsa-mir-485 | hsa-mir-486 | hsa-mir-487a | hsa-mir-487b |
| hsa-mir-489 | hsa-mir-490 | hsa-mir-491 | hsa-mir-492 | hsa-mir-493 |
| hsa-mir-495 | hsa-mir-496 | hsa-mir-497 | hsa-mir-498 | hsa-mir-499 |
| hsa-mir-501 | hsa-mir-502 | hsa-mir-503 | hsa-mir-505 | hsa-mir-508 |
| hsa-mir-509-3 | hsa-mir-510 | hsa-mir-511-1 | hsa-mir-511-2 | hsa-mir-512-1 |
| hsa-mir-513a-1 | hsa-mir-513a-2 | hsa-mir-515-1 | hsa-mir-515-2 | hsa-mir-516a-1 |
| hsa-mir-516b-1 | hsa-mir-516b-2 | hsa-mir-517a | hsa-mir-517b | hsa-mir-517c |
| hsa-mir-518a-2 | hsa-mir-518b | hsa-mir-518c | hsa-mir-518d | hsa-mir-518e |
| hsa-mir-519a-1 | hsa-mir-519a-2 | hsa-mir-519b | hsa-mir-519c | hsa-mir-519d |
| hsa-mir-520a | hsa-mir-520b | hsa-mir-520c | hsa-mir-520d | hsa-mir-520e |
| hsa-mir-520g | hsa-mir-520h | hsa-mir-521-1 | hsa-mir-521-2 | hsa-mir-522 |
| hsa-mir-524 | hsa-mir-525 | hsa-mir-526a-1 | hsa-mir-526a-2 | hsa-mir-526b |
| hsa-mir-532 | hsa-mir-539 | hsa-mir-542 | hsa-mir-543 | hsa-mir-548o |
| hsa-mir-550-1 | hsa-mir-551a | hsa-mir-561 | hsa-mir-566 | hsa-mir-567 |
| hsa-mir-572 | hsa-mir-574 | hsa-mir-575 | hsa-mir-576 | hsa-mir-582 |
| hsa-mir-589 | hsa-mir-590 | hsa-mir-593 | hsa-mir-598 | hsa-mir-601 |
| hsa-mir-605 | hsa-mir-608 | hsa-mir-611 | hsa-mir-621 | hsa-mir-622 |
| hsa-mir-627 | hsa-mir-629 | hsa-mir-632 | hsa-mir-634 | hsa-mir-635 |
| hsa-mir-639 | hsa-mir-642 | hsa-mir-644 | hsa-mir-646 | hsa-mir-648 |
| hsa-mir-650 | hsa-mir-652 | hsa-mir-657 | hsa-mir-658 | hsa-mir-659 |
| hsa-mir-661 | hsa-mir-662 | hsa-mir-663 | hsa-mir-663b | hsa-mir-671 |
| hsa-mir-7-1 | hsa-mir-7-2 | hsa-mir-7-3 | hsa-mir-708 | hsa-mir-744 |
| hsa-mir-767 | hsa-miR-768-3p | hsa-mir-874 | hsa-mir-886 | hsa-mir-888 |
| hsa-miR-9 | hsa-mir-9-1 | hsa-mir-9-2 | hsa-mir-9-3 | hsa-mir-923 |
| hsa-mir-92a-2 | hsa-mir-92b | hsa-mir-93 | hsa-mir-95 | hsa-mir-96 |
| hsa-mir-99a | hsa-mir-99b | hsa-miR-99b* | mmu-mir-1-1 | mmu-mir-100 |
| mmu-mir-103-2 | mmu-mir-106a | mmu-mir-106b | mmu-mir-10a | mmu-mir-10b |
| mmu-mir-125b-1 | mmu-mir-126 | mmu-mir-130b | mmu-mir-133a-1 | mmu-mir-133b |
| mmu-mir-139 | mmu-mir-140 | mmu-mir-143 | mmu-mir-145 | mmu-mir-150 |
| mmu-mir-15a | mmu-mir-16-1 | mmu-mir-17 | mmu-mir-181a-1 | mmu-mir-181c |
| mmu-mir-184 | mmu-mir-18a | mmu-mir-192 | mmu-mir-193b | mmu-mir-196b |
| mmu-mir-19b-1 | mmu-mir-19b-2 | mmu-mir-203 | mmu-mir-207 | mmu-mir-20a |
| mmu-mir-210 | mmu-mir-22 | mmu-mir-222 | mmu-mir-223 | mmu-mir-23a |
| mmu-mir-25 | mmu-mir-27a | mmu-mir-27b | mmu-mir-290 | mmu-mir-292 |
| mmu-mir-298 | mmu-mir-29a | mmu-mir-29c | mmu-mir-301a | mmu-mir-30b |
| mmu-mir-31 | mmu-mir-322 | mmu-mir-33 | mmu-mir-346 | mmu-mir-351 |
| mmu-mir-365-1 | mmu-mir-375 | mmu-mir-378 | mmu-mir-450b | mmu-mir-466a |
| mmu-mir-468 | mmu-mir-486 | mmu-mir-500 | mmu-mir-503 | mmu-mir-542 |
| mmu-mir-669a-1 | mmu-mir-669c | mmu-mir-674 | mmu-mir-680-1 | mmu-mir-681 |
| mmu-mir-686 | mmu-mir-691 | mmu-mir-699 | mmu-mir-706 | mmu-mir-710 |
| mmu-mir-712 | mmu-mir-714 | mmu-mir-721 | mmu-mir-7a-1 | mmu-mir-7a-2 |
| mmu-mir-877 | mmu-mir-9-1 | mmu-mir-92a-1 | mmu-mir-93 | mmu-mir-99a |
| hsa-miR-424* | hsa-miR-605 | hsa-miR-34b | hsa-miR-663b | hsa-miR-202* |
| hsa-miR-663 | hsa-let-7b | hsa-mir-1-1 | hsa-mir-105-2 | hsa-mir-124-1 |
| hsa-mir-127 | hsa-mir-1307 | hsa-mir-135a-1 | hsa-miR-1305 | hsa-mir-135a-2 |
| hsa-miR-668 | hsa-mir-130a | hsa-mir-138-2 | hsa-mir-143 | hsa-mir-148a |
| hsa-mir-153-1 | hsa-mir-16-1 | hsa-mir-181b-2 | hsa-mir-185 | hsa-mir-190 |
| hsa-mir-194-1 | hsa-mir-197 | hsa-mir-19b-1 | hsa-mir-203 | hsa-mir-20b |
| hsa-mir-215 | hsa-mir-219-2 | hsa-mir-224 | hsa-miR-26a | hsa-mir-28 |
| hsa-mir-29c | hsa-mir-30a | hsa-mir-31 | hsa-mir-324 | hsa-mir-330 |
| hsa-mir-33a | hsa-mir-34a | hsa-mir-365-1 | hsa-mir-372 | hsa-mir-376b |
| hsa-mir-381 | hsa-mir-412 | hsa-mir-429 | hsa-mir-450a-1 | hsa-mir-483 |
| hsa-mir-488 | hsa-mir-494 | hsa-mir-500 | hsa-mir-509-1 | hsa-mir-512-2 |
| hsa-mir-516a-2 | hsa-mir-518a-1 | hsa-mir-518f | hsa-mir-519e | hsa-mir-520f |
| hsa-mir-523 | hsa-mir-527 | hsa-miR-550 | hsa-mir-571 | hsa-mir-584 |
| hsa-mir-604 | hsa-mir-625 | hsa-mir-637 | hsa-mir-649 | hsa-mir-660 |
| hsa-miR-7 | hsa-mir-766 | hsa-mir-891a | hsa-mir-92a-1 | hsa-mir-98 |
| mmu-mir-103-1 | mmu-mir-125a | mmu-mir-138-2 | mmu-mir-155 | mmu-mir-182 |
| mmu-mir-199b | mmu-mir-20b | mmu-mir-23b | mmu-mir-296 | mmu-mir-30e |
| mmu-mir-363 | mmu-mir-467a | mmu-mir-652 | mmu-mir-685 | mmu-mir-711 |
| mmu-mir-805 | | | | |

Example 8

Methods

Cell Culture

The PC3 cell line was obtained from the American Type Culture Collection (ATCC). The DU145DIAPH3-KD cell line, stably transfected with DIAPH3 shRNA, was generated in our laboratories. PC3 and DU145DIAPH3-KD cell lines were cultured in DMEM (Invitrogen). All cells were supplemented with 10% foetal bovine serum (Denville Scientific), 2 mM L-glutamine (Invitrogen) and 1% PenStrep (Invitrogen). DU145DIAPH3-KD cells were additionally selected with 2 µg/mL puromycin as described. All cells were grown at 37° C. and 5% CO2. Cell viability of the EV-producer cells was tested with the 0.4% Trypan Blue (Sigma) exclusion method. All cell lines were routinely tested for mycoplasma contamination by using the MycoAlert PLUS Mycoplasma Detection Kit (Lonza). Finally, in order to collect EVs from cells in which palmitoylation was inhibited, PC3 cells were treated for 24 hours with 2-bromohexadecanoic acid (Sigma), also known as 2-bromopalmitate (0.5, 1, 5, 10, 20, 50 and 100 µM), in serum-starvation.

Isolation of Extracellular Vesicles (EVs)

The isolation of EVs was conducted as previously described with minor modifications (Vagner et al. Large extracellular vesicles carry most of the tumour DNA circulating in prostate cancer patient plasma. J Extracell Vesicles. 2018; 7(1):1505403; Minciacchi et al. Large oncosomes contain distinct protein cargo and represent a separate functional class of tumor-derived extracellular vesicles. Oncotarget. 2015; 6(13):11327-11341; Minciacchi et al. MYC mediates large oncosome-induced fibroblast reprogramming in prostate cancer. Cancer Res. 2017; 77(9):2306-2317). Cells were grown on 18×150 cm²-cell culture plates (Corning) until 90% confluence, washed in PBS and serum-starved for 24 hours before the collection of conditioned cell media. The conditioned media was cleared by differential centrifugation of floating cells at 300 g, of cell debris at 2,800 g for 10 min, and spun in an ultracentrifuge at 10,000 g for 30 min (4° C., k-factor 2547.2) for the collection of L-EVs. The supernatant was then spun at 100,000 g for 60 min (4° C., k-factor 254.7) for the collection of S-EVs. Both 10,000 g and 100,000 g pellets were then subjected to Optiprep™ (Sigma) density gradient purification. Fresh pelleted EVs were resuspended in 0.2 µm-filtered PBS and deposited at the bottom of an ultracentrifuge tube. Next, 30% (4.3 mL, 1.20 g/mL), 25% (3 mL, 1.15 g/mL), 15% (2.5 mL, 1.10 g/mL), and 5% (6 mL, 1.08 g/mL) iodixanol solutions were sequentially layered at decreasing density to form a discontinuous gradient. Separation was performed by ultracentrifugation at 100,000 g for 3 h 50 min (4° C., k-factor 254.7) and EV-enriched fractions collected either at 1.10-1.15 g/mL for L-EVs or 1.10 g/mL for S-EVs. Purified EVs were then washed in PBS (100,000 g, 60 min, 4° C.) and resuspended in the appropriate buffer. All ultracentrifugation spins were performed in a SW28 swinging rotor (Beckman Coulter).

Whole Cell and Membrane Protein Lysates from EV-Producer Cells

Whole cell lysate (WCL) and membrane preparations (M) were obtained upon 24-hour serum starvation and collection of conditioned cell media. Cell monolayers were scraped and washed in chilled PBS (×3). For WCL, cells were directly lysed in DTT-free 4% SDS/Tris-HCl lysis buffer. For M preparations, cells were gently scraped, washed in PBS (×3) and resuspended in filtered PBS containing 1% protease inhibitors (cOmplete Mini Protease Inhibitor Cocktail, Roche). Cell suspensions were immediately subjected to 20 cycles of sonication (5 sec) in ice to induce cell disruption. Membrane suspensions were then cleared of intact cells at 500 g, pelleted at 16,000 g (20 min, 4° C.), washed in PBS (×3) and resuspended in 4% SDS/Tris-HCl lysis buffer. All protein lysates were stored at −80° C. until use.

LB-ABE Enrichment of Palmitoyl-Proteins

Protein concentration was determined with the Pierce 660 nm protein assay (Pierce). 300 µg of WCL, M and L-EVs (×3); and 250 µg of S-EVs (×2) were subjected to LB-ABE coupled to label-free mass spectrometry as described (Zhou et al. Low-background Acyl-biotinyl exchange largely eliminates the co-isolation of non-S-Acylated proteins and enables deep S-Acylproteomic analysis. Anal Chem. 2019; 91(15):9858-9866). Briefly, proteins were reduced with 50 mM tris(2-carboxyethyl)phosphine (TCEP), sequentially alkylated with 50 mM N-ethylmaleimide (NEM) and 25 mM 2,2'-dithiodipyridine (DTDP), and biotinylated with 1 mM biotin-HPDP in the presence or absence of 2 M neutral hydroxylamine (Hyd). Palmitoyl-proteins were enriched by streptavidin affinity purification, eluted by 50 mM TCEP, and precipitated by methanol/chloroform.

In order to evaluate the specificity of the LB-ABE method, 1 mg of WCL and M protein lysates were subjected to LB-ABE. 2 µg of the recovered palmitoylated fractions were resolved on a SDS-acrylamide gel alongside with 2 µg of the whole protein and non-palmitoylated fractions. Finally, silver staining of the gel was performed with the Silver Stain Kit (Pierce) following manufacturer's recommendations. Alternatively, for the validation of select palmitoyl-proteins in WCL, M, L-EVs and S-EVs, 300 µg of total protein per group were processed as above with minor modifications. Briefly, samples were split into two equal halves in order to constitute the experimental (Hyd+) and negative control (Hyd−) groups prior to LB-ABE chemistry. Experimental groups were subjected to 2 M Hyd treatment as above, whereas control groups were incubated with Tris/HCl buffer in order to evaluate the unspecific recovery of non-palmitoylated proteins. Upon recovery of palmitoylated proteins, experimental and control samples were re-dissolved in loading buffer and 10% (v/v) of total recovered proteins was loaded onto SDS-PAGE gels for immunoblotting analysis.

LC-MS/MS Analysis and Data Processing

Enriched palmitoyl-proteins were digested with MS-grade trypsin (Promega) by filter-aided sample preparation (FASP) as described previously Zhou et al. Low-background Acyl-biotinyl exchange largely eliminates the co-isolation of non-S-Acylated proteins and enables deep S-Acylproteomic analysis. Anal Chem. 2019; 91(15):9858-9866; Wisniewski et al. Universal sample preparation method for proteome analysis. Nat Methods. 2009; 6(5):359-362). Tryptic peptides were then recovered, dried down in a SpeedVac concentrator (Thermo Scientific), and re-dissolved in 0.2% formic acid (Sigma) up to a concentration of 0.15 µg/mL. Label-free proteomic analysis was performed using an EASY-nLC 1000 connected to an LTQ Orbitrap Elite hybrid mass spectrometer essentially as we previously described (Morley et al. Regulation of microtubule dynamics by DIAPH3 influences amoeboid tumor cell mechanics and sensitivity to taxanes. Sci. Rep. 2015; 5(1): 12136; Han et al. FOXC1-induced non-canonical WNT5A-MMP7 signaling regulates invasiveness in triple-negative breast cancer. Oncogene. 2018; 37(10):1399-1408. Briefly, 7 L of peptide solution was loaded onto a 2-cm trap column (75 µm×2 cm, C18) and separated on a 50-cm EASY-Spray analytical column (PepMap RSLC C18, 2 μm, 100 Å, 50 μm×15 cm) heated to 55° C., using a 2 h-gradient consisting of 2-40% B in 150 min, 40-100% B in 20 min, and 100% B in 10 min at the flow rate of 150 nL/min. Separated peptides were ionized with an EASY-Spray ion source. Mass spectra were acquired in a data-dependent manner, with automatic switching between MS and MS/MS scans. In MS scans, the lock mass at m/z 445.120025 was applied to provide real-time internal mass calibration. The full MS scan (400-1600 μm/z) was performed in 240,000 resolution at m/z of 400 Th, with an ion packet setting of $1\times10^6$ for automatic gain control and a maximum injection time of 500 ms. Up to 20 most intense peptide ions with charge state of >2 were automatically selected for MS/MS fragmentation by rapid collision-induced dissociation (rCD), using 7,500 resolution, $1\times10^4$ automatic gain control, 50 ms maximum injection time, 10 ms activation time, and 35% normalized collision energy. To minimize redundant spectral acquisition, dynamic exclusion was enabled with a repeat count of 1, an exclusion during of 30 s, and a repeat duration of 60 s.

The acquired MS data were searched against the Uniprot_Human database (released on Jan. 22, 2016, containing 20,985 protein sequences) using the Andromeda algorithm in theMaxQuant (v1.5.5.1) environment. The searching parameters were set as follows: trypsin/P as the protease; oxidation (M), acetyl (protein N-term), NEM (C) and carbamidomethyl (C) as variable modifications; up to two missed cleavages; minimal peptide length as 7; mass tolerance for MS1 was 4.5 ppm for main search and for MS2 was 0.5 Da; identification of second peptides enabled; label free quantification (LFQ) enabled, and match-between-runs within 2 min were enabled. A stringent false discovery rate (FDR)<0.01 was used to filter PSM, peptide, and protein identifications.

Identification of High-Confidence and High-Abundance Proteins

To retain high-confidence proteins from the raw LFQ data, we applied criteria that proteins should be detected with at least 2 peptides and in at least 2 replicates, and low abundant proteins less than 5% of absolute protein abundance for each identification were discarded for subsequent analyses. Absolute protein abundance for each identification was defined as the median value of replicates. We assumed that the total protein amount and composition of protein species are different between WCL, M, L-EVs and S-EVs. To compare the protein abundance between them, a max-min normalization method was used to scale the protein expression values between 0 to 1. Protein expression value 1 was given to the most abundant protein within each sample and protein value 0 was given to the least abundant protein identified. To determine the cut-off value of the protein expression difference, we computed the protein expression differences of randomly permuted samples, fitted a Gaussian distribution to the random protein expression difference, and then calculated the 99th percentile corresponding to α=0.01 (protein expression difference cut-off=0.1). Finally, in order to detect significantly abundant proteins within each sample, the rank product algorithm was applied to the normalized protein abundance for each identification. In order to identify high-abundance proteins in EVs, WCL or M, we performed integrated hypothesis test. Briefly, Student's t-test and log 2-median ratio test were performed. We estimated empirical null distributions of T values and log 2-median ratio value by randomly permuting all samples 1,000 times and calculating t-test and log 2-median ratio test p values. We then integrated these two p value into an overall p value using Stouffer's method. We then selected proteins with a FDR <0.05 and normalized expression difference ≥0.1.

Functional Annotation of the Palmitoyl-Proteome

The percentage of putative high-confidence (identified by two independent methods in palmitoyl-proteomes or experimentally validated) human palmitoyl-proteins in cells was directly retrieved from the SwissPalm database (v2) (www.swisspalm.org). For EVs, the percentage of putative palmitoyl-proteins was estimated by direct comparison to the number of human proteins retrieved from the ExoCarta database (www.ExoCarta.org). To assess the biological relevance of the putative palmitoyl-proteins in the proteome of prostate cancer EVs, we selected for a subset of proteins uniquely found or differentially expressed (FDR<0.05, Fold change ≥±1.5) in the proteome of L-EVs and S-EVs from a previously published study (Minciacchi et al. Large oncosomes contain distinct protein cargo and represent a separate functional class of tumor-derived extracellular vesicles. Oncotarget. 2015; 6(13):11327-11341). Characterization of the highly and differentially expressed proteins was performed by the Ingenuity Pathway Analysis (IPA, QIAGEN) and DAVID tools. Differentially expressed proteins among groups were selected based on an averaged relative expression difference >0.1 and a p value<0.05 by one-sample t-test. Transcriptional information was recovered from The Cancer Genome Atlas (TCGA, portal.gdc.cancer.gov) databases.

Immunoblotting Analysis

Immunoblotting analysis was performed as described (Zhou et al. Low-background Acyl-biotinyl exchange largely eliminates the co-isolation of non-S-Acylated proteins and enables deep S-Acylproteomic analysis. Anal Chem. 2019; 91(15):9858-9866). Primary antibodies used were HSPA5 (#3177, 1:1,000 dilution), GAPDH (#3683, 1:10,000 dilution), H3.1 (#9717, 1:10,000 dilution) and pan-SRC (#2108, 1:10,000 dilution) from Cell Signaling. Antibodies for TSG101 (sc-7964, 1:1,000 dilution), CD9 (sc-13118, 1:1,000 dilution), STEAP1 (sc-271872, 1:1,000 dilution), and Cav-1 (sc-894, 1:10,000 dilution) were obtained from Santa Cruz. Antibodies to KRT18 (ab93741, 1:10,000 dilution) and CD81 (ab79559, 1:10,000 dilution) were obtained from Abcam and ABCC4 (#GTX15602, 1:10,000 dilution) from GenTex. Antibody to STEAP2 (#PA5-25495, 1:1,000 dilution) was obtained from Thermo Scientific. Densitometric quantification of films was performed with the ImageJ software (v1.52a).

Tunable Resistive Pulse Sensing (TRPS) Measurements

Concentration and particle size distribution of EVs were carried out in a qNano device (iZON Science, New Zealand). Freshly isolated EVs were diluted 1:40 in 0.2-μm filtered PBS and analysed either with a NP2,000-nm nanopore (resolution window 0.9-5.7 μm) for L-EVs or in a NP250-nm nanopore for S-EVs (resolution window 110-630 nm). Membranes were stretched at 47 mm and voltage set either at 0.04 V for L-EVs or 0.5 V for S-EVs in order to achieve a stable current baseline of about 120 nA. Particle size and concentrations were calibrated using Izon calibration particles (1:100 diluted TPK200 for S-EVs, and 1:1,000 diluted CPC2000 for L-EVs) and a minimum of 500 events were registered for each sample with a positive pressure of 5 mbar. Particle quantitation was performed in EVs obtained from ~$3.0\times10^8$ cells and resuspended in 200 μL of filtered PBS.

Flow Cytometry Analysis of Prostate Cancer Cells and L-EVs

L-EVs were isolated as described above. Cells were fixed in 75% EtOH for 30 min at 4° C. L-EVs were fixed in 4% PFA for 10 min at room temperature. Cells and L-EVs were incubated for 30 min or 1 h, respectively, with one of the following primary antibodies: STEAP1 (H00026872-D01P, Abnova) at 1:50 dilution, STEAP2 (PA5-25495, Invitrogen) at 1:10 dilution, or ABCC4 (GTX15602, GeneTex) at 1:20 dilution. Excess antibody was washed off with PBS followed by incubation for 30 min with phycoerythrin-conjugated (111-116-144, Jackson ImmunoResearch; for STEAP1 and STEAP2) or FITC-conjugated (31629, ThermoFisher Scientific; for ABCC4) secondary antibody at 1:250 dilution. Both cell and L-EV samples were analysed using the LSR-II flow cytometer (Becton Dickinson) with settings optimized for the detection of cells or particles larger than 1 μm, respectively. Data were analysed using FlowJo software (Treestar).

Statistical Analysis

Plots represent the mean and standard deviation of at least three independent replicates. Experimental groups were compared using Student's t-test (unpaired, two-tails) and statistical significance established for a p value <0.05.

Example 9

Results

Low-background acyl-biotinyl exchange (LB-ABE) enables highly selective isolation of palmitoyl-proteins from whole cell lysates and membrane preparations Because palmitoyl-proteins are anchored to cellular membranes and EVs are enriched in membrane components, we believed that palmitoyl-proteins would be enriched in EVs. Using an in silico approach, we intersected the compendium of palmitoylated proteins SwissPalm, with the ExoCarta database that contain proteins identified in EVs. As expected, we found a three-fold higher percentage of putative palmitoylated proteins in EVs versus cells (13.2% vs. 4.3%) (data not shown). Further in silico analysis of the whole proteomes of prostate cancer cell-derived L- and S-EVs, obtained by gradient centrifugation, showed that ~20% of the proteins identified in both EV fractions are putative palmitoylated proteins (data not shown). Additionally, when we examined the proteins that are differentially expressed between the two EV fractions, this percentage increased to 43% in L-EVs and 32% in S-EVs (data not shown). These results suggest that palmitoylated proteins are enriched in EVs in comparison to cells and might be differentially distributed in different EV populations.

Quantitative analysis of protein palmitoylation has been impaired by the lack of methodological approaches allowing efficient separation of palmitoylated proteins from non-palmitoylated proteins. We recently developed an improved acyl-biotinyl exchange (ABE) method, termed low-background ABE (LB-ABE), which consists of the blockage of non-palmitoylated cysteine residues by N-ethylmaleimide (NEM) and further by 2,2'-dithiodipyridine (DTDP), followed by converting palmitoylated cysteine residues into biotinylated cysteines and specific purification of palmitoyl-proteins by streptavidin (FIG. 12(a)). This approach largely eliminates the co-isolation of non-palmitoylated proteins, thus enabling a comprehensive and specific palmitoyl-proteomic analysis.

Comprehensive Palmitoyl-Proteomic Analysis Identifies Distinct Protein Signatures for Large and Small Cancer-Derived Extracellular Vesicles We tested the LB-ABE method in membrane preparations (M) from PC3 prostate cancer cells before applying it to EVs because M preparations are easier to generate and give a higher protein yield. Silver staining of M processed through

78

Figure 12:
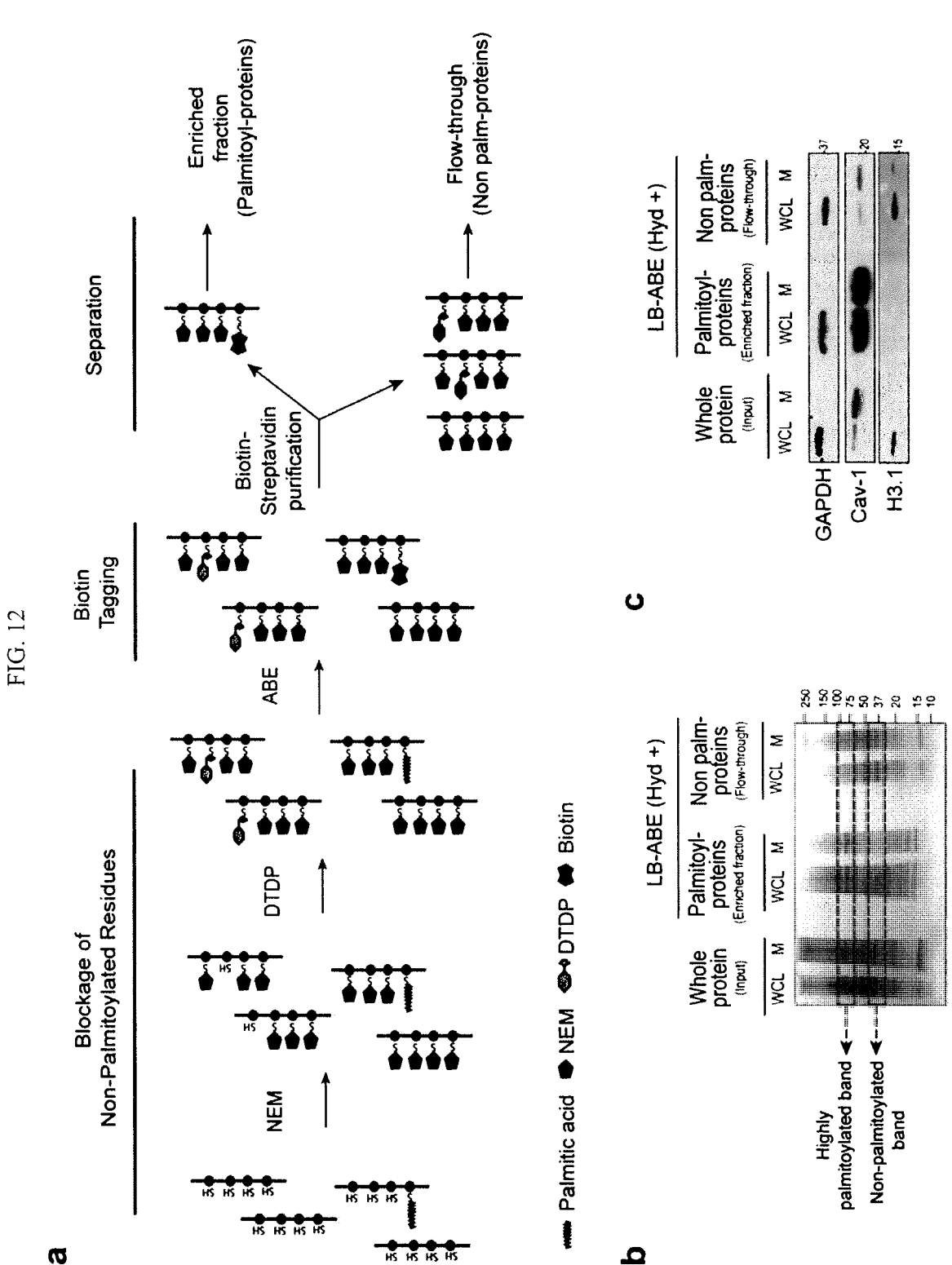
FIG. 12, panels a-c, depicts selective enrichment of putative palmitoylated proteins in the proteome of EVs. (a) Schematic representation of the low-background acyl-biotinyl exchange (LB-ABE) method employed for selective enrichment of palmitoylated proteins. Free cysteines are sequentially blocked by NEM and DTDP incubations. Acyl-biotinyl exchange (ABE) allows specific labelling of palmitoyl-proteins and purification of the whole palmitoyl-proteome by biotin-streptavidin interaction. Non-palmitoylated proteins can be recovered in the flow-through upon specific capture of palmitoyl-proteins with streptavidin-functionalized beads. (b) Silver-stained PAGE gel of PC3 WCL and M protein lysates with versus without LB-ABE enrichment of palmitoyl-proteins. (c) Immunoblotting of the indicated proteins enriched or excluded from the palmitoyl-proteome of WCL and M in PC3 upon LB-ABE.

LB-ABE enrichment showed distinct protein patterns in the fractions enriched with or depleted of palmitoyl-proteins (FIG. 12(b)). This enrichment was further validated by immunoblotting for proteins known to exhibit variable palmitoylation status. Caveolin-1 (Cav-1) was highly enriched in the palmitoyl-protein fraction (lanes 3-4, FIG. 12(c)) and almost completely absent from the palmitoyl-depleted fraction (lanes 5-6, FIG. 12(c)). This remarkable enrichment suggests that Cav-1 is predominantly present as a palmitoylated protein, in agreement with a recent report. In contrast, the nuclear histone H3 (H3.1), which is predicted to be a non-palmitoylated protein, was excluded from the palmitoyl-protein enriched fractions (FIG. 12(c)). GAPDH was detected in similar proportions in its palmitoylated and non-palmitoylated form. The localization of Cav-1 in M, and H3.1 and GAPDH in whole cell lysate (WCL) (lanes 1-2, FIG. 12(c)) confirmed the quality of the subcellular fractionation. The successful enrichment of palmitoylated proteins by LB-ABE in WCL and M encouraged us to apply this approach to studying large scale protein palmitoylation in EVs.

Comprehensive Palmitoyl-Proteomic Analysis Identifies Differentially Abundant Palmitoyl-Proteins in WCL, M, and EVs In order to identify EV-specific palmitoyl-protein signatures, we employed liquid chromatography-tandem mass spectrometry (LC-MS/MS) to analyze candidate palmitoylated proteins isolated by LB-ABE in L-EVs and S-EVs, and performed a comparative analysis with the palmitoyl-proteins identified in WCL and M from PC3 cells. L-EVs and S-EVs were isolated from cell culture media by differential ultracentrifugation followed by density gradient purification (data not shown), in line with the most recent MISEV2018 guidelines and previous studies that separated large oncosomes from exosomes. Over 99% of the cells from which EVs were isolated were viable (data not shown), limiting the possibility of contamination from apoptotic vesicles.

Tunable Resistive Pulse Sensing (TRPS) identified 1.76× $10^9$ particles/mL of 1.5-5 μm diameter, with a modal size of 1.77 μm in L-EV samples (FIG. 13(a)), and 2.43×$10^{11}$ particles/mL of 90-600 nm diameter, with a modal size of 131 nm, in S-EV samples. Despite the higher number of EVs in the S-EV fraction, L-EVs contained significantly more protein than S-EVs derived from the same number of producing cells (FIG. 13(b)). Finally, immunoblotting of proteins enriched in L- and S-EVs confirmed the nature of the EV preparations. L-EVs showed the enrichment of HSPA5 and KRT18 at 1.10-1.15 g/mL, which are enriched in large oncosomes, while S-EVs showed the enrichment of CD81 and TSG101 at 1.10 g/mL, that are typically enriched in exosomes (FIG. 13(c)).

Next we compared the palmitoyl-proteins identified in WCL, M, L-EVs and S-EVs. A total of 2,408 palmitoyl-proteins were identified with a false discovery rate (FDR) of <0.01. We then selected 2,133 high-confidence proteins detected in two or more replicates and no less than 5% of absolute protein abundance. Of these, 1,803 proteins have been reported as palmitoyl-proteins in the SwissPalm database and/or were identified in our recent deep palmitoyl-proteomic profiling of prostate cancer cells (FIG. 13(d)). Of note, we also identified 330 proteins that have not yet been reported as palmitoyl-proteins. Interestingly, 41% of them were identified in EVs. These results confirm the enrichment of palmitoyl-proteins in cell and EV preparations with the LB-ABE approach.

Figure 13:
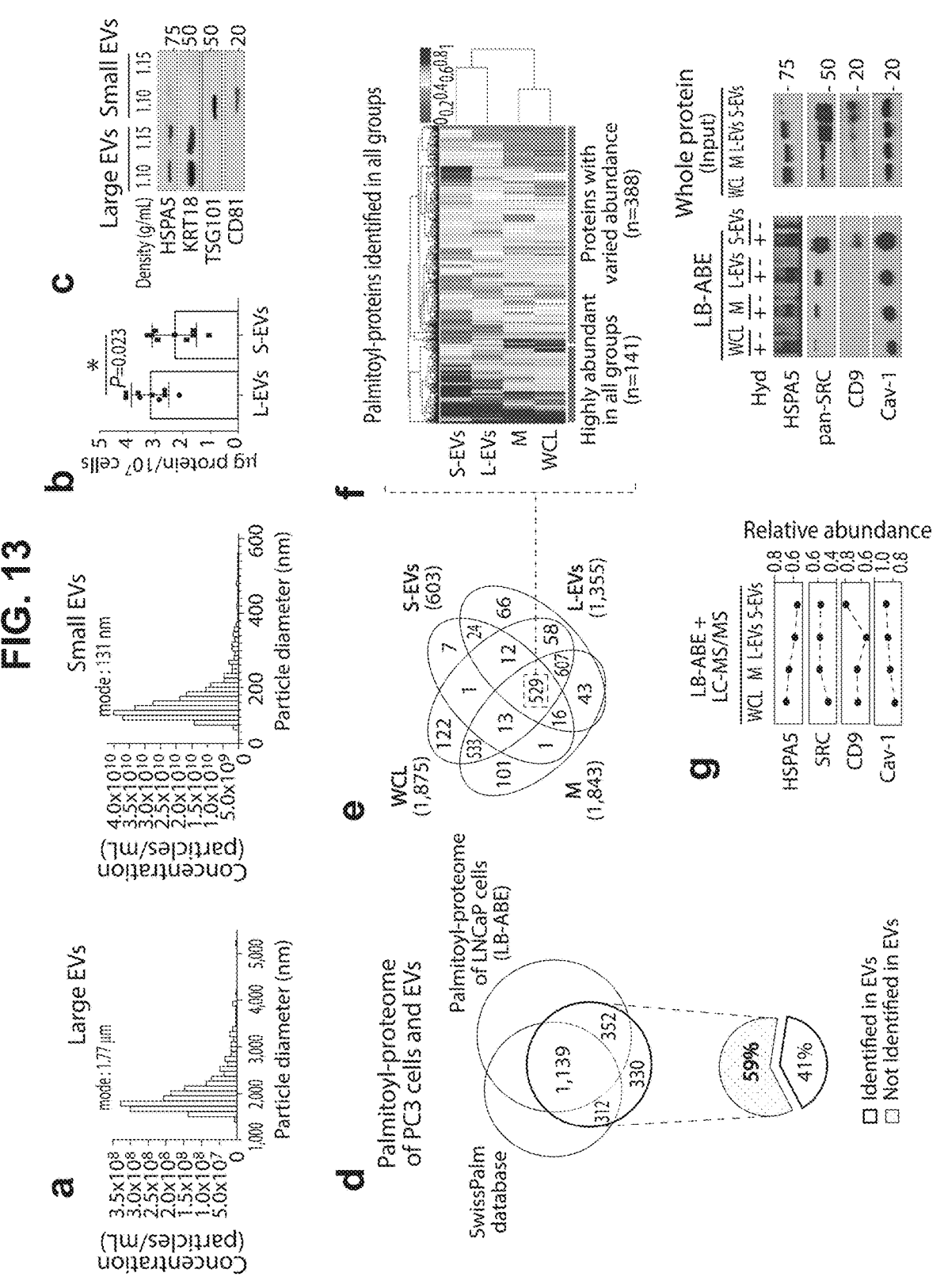
FIG. 13, panels a-g, depicts large-scale MS analysis identifies the palmitoyl-protein signature of prostate cancer cells and EVs. (a) Quantification and particle size distribution of PC3EVs by TRPS. Histogram plots depicted with a bin width of 100 and 10 nm, respectively. (b) Yield of purified PC3 EV-protein after differential ultracentrifugation and density-gradient purification of conditioned media. (c) Immunoblotting of select proteins enriched either in L-EVs (HSPA5 and KRT18) or S-EVs (TSG101 and CD81). (d) Venn diagram showing the number of palmitoylated proteins identified in PC3 cells by LB-ABE in comparison to LNCaP cells and the number of known human palmitoyl-proteins compiled in the SwissPalm database. (e) Venn diagram showing the number of unique and common palmitoylated proteins in WCL, M, L-EVs and S-EVs. (f) Unsupervised heat map and dendrogram of the normalized relative abundance of the common palmitoyl-proteins. Clustering analysis identifies a group of palmitoylated proteins highly abundant across all subcellular compartments and a group of proteins with varied abundance. (g) Left, dot plot shows the relative abundance of the indicated palmitoyl-proteins in WCL, M, L-EVs and S-EVs by MS analysis and max(1)-min(0) normalization. Middle, immunoblotting against the indicated palmitoyl-proteins from WCL, M, L-EVs and S-EVs in presence (Hyd+) or absence of hydroxylamine (Hyd−) confirms specific enrichment of palmitoyl-proteins by LB-ABE. Right, immunoblotting of WCL, M, L-EV and S-EV lysates taken prior the enrichment of palmitoylated proteins in order to confirm the expression and distribution of the indicated proteins.

In order to perform quantitative analysis, we selected for high confidence palmitoyl-proteins resulting in a total of 1,875, 1,843, 1,355 and 603 palmitoyl-proteins in WCL, M, L-EVs and S-EVs, respectively (FIG. 13(*e*)). Our stringent quality criteria resulted in a smaller number of proteins identified in S-EVs due to lower initial protein input. However, similar correlation coefficients among the technical replicates for S-EVs and L-EVs suggest a similar reproducibility for the enrichment of palmitoyl-proteins in both EV populations (data not shown). Clustering of the palmitoyl-proteins detected in all 4 fractions (WCL, M, L-EVs and S-EVs) (FIG. 13(*e*)) identified 141 proteins that were consistently highly abundant across all fractions and 388 proteins with varied abundance (FIG. 13(*f*)). Among the proteins with varied abundance, 31 were more abundant in L-EVs and 98 in S-EVs (data not shown), suggesting that S-EVs harbour a more discrete palmitoyl-protein signature than L-EVs. Functional enrichment analysis of the 141 highly abundant proteins identified in all four fractions including EVs showed significant association with major biological processes relevant to cancer (e.g., adhesion and cellular movement) (data not shown). Importantly, vesicle-mediated transport was also identified as one of the most prominent functions of the highly abundant palmitoylated proteins identified (data not shown). These data suggest that palmitoylation is functionally significant in the biology of cancer and EVs.

Western blotting confirmed expression of palmitoyl-proteins in the fractions enriched for palmitoylated proteins (Hyd+) but not in the control groups (Hyd−), confirming specific recovery following LB-ABE (FIG. 13(*g*)). Src-family tyrosine kinases and Cav-1, which are known to be highly palmitoylated, were identified with high confidence in all fractions (FIG. 13(*g*)). HSPA5 was enriched in L-EVs as total protein but we found it to be equally represented in L- and S-EVs as a palmitoylated protein. CD9 is enriched in S-EVs both as a total and as palmitoyl-protein. We also noticed that the palmitoylated form of CD81 was significantly enriched in L-EVs, despite its "canonical" description as an S-EV marker, based on total protein analysis. This result suggests that the palmitoyl status of certain proteins can determine their sorting to different EV fractions.

L- and S-EVs Exhibit Distinct Profiles that Distinguish them from their Parental Cells We and others have previously demonstrated that EVs contain not only proteins that are highly expressed in the originating cells, but they are also enriched in proteins of low abundance in the cell. Moreover, discrete EV populations contain a set of distinct proteins, suggesting cargo selection. In order to determine whether this cargo selection is evident in the palmitoyl-proteome, we compared L- and S-EVs to the originating cells. Because palmitoylation is a membrane-anchoring modification and EVs are membrane encapsulated particles, we compared the palmitoyl-proteins identified in EVs and M fractions. The majority (roughly 90%) of them was identified in both compartments (data not shown), in line with the rich membrane composition of EVs. However, when we looked at the relative abundance of these proteins in EVs versus M, we found a weak correlation (r=0.444 in L-EVs/M; r=0.317 in S-EVs/M). Conversely, the correlation between M and WCL was higher (r=0.782 in WCL/M) (FIG. 14(*a*)), suggesting selective enrichment of palmitoylated proteins in EVs.

Figure 14:
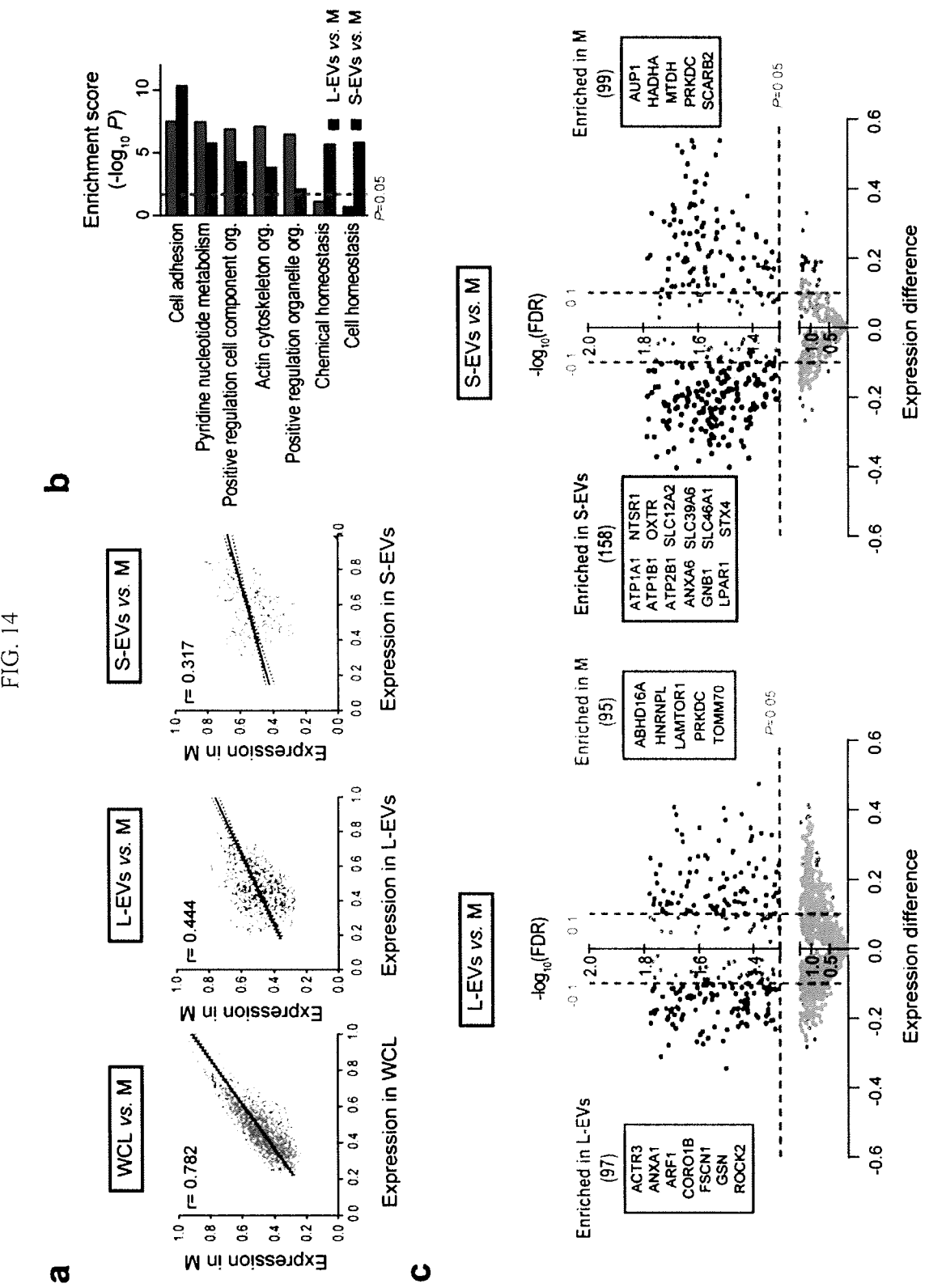
FIG. 14, panels a-c, depicts L- and S-EVs exhibit distinct palmitoyl-protein profiles that distinguish them from their parental cells. (a) Regression analysis of the relative abundance of the palmitoyl-proteins identified in WCL, M, L-EVs and S-EVs. Spearman's coefficient (r) demonstrates a low correlation between EVs and M when compared to WCL and M. (b) The biological functions overrepresented in L- and S-EVs in comparison to M identified by functional enrichment analysis of the palmitoyl-proteome differentially expressed in EVs using DAVID software. (c) Volcano plots showing differential protein expression between L- and S-EVs compared to M. X and Y axes represent the normalized expression difference and $-\log_{10}$(FDR), respectively. Red and blue dots correspond to palmitoyl-proteins significantly enriched either in L- or S-EVs, respectively, compared to those enriched in the M (green dots). The blue and red boxes highlight functionally relevant proteins to the biological processes differentially represented in L-EVs and S-EVs shown in panel B. The green boxes highlight the top 5 proteins enriched in M.

Functional enrichment analysis revealed that the palmitoyl-proteins significantly enriched in both L- and S-EVs were involved in pyridine nucleotide metabolism and cell adhesion (FIG. 14(*b*)), and included proteins known to be involved in modulating cell polarity, adhesion and migration. These comprised membrane-anchored integrins (ITGA2, ITGA6, ITGB4), claudins (CLDN1, CLDN11), and cytoskeletal proteins such as the Rho-associated moesin (MSN), vinculin (VCL), ezrin (EZR), ROCK2 and the Ras GTPase-activating-like protein IQGAP. Cell functions enriched in L-EVs versus M were associated with positive regulation of organelle and cell component organization, as well as actin cytoskeleton organization (FIG. 14(*b*)). In contrast, cell functions enriched in S-EVs versus M were associated with cell and chemical homoeostasis (FIG. 14(*b*)).

Detailed analysis of the palmitoylated proteins involved in these biological processes revealed that, while the differentially enriched proteins in L-EVs were mostly represented by cytoplasmic proteins involved in cell growth (GSN, FSCN1 and ATCR3) and signal transduction (ANXA1, ARF1, ROCK2 and COROIB); the proteins enriched in S-EVs were mainly represented by two major groups of plasma membrane proteins (FIG. 14(*c*)). The first group contained two families of transmembrane palmitoyl-proteins with transporter activity: the P-type ATPase superfamily (ATP1A1, ATP1B1 and ATP2B1) and the cation transporters (SLC12A2, SLC39A6 and SLC46A1). The second group contained palmitoyl-proteins associated with signal transduction and cell communication (ANXA6, LPAR1, GNB1, LYN, NTSR1, OXTR and STX4) (FIG. 14(*c*)).

Figure 15:
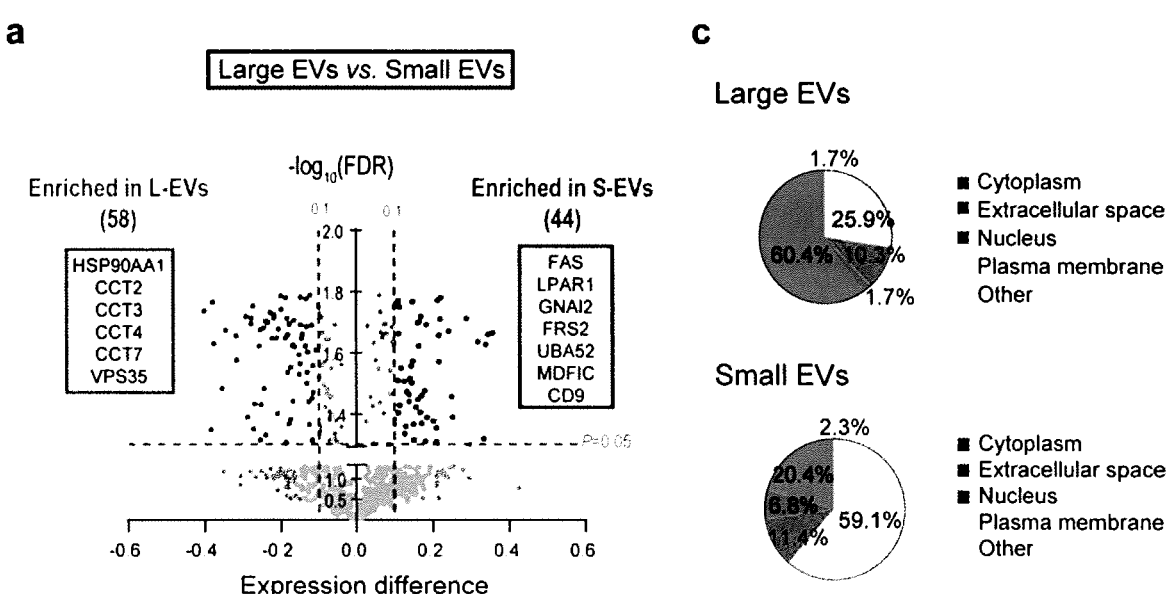
FIG. 15, panels a-c, depicts palmitoyl-protein profiles of L- and S-EVs are associated with EV population-specific biological processes and subcellular origin. (a) Volcano plot showing differential protein expression between L-EVs and S-EVs. X and Y axes represent the normalized expression difference and $-\log_{10}$(FDR), respectively. The red and blue boxes highlight functionally relevant palmitoyl-proteins to the biological processes differentially represented in L- and S-EVs shown in panel B. (b) The biological functions overrepresented in L- and S-EVs identified by functional enrichment analysis of the palmitoyl-proteome differentially expressed in EVs using DAVID software. (c) Pie charts indicating the main subcellular localization of the palmitoylated proteins differentially enriched in L- and S-EVs, as defined by the Ingenuity Knowledge database.
Figure 15:
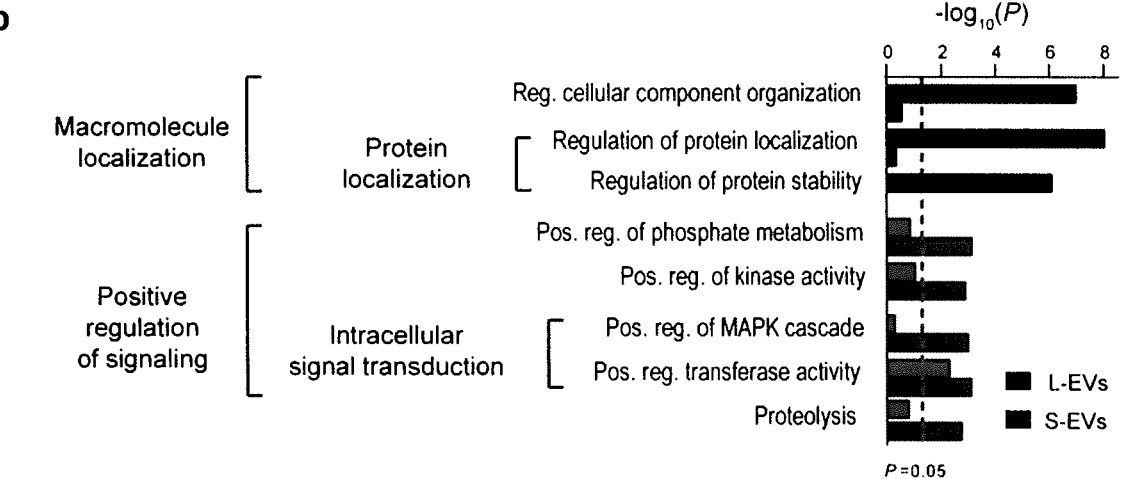

Palmitoyl-Proteomic Profiles of L- Versus S-EVs Reflect EV Population-Specific Biological Processes and Subcellular Origin Ninety-seven palmitoyl-proteins were detected only in EVs, with 66 unique to L-EVs, 7 unique to S-EVs, and 24 common to both EV types (FIG. 13(*e*)). To further explore the difference between the palmitoyl-proteomes of L-EVs and S-EVs, we compared the proteins differentially enriched in each EV population 581 proteins (24+12+529+16) were detected in both S-EV and L-EVs but not unique to them (FIG. 13(*e*)). Among these, 58 proteins were significantly enriched in L-EVs and 44 proteins were significantly enriched in S-EVs (FIG. 15(*a*)). Functional analysis showed that palmitoyl-proteins enriched in L-EVs were associated with protein localization, regulation of protein stability, regulation of cell component organization and cellular localization (FIG. 15(*b*)). This association was mainly represented by the Vacuolar Protein-sorting Associated Protein 35 (VPS35), which is involved in trafficking of proteins, and by several members of the chaperone (HSP90AA1) and chaperonin-containing T-complex (CCT2, CCT3, CCT4, CCT7), which have been described to participate in the folding of nascent proteins, as well as in vesicular transport (FIG. 15(*a*)). Functional analysis of the palmitoyl-proteins enriched in S-EVs showed enrichment for proteins associated with cell communication, signalling processes, proteolysis and regulation of phosphate metabolism (FIG. 15(*b*)), and included the metalloproteinase ADAM17, the death receptor FAS and the ubiquitin UBA52 (FIG. 15(*a*)). The palmitoylated form of CD9, a tetraspanin highly enriched in S-EVs, was identified as significantly enriched in S-EVs in comparison to L-EVs (FIG. 15(*a*))—in agreement with the distribution observed for the non-palmitoylated form. Next we examined subcellular distribution of the palmitoyl-proteins differentially enriched in L- and S-EVs. Palmitoyl-proteins enriched in L-EVs were primarily associated with cytoplasm (60.4%), while those enriched in S-EVs were mainly associated with the plasma membrane (59.1%) (FIG. 15(*c*)). Importantly, 34 of the 35 cytoplasmic proteins enriched in L-EVs have been previously identified as palmitoylated by independent approaches, suggesting that they are genuine palmitoyl-proteins. Interestingly, both EV populations contained a smaller portion of nuclear proteins, which were similarly represented in both EV types (10.3% in L-EVs, 11.4% in S-EVs). Altogether, these data suggest a different subcellular derivation and functional/biological profiles of the palmitoylated proteins in L- and S-EVs.

Prostate Cancer-Derived EVs Contain Cancer-Specific Palmitoylated Proteins

Figure 16:
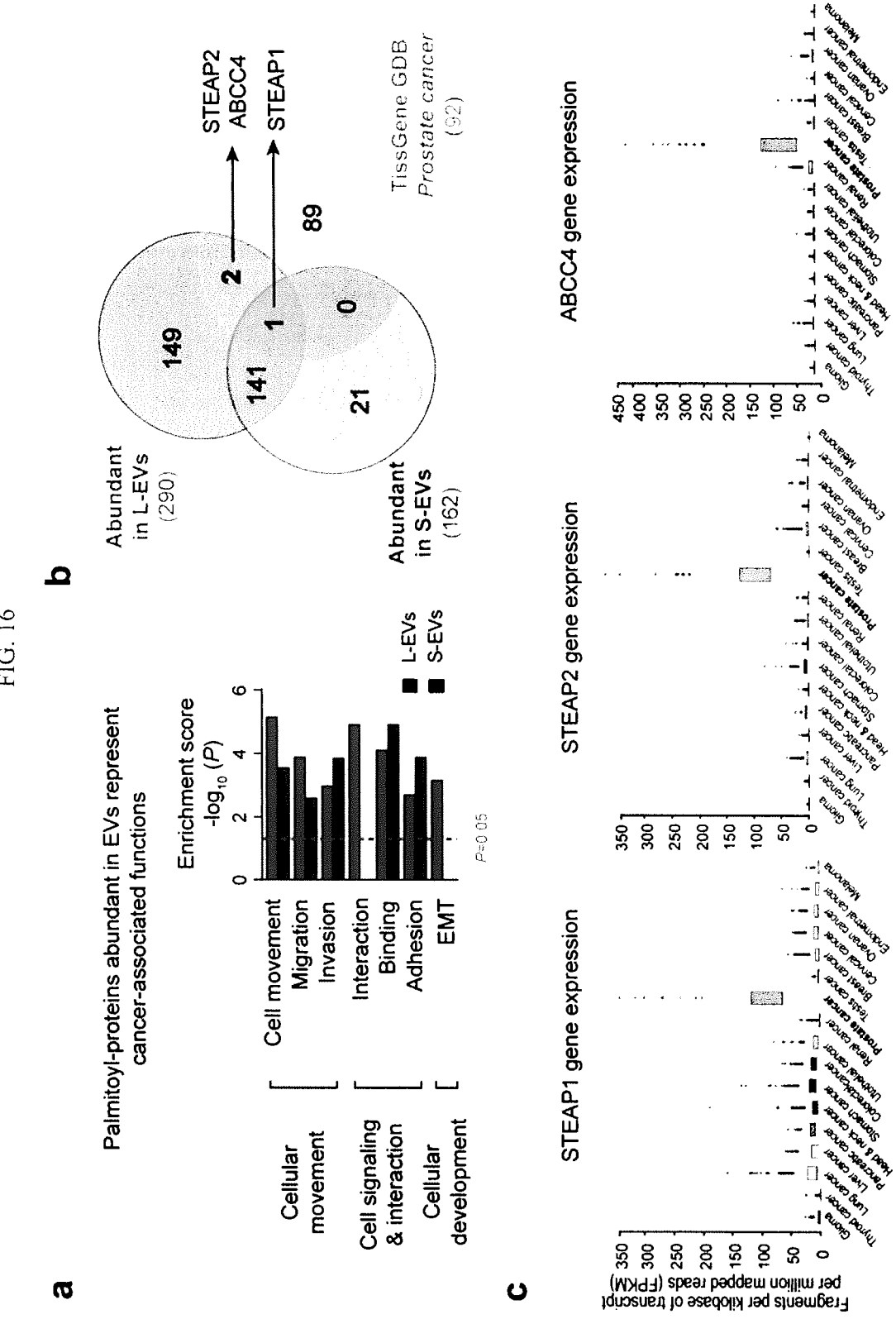
FIG. 16, panels a-c, depicts prostate cancer-derived EVs are enriched in prostate cancer-enriched palmitoyl-proteins. (a) Cancer-associated functions of the palmitoyl-proteins abundant in L- and S-EVs identified using IPA. (b) Venn diagram showing the number of palmitoyl-proteins abundant (determined by the rank product algorithm) in L- and S-EVs which are specifically enriched in prostate cancer according to the TissGene GDB. (c) The gene expression of STEAP1, STEAP2 and ABCC4 determined as fragments per kilobase of transcript per million mapped reads (FPKM) for select carcinomas according to the cancer genome atlas (TCGA) database.
Figure 16D:
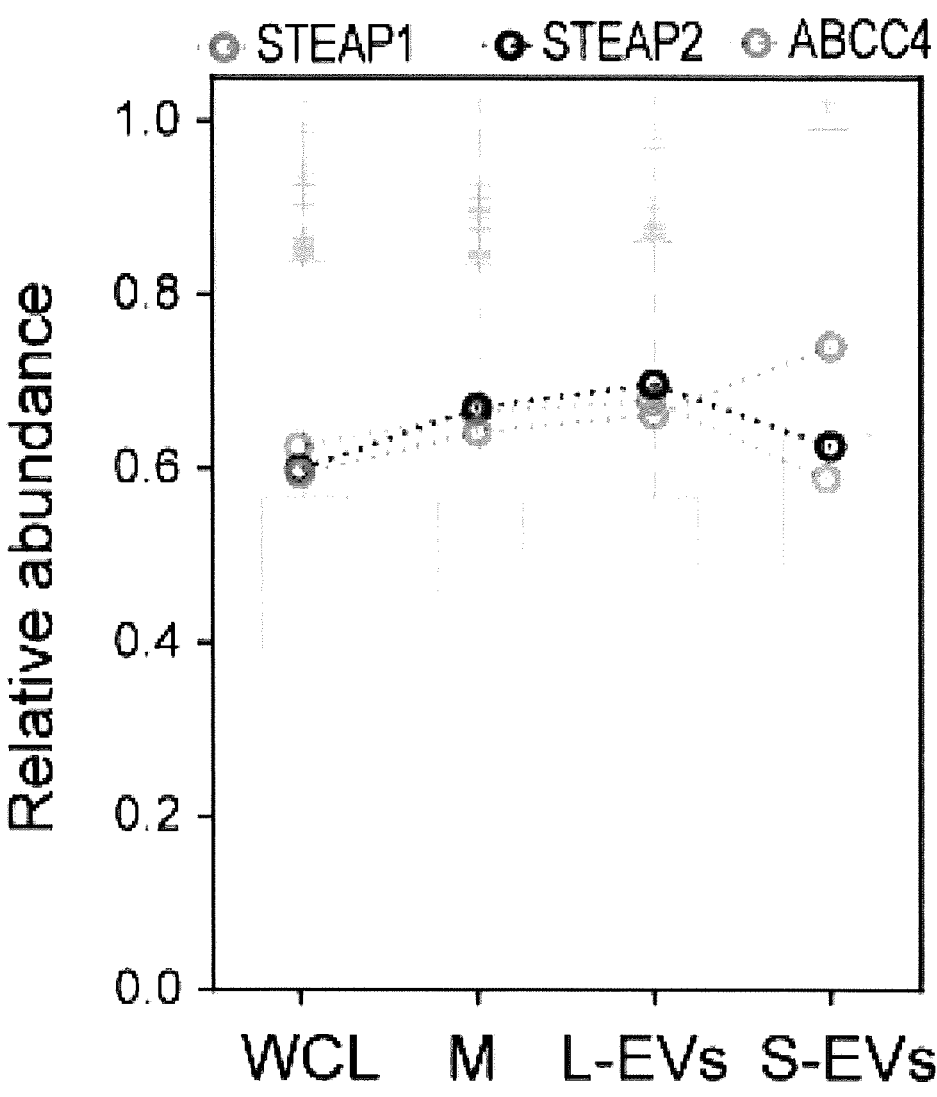
FIG. 16D depicts Palmitoylated PCa-specific proteins are highly abundant in EVs from PC3. A) Whisker and box plot of the relative abundance of palmitoyl-proteins detected by MS analysis in the indicated fractions. Dots indicate relative abundance of palmitoyl-STEAP1 (green), STEAP2 (blue) and ABCC4 (red). STEAP1 was identified as highly abundant in L- and S-EVs, whereas STEAP2 and ABCC4 were highly abundant in L-EVs.
Figure 17:
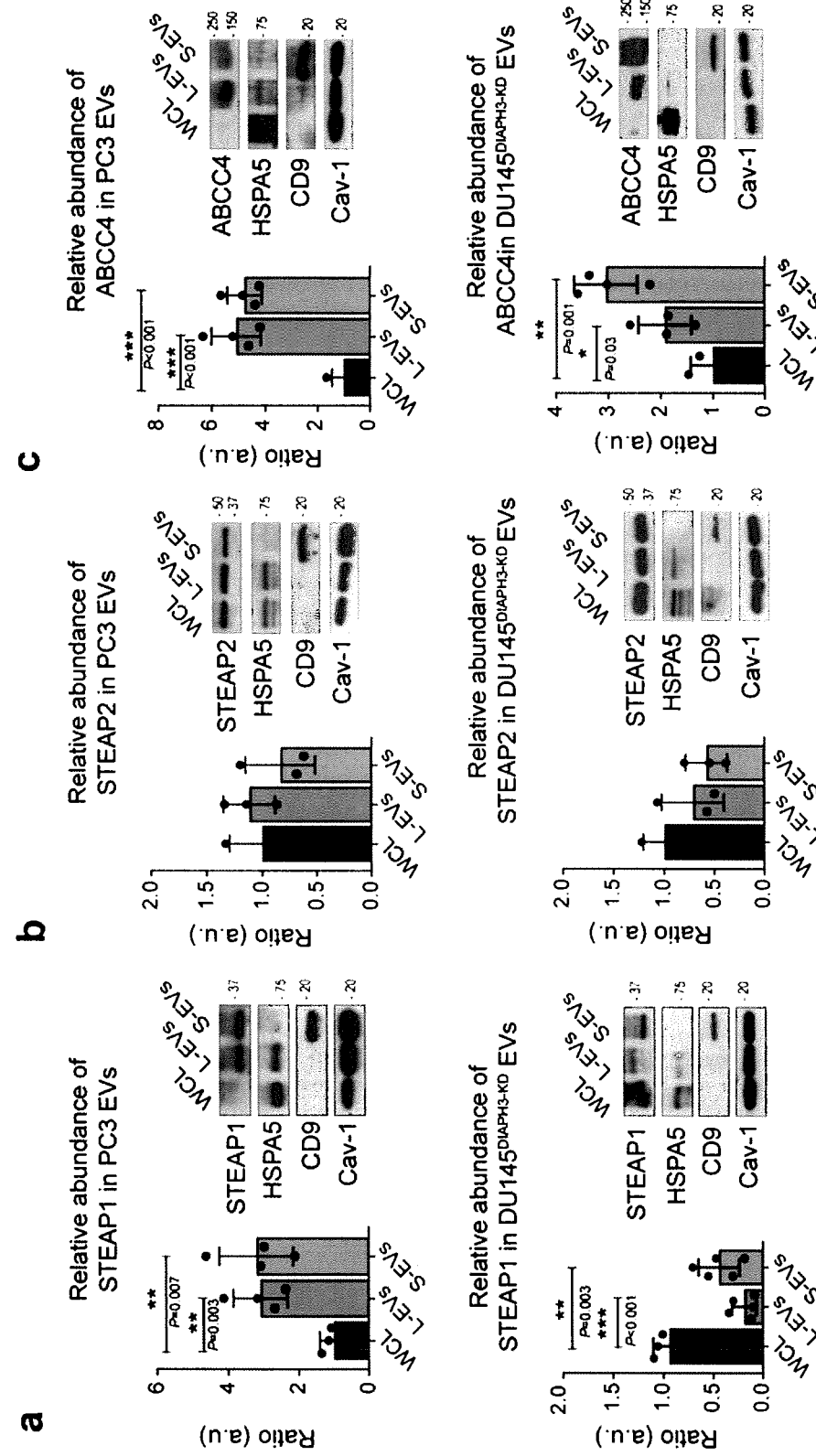
FIG. 17, panels a-f, depicts prostate cancer-specific proteins are enriched in EVs. (a-c) Representative immunoblot of STEAP1 (a), STEAP2 (b) and ABCC4 (c) in EVs and WCL from PC3 and DU145$^{DIAPH3-KD}$ cells along with the control proteins HSPA5 (L-EV enriched protein), CD9 (S-EV enriched protein) and Cav-1 (general EV protein). Bar plots represent the densitometric quantification across several blots. (d-f) FACS analysis of STEAP1 (d), STEAP2 (e) and ABCC4 (f) expression in cells and L-EVs from PC3 and DU145$^{DIAPH3-KD}$ cells.
Figure 17:
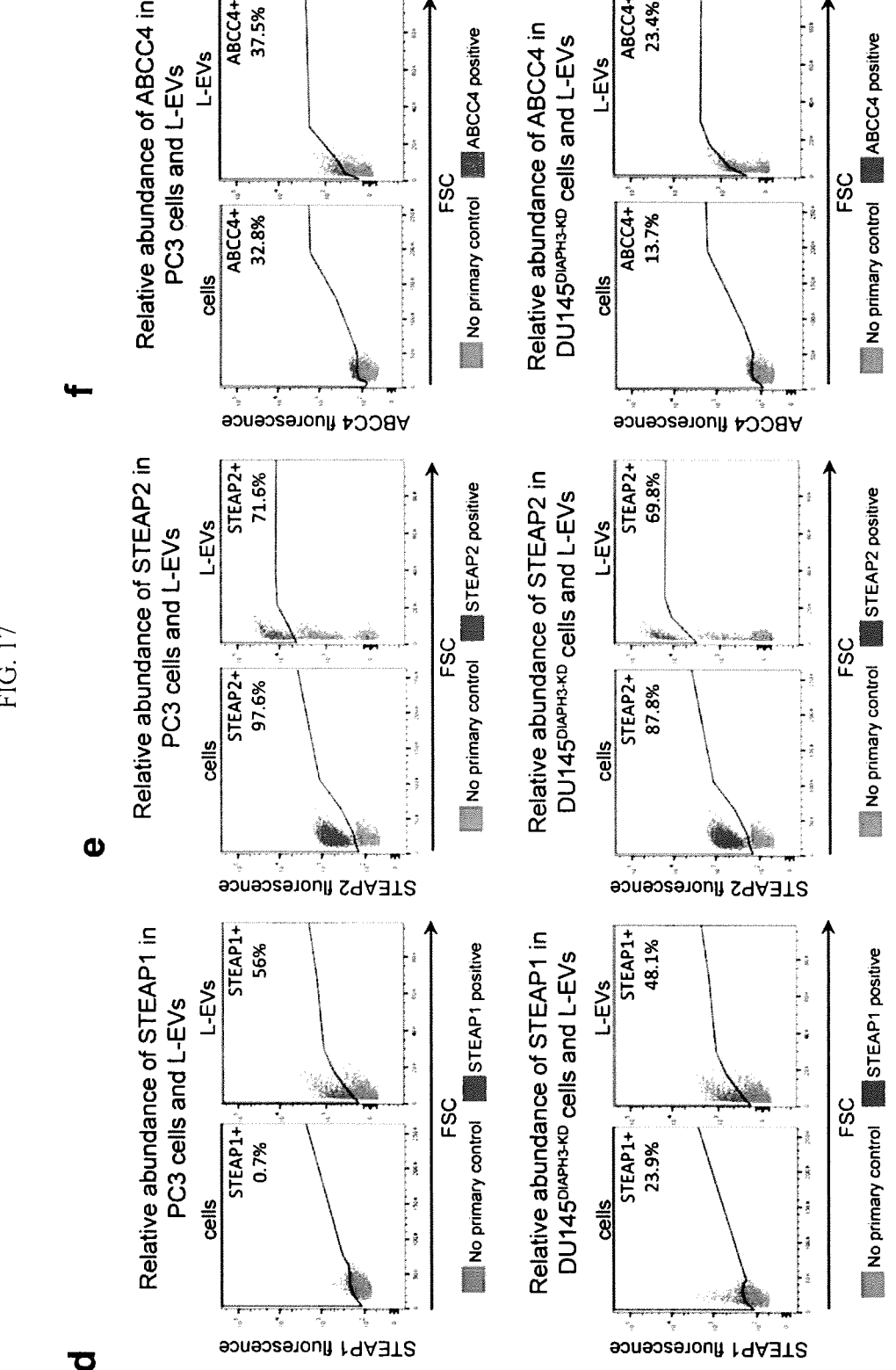

Altered palmitoyl transferase activity has been reported in cancer. In order to evaluate if the palmitoylation profile in EVs reflected cancer-associated functions, we selected for high-abundance palmitoylated proteins in EVs (Suppl. Table 1) and assessed their functional profile (FIG. 16(a)). We found a significant association with canonical cancer functions such as cell-to-cell signalling, adhesion, cell movement, and epithelial-to-mesenchymal transition (EMT). Using a panel of tissue-specific genes that combines the information from different databases, we identified 92 prostate cancer-specific/enriched genes. The multidrug-resistance-associated protein 4 (ABCC4), and the six-transmembrane epithelial antigen of prostate 1 (STEAP1) and 2 (STEAP2) (FIG. 16(b)) were identified as abundant palmitoyl-proteins in EVs. Importantly, these 3 genes are encoded by RNA that is highly expressed in prostate cancer tissue in comparison to other types of cancer (FIG. 16(c)). Interestingly, even though these proteins were abundant in both EV types, palmitoylated STEAP was more abundant in S-EVs, while STEAP2 and ABCC4 were more abundant in L-EVs (data not shown), confirming that EV heterogeneity is not limited to size but also affects cargo including protein post-translational modifications. Immunoblotting confirmed strong expression of STEAP1 in both populations of EVs from highly metastatic PC3 cells in comparison with the cells themselves (FIG. 17(a)). This was not the case for purified EVs from DU145$^{DIAPH3-KD}$ cells (data not shown), which is also highly metastatic, suggesting that STEAP1 expression in EVs is not indicative of disease aggressiveness. Conversely, STEAP2 was equally abundant in cells and both EVs from PC3 and DU145$^{DIAPH3-KD}$ cells (FIG. 17(b)). Finally, ABCC4 was highly enriched in EVs from PC3 and DU145$^{DIAPH3-KD}$ cells in contrast to the low expression detected in the parental cells (FIG. 17(c)). We also analysed these proteins at the single EV level using flow cytometry, and found that STEAP1 was highly expressed in both PC3 and DU145$^{DIAPH3-KD}$ L-EVs but virtually undetectable in PC3 cells (FIG. 17(d)). STEAP2 was highly abundant in both L-EVs and cells (FIG. 17(e)). ABCC4 was relatively enriched in L-EVs versus cells (FIG. 17(f)). Collectively, these results indicate that prostate cancer-specific proteins enriched in EVs are not necessarily abundant in cancer tissue and support the use of EV cargo as a source of clinically relevant circulating biomarkers.

Figure 18:
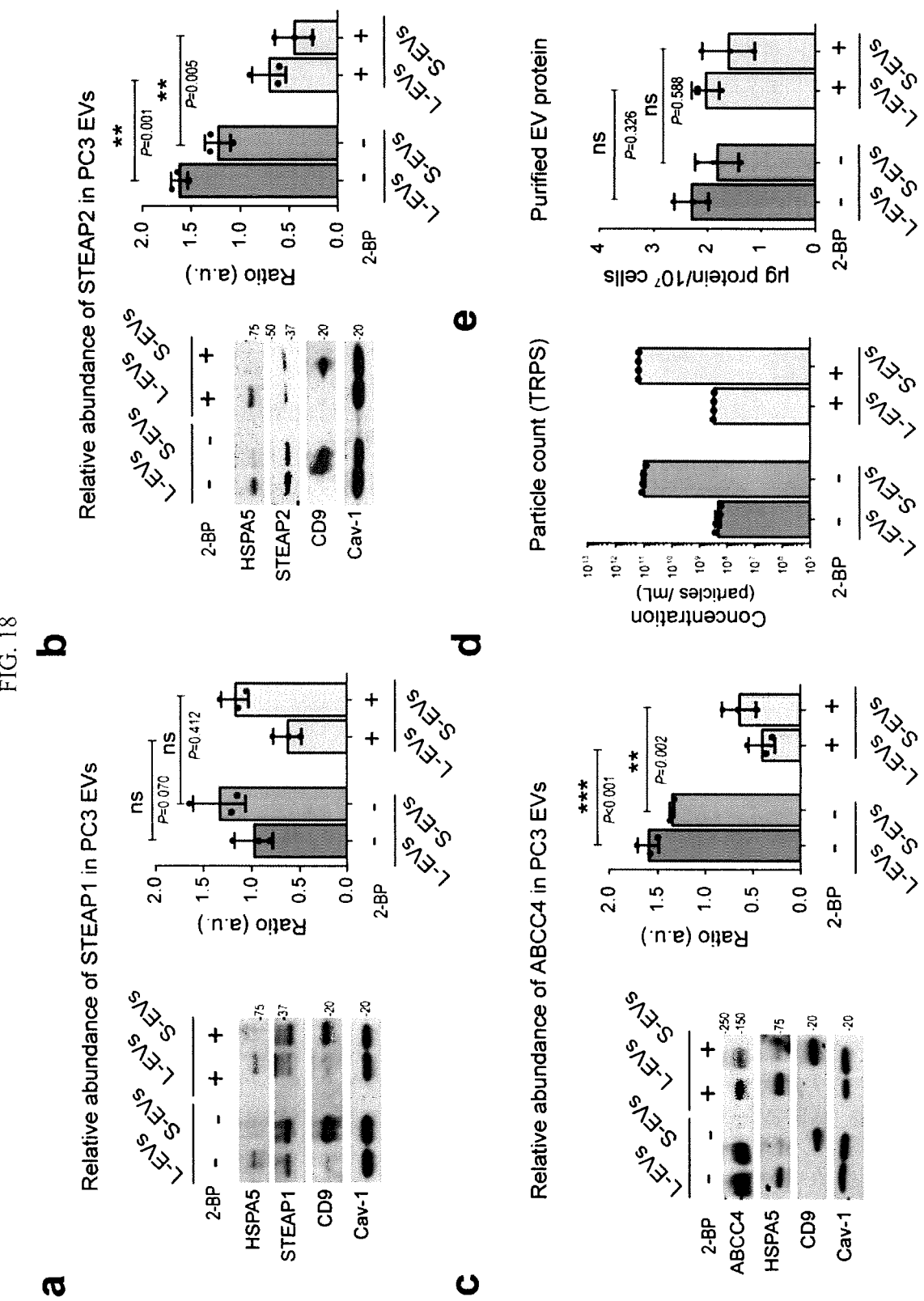
FIG. 18, panels a-e, depicts inhibition of palmitoylation reduces the abundance of prostate cancer-specific palmitoyl-proteins in EVs. (a-c) Representative immunoblot of the abundance of STEAP1 (A), STEAP2 (B) and ABCC4 (C) along with the control proteins HSPA5 (L-EV enriched protein), CD9 (S-EV enriched protein) and Cav-1 (general EV protein) in PC3 L- and S-EVs after inhibition of palmitoylation with 10 μM 2-BP for 24 h. Bar plots represent the densitometric quantification across replicate blots. (d) TRPS quantification of PC3 L- and S-EVs after inhibition of palmitoylation. (e) Yield of purified EV-protein from PC3 cells treated with or without 2-BP.
Figure 19:
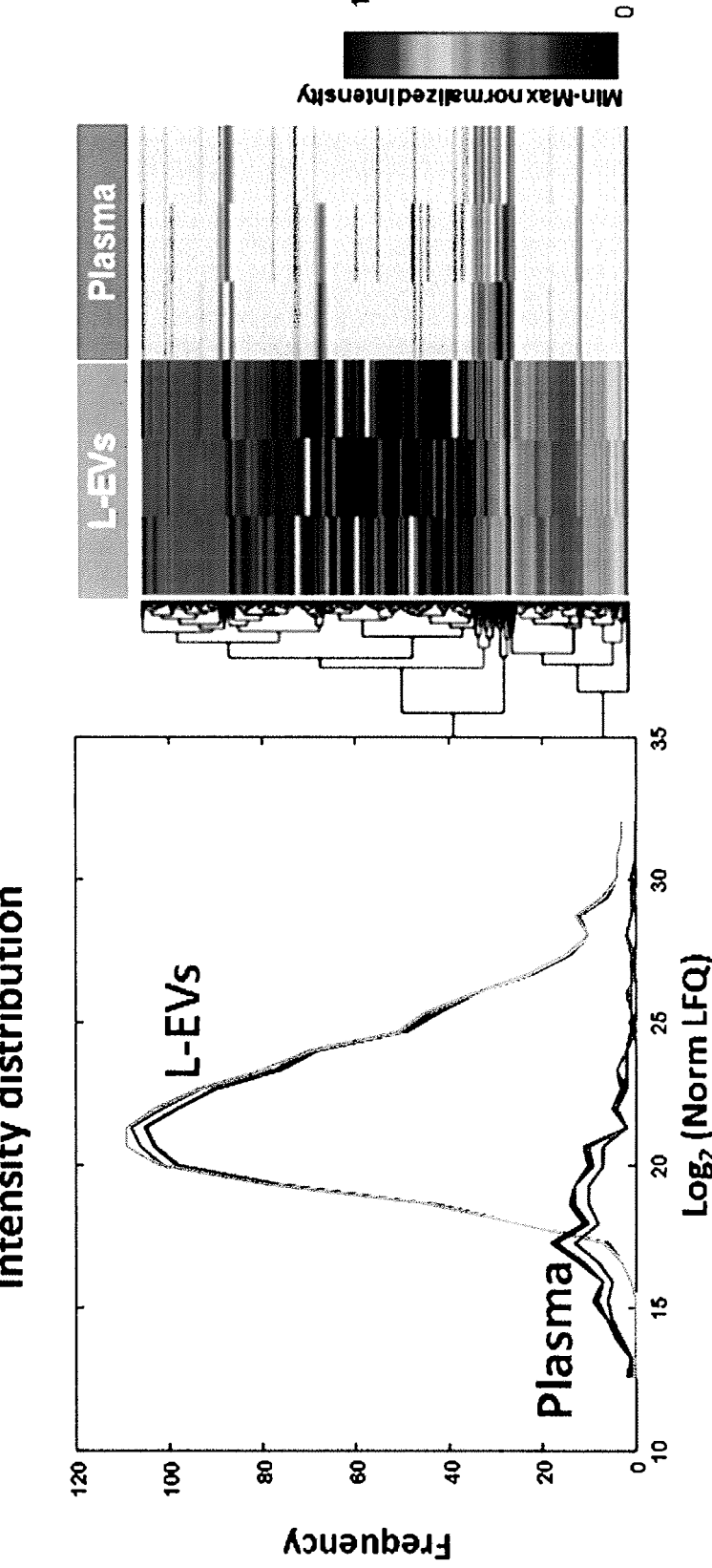
FIG. 19, panels A-C, depicts ABCC4 is highly enriched in the palmitoyl-proteome of purified L-EVs from metastatic PCa patients. A) Left, Intensity distribution of the log 2 normalized label-free quantitation signal (LFQ) from purified L-EVs and unfractionated plasma from metastatic PCa patients. Right, heatmap of the normalized expression of the palmitoylated proteins identified in density gradient purified EVs and unfractionated plasma from prostate cancer. Gray indicates proteins not identified. B) Top 20 more abundant palmitoyl-proteins identified in circulating L-EVs and not identified in straight plasma from PCa patients. C) Scatter plot of the normalized label-free quantitation (LFQ) signals of the palmitoylated proteins identified from purified PCa-derived L-EVs by LB-ABE enrichment followed by label-free proteomics analysis.

Finally, we investigated if palmitoylation had any influence on the localization of select proteins in EVs. To do so, we titrated the concentration of 2-bromopalmitate (2-BP), a general inhibitor of palmitoylation, to a non-toxic concentration of 10 μM in PC3 cells (data not shown) in order to avoid any alterations in the EV shedding (FIG. 18(d)) and recovery of EV-protein (FIG. 18(e)). Importantly, a number of studies have demonstrated inhibition of palmitoylation by this compound at the indicated dose. Treatment with 2-BP induced a decrease of STEAP1 (FIG. 18(a)), STEAP2 (FIG. 18(b)) and ABCC4 (FIG. 18(c)) in EVs, suggesting a role for protein palmitoylation in the trafficking and sorting of these proteins to EVs. Cav-1 levels in EVs did not change in response to 2-BP (data not shown), suggesting that palmitoylation of Cav-1 is not a requisite for its EV localization.

This is a novel observation but in line with previous studies that report that palmitoylation of Cav-1 is not necessary for its membrane localization.

Various embodiments of the invention are described above. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

The invention claimed is:

1. A method of detecting one or more palmitoyl proteins, comprising:
   obtaining a biological sample from a subject having prostate cancer or suspected of having prostate cancer;
   isolating large extracellular vesicles (EVs) from the biological sample;
   assaying the large EVs for palmitoyl proteins GNAQ, CD9, TLN1, STX11, ITGB3, LYN, SLC4A1, CANX, FLOT2, FLOT1, ABHD16A, MYADM, ATP2A3, TMX1, RAP2B, ATP2A2, SLC2A3, RTN4, LTBP1, and ABCC4; and
   detecting the palmitoyl proteins GNAQ, CD9, TLN1, STX11, ITGB3, LYN, SLC4A1, CANX, FLOT2, FLOT1, ABHD16A, MYADM, ATP2A3, TMX1, RAP2B, ATP2A2, SLC2A3, RTN4, LTBP1, and ABCC4.

2. The method of claim 1, further comprising assaying for one or more additional palmitoyl proteins other than GNAQ, CD9, TLN1, STX11, ITGB3, LYN, SLC4A1, CANX, FLOT2, FLOT1, ABHD16A, MYADM, ATP2A3, TMX1, RAP2B, ATP2A2, SLC2A3, RTN4, LTBP1, and ABCC4.

3. The method of claim 1, wherein the biological sample is blood plasma.

4. The method of claim 1, wherein the subject has prostate cancer.

5. The method of claim 1, wherein the subject has metastatic prostate cancer.

6. The method of claim 1, wherein assaying for palmitoyl proteins comprises using mass spectrometry to detect the palmitoyl proteins.

7. The method of claim 1, further comprising administering a prostate cancer therapy to the subject.

8. A method of detecting clinically significant prostate cancer, comprising:

obtaining a biological sample from a subject having prostate cancer or suspected of having prostate cancer;

isolating large extracellular vesicles (EVs) from the biological sample;

assaying the large EVs for palmitoyl proteins GNAQ, CD9, TLN1, STX11, ITGB3, LYN, SLC4A1, CANX, FLOT2, FLOT1, ABHD16A, MYADM, ATP2A3, TMX1, RAP2B, ATP2A2, SLC2A3, RTN4, LTBP1, and ABCC4; and detecting the palmitoyl proteins GNAQ, CD9, TLN1, STX11, ITGB3, LYN, SLC4A1, CANX, FLOT2, FLOT1, ABHD16A, MYADM, ATP2A3, TMX1, RAP2B, ATP2A2, SLC2A3, RTN4, LTBP1, and ABCC4, wherein the detection of the palmitoyl proteins indicates the presence of clinically significant prostate cancer.

9. The method of claim 8, further comprising administering a therapy other than androgen deprivation therapy when the one or more palmitoyl proteins are detected, or continuing to administer androgen deprivation therapy when the one or more palmitoyl proteins are not detected, or continuing active surveillance when the one or more palmitoyl proteins are not detected.

10. The method of claim 8, wherein assaying the large EVs for palmitoyl proteins comprises using mass spectrometry to assay for the palmitoyl proteins.

11. The method of claim 8, further comprising administering a prostate cancer therapy to the subject.

\* \* \* \* \*